(12) United States Patent
Wachendorff-Neumann et al.

(10) Patent No.: US 9,339,037 B2
(45) Date of Patent: May 17, 2016

(54) SYNERGISTIC FUNGICIDAL ACTIVE COMBINATIONS

(75) Inventors: Ulrike Wachendorff-Neumann, Neuwied (DE); Peter Dahmen, Neuss (DE); Ralf Dunkel, Lyons (FR); Hans-Ludwig Elbe, Wuppertal (DE); Heiko Rieck, Lyons (FR); Anne Suty-Heinze, Langenfeld (DE)

(73) Assignee: Bayer Cropscience AG, Monheim (DE)

( * ) Notice: Subject to any disclaimer, the term of this patent is extended or adjusted under 35 U.S.C. 154(b) by 1505 days.

(21) Appl. No.: 10/576,058

(22) PCT Filed: Oct. 12, 2004

(86) PCT No.: PCT/EP2004/011403
§ 371 (c)(1),
(2), (4) Date: Jul. 25, 2006

(87) PCT Pub. No.: WO2005/041653
PCT Pub. Date: May 12, 2005

(65) Prior Publication Data
US 2009/0018015 A1 Jan. 15, 2009

(30) Foreign Application Priority Data
Oct. 23, 2003 (DE) .................................. 103 49 501

(51) Int. Cl.
*A01N 37/22* (2006.01)
*A01N 37/50* (2006.01)
*A01N 43/56* (2006.01)
*A01N 43/653* (2006.01)
*A01N 43/88* (2006.01)
*A01N 43/54* (2006.01)
*A01N 47/32* (2006.01)
*A01N 43/08* (2006.01)
*A01N 43/10* (2006.01)
*A01N 43/32* (2006.01)
*A01N 43/36* (2006.01)
*A01N 43/40* (2006.01)
*A01N 43/78* (2006.01)
*A01N 37/18* (2006.01)
*A01N 43/50* (2006.01)

(52) U.S. Cl.
CPC ............... *A01N 47/32* (2013.01); *A01N 37/18* (2013.01); *A01N 37/22* (2013.01); *A01N 43/08* (2013.01); *A01N 43/10* (2013.01); *A01N 43/32* (2013.01); *A01N 43/36* (2013.01); *A01N 43/40* (2013.01); *A01N 43/50* (2013.01); *A01N 43/54* (2013.01); *A01N 43/56* (2013.01); *A01N 43/653* (2013.01); *A01N 43/78* (2013.01); *A01N 43/88* (2013.01)

(58) Field of Classification Search
None
See application file for complete search history.

(56) References Cited

U.S. PATENT DOCUMENTS

| | | | |
|---|---|---|---|
| 1,972,961 A | 9/1934 | Tisdale et al. | 167/22 |
| 2,504,404 A | 4/1950 | Flenner et al. | 167/22 |
| 2,553,770 A | 5/1951 | Kittleson | 167/33 |
| 2,588,428 A | 3/1952 | Stewart et al. | 167/22 |
| 3,010,968 A | 11/1961 | Loux | 260/309.2 |
| 3,178,447 A | 4/1965 | Kohn | 260/309.5 |
| 3,206,468 A | 9/1965 | Grenda | 260/302 |
| 3,248,400 A | 4/1966 | Flieg et al. | 260/313 |
| 3,249,499 A | 5/1966 | Von Schmeling et al. | 167/33 |
| 3,285,929 A | 11/1966 | Klauke et al. | 260/301 |
| 3,290,353 A | 12/1966 | Buttershell | 260/465 |
| 3,341,403 A | 9/1967 | Klauke et al. | 167/30 |
| 3,379,610 A | 4/1968 | Lyon et al. | 167/22 |
| 3,499,030 A | 3/1970 | Kuhle et al. | 260/551 |
| 3,499,951 A | 3/1970 | Schrader et al. | 260/951 |
| 3,513,241 A | 5/1970 | Hoyer et al. | 424/300 |
| 3,546,813 A | 12/1970 | Frohberger et al. | 47/57.6 |
| 3,629,411 A | 12/1971 | Schrader et al. | 424/217 |

(Continued)

FOREIGN PATENT DOCUMENTS

| | | |
|---|---|---|
| CA | 1 040 530 | 10/1978 |
| CA | 1311240 | 12/1992 |

(Continued)

OTHER PUBLICATIONS

Weeds, 15, (month unavailable) 1967, pp. 20-22, S.R. Colby, "Calculating Synergistic and Antagonistic Responses of Herbicide Combinations".

(Continued)

*Primary Examiner* — Abigail Fisher
*Assistant Examiner* — Frank Choi
(74) *Attorney, Agent, or Firm* — McBee Moore Woodward Vanik IP, LLC

(57) ABSTRACT

The present invention relates to novel active compound combinations having good fungicidal properties comprising a carboxamide of the general formula (I) (group 1)

(I)

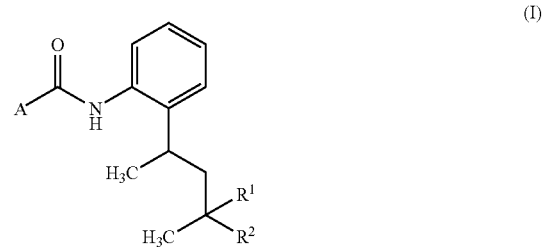

in which A, $R^1$ and $R^2$ are as defined in the disclosure, and the active compound groups (2) to (24) listed in the disclosure.

14 Claims, No Drawings

(56) References Cited

U.S. PATENT DOCUMENTS

| | | | |
|---|---|---|---|
| 3,629,428 A | 12/1971 | Seki et al. | 424/270 |
| 3,631,176 A | 12/1971 | Klopping | 260/309.2 |
| 3,663,575 A | 5/1972 | Roos et al. | 260/343.3 |
| 3,745,170 A | 7/1973 | Fujinami et al. | 260/326.5 S |
| 3,745,187 A | 7/1973 | Noguchi et al. | 260/455 |
| 3,755,350 A | 8/1973 | Sauli | 260/309.5 |
| 3,823,240 A | 7/1974 | Sauli | 424/273 |
| 3,856,814 A | 12/1974 | Taninaka et al. | 260/327 M |
| 3,903,090 A | 9/1975 | Fujinami et al. | 260/281 |
| 3,912,752 A | 10/1975 | Meiser et al. | 260/308 R |
| 3,952,002 A | 4/1976 | Kramer et al. | 260/308 R |
| 3,966,750 A | 6/1976 | Mangold et al. | 260/307 B |
| 3,991,071 A | 11/1976 | Brookes et al. | 260/309 |
| 3,995,049 A | 11/1976 | Mangold et al. | 424/272 |
| 4,009,278 A | 2/1977 | Fujinami et al. | 424/274 |
| 4,020,095 A | 4/1977 | Noguchi et al. | 260/470 |
| 4,029,813 A | 6/1977 | Noguchi et al. | 424/300 |
| 4,046,911 A | 9/1977 | Hubele | 424/285 |
| 4,048,318 A | 9/1977 | Meiser et al. | 424/269 |
| 4,068,077 A | 1/1978 | Goetz et al. | 544/178 |
| 4,079,062 A | 3/1978 | Van Reet et al. | 260/308 R |
| 4,080,462 A | 3/1978 | Brookes et al. | 424/273 R |
| 4,094,990 A | 6/1978 | Hubele | 424/285 |
| 4,127,673 A | 11/1978 | Yamada et al. | 424/322 |
| 4,139,616 A | 2/1979 | Ducret et al. | 424/222 |
| 4,147,791 A | 4/1979 | Meiser et al. | 424/269 |
| 4,151,299 A | 4/1979 | Hubele | 424/309 |
| 4,154,945 A | 5/1979 | Brookes et al. | 548/341 |
| 4,206,228 A | 6/1980 | Hubele | 424/300 |
| 4,239,760 A | 12/1980 | Sasse et al. | 424/249 |
| 4,245,432 A | 1/1981 | Dannelly | 47/57.6 |
| 4,272,417 A | 6/1981 | Barke et al. | 260/22 R |
| 4,291,049 A | 9/1981 | Bosone et al. | 424/275 |
| 4,294,850 A | 10/1981 | Hubele | 424/309 |
| 4,331,670 A | 5/1982 | Nishiyama et al. | 424/263 |
| 4,341,782 A | 7/1982 | Konishi et al. | 424/251 |
| 4,425,357 A | 1/1984 | Bosone et al. | 424/278 |
| 4,427,696 A | 1/1984 | Hubele | 424/309 |
| 4,436,744 A | 3/1984 | Harr | 424/272 |
| 4,439,447 A | 3/1984 | Hubele | 424/309 |
| 4,457,937 A | 7/1984 | Sandmeier et al. | 424/272 |
| 4,496,551 A | 1/1985 | Moberg | 514/63 |
| 4,510,136 A | 4/1985 | Moberg | 514/63 |
| 4,532,341 A | 7/1985 | Holmwood et al. | 549/559 |
| 4,551,469 A | 11/1985 | Parry et al. | 514/383 |
| 4,595,406 A | 6/1986 | Parry et al. | 71/76 |
| 4,598,085 A | 7/1986 | Heeres et al. | 514/383 |
| 4,608,385 A | 8/1986 | Noguchi et al. | 514/444 |
| 4,623,654 A | 11/1986 | Parry et al. | 514/383 |
| 4,626,595 A | 12/1986 | Holmwood et al. | 549/559 |
| 4,652,580 A | 3/1987 | Janssen et al. | 514/383 |
| 4,654,332 A | 3/1987 | Parry et al. | 514/184 |
| 4,659,739 A | 4/1987 | Yoshioka et al. | 514/555 |
| 4,664,696 A | 5/1987 | Schaub | 71/92 |
| 4,705,800 A | 11/1987 | Nyfeler et al. | 514/422 |
| 4,723,984 A | 2/1988 | Holmwood et al. | 71/76 |
| 4,731,106 A | 3/1988 | Green et al. | 71/92 |
| 4,780,551 A | 10/1988 | Nyfeler et al. | 549/422 |
| 4,789,672 A | 12/1988 | Holmwood et al. | 514/184 |
| 4,808,430 A | 2/1989 | Kouno | 427/4 |
| 4,824,469 A | 4/1989 | Green et al. | 71/76 |
| 4,829,085 A | 5/1989 | Wenderoth et al. | 514/522 |
| 4,840,959 A | 6/1989 | Oda et al. | 514/355 |
| 4,849,439 A | 7/1989 | Schaub | 514/383 |
| 4,851,405 A | 7/1989 | Krámer et al. | 514/212 |
| 4,871,390 A | 10/1989 | Holmwood et al. | 71/92 |
| 4,877,441 A | 10/1989 | Mori et al. | 71/90 |
| 4,880,457 A | 11/1989 | Parry et al. | 71/92 |
| 4,897,107 A | 1/1990 | Holmwood et al. | 71/92 |
| 4,902,705 A | 2/1990 | Hirota et al. | 514/397 |
| 4,904,298 A | 2/1990 | Holmwood et al. | 71/92 |
| 4,906,652 A | 3/1990 | Karbach et al. | 514/383 |
| 4,910,200 A | 3/1990 | Curtze et al. | 514/237.5 |
| 4,911,746 A | 3/1990 | Holmwood et al. | 71/92 |
| 4,920,139 A | 4/1990 | Fujimoto | 514/383 |
| 4,925,840 A | 5/1990 | Nyfeler et al. | 514/228.2 |
| 4,927,839 A | 5/1990 | Parry et al. | 514/383 |
| 4,931,560 A | 6/1990 | Hubele | 544/315 |
| 4,931,581 A | 6/1990 | Schurter et al. | 560/18 |
| 4,957,933 A | 9/1990 | Geffken et al. | 514/376 |
| 4,988,734 A | 1/1991 | Kraatz et al. | 514/624 |
| 4,992,438 A | 2/1991 | Ito et al. | 514/275 |
| 4,995,898 A | 2/1991 | Nasu et al. | 71/90 |
| 4,997,941 A | 3/1991 | Hubele | 544/332 |
| 5,004,816 A | 4/1991 | Mori et al. | 549/462 |
| 5,021,581 A | 6/1991 | Clough et al. | 546/309 |
| 5,059,623 A | 10/1991 | Krüger et al. | 514/613 |
| 5,081,141 A | 1/1992 | Colle et al. | 514/383 |
| 5,087,635 A | 2/1992 | Shaber | 514/383 |
| 5,112,849 A | 5/1992 | Staub et al. | 514/427 |
| RE33,989 E | 7/1992 | Wenderoth et al. | 514/522 |
| 5,145,856 A | 9/1992 | Clough et al. | 514/274 |
| 5,153,200 A | 10/1992 | Hubele | 514/275 |
| 5,185,342 A | 2/1993 | Hayase et al. | 514/274 |
| 5,190,928 A | 3/1993 | Schurter et al. | 514/63 |
| 5,221,691 A | 6/1993 | Clough et al. | 514/619 |
| 5,223,523 A | 6/1993 | Adams, Jr. et al. | 514/376 |
| 5,254,584 A | 10/1993 | Michelotti et al. | 514/514 |
| 5,256,683 A | 10/1993 | Hutt et al. | 514/383 |
| 5,264,440 A | 11/1993 | Clough et al. | 514/269 |
| 5,266,585 A | 11/1993 | Hubele et al. | 514/383 |
| 5,304,572 A | 4/1994 | Michelotti et al. | 514/514 |
| 5,306,712 A | 4/1994 | Tobitsuka et al. | 514/63 |
| 5,342,837 A | 8/1994 | Clough et al. | 514/247 |
| 5,356,908 A | 10/1994 | Geffken et al. | 514/333 |
| 5,371,222 A | 12/1994 | Hayase et al. | 544/316 |
| 5,371,223 A | 12/1994 | Hayase et al. | 544/316 |
| 5,380,743 A | 1/1995 | Hutt et al. | 514/399 |
| 5,395,837 A | 3/1995 | Clough et al. | 514/269 |
| 5,401,877 A | 3/1995 | Hayase et al. | 564/147 |
| 5,407,902 A | 4/1995 | Oda et al. | 504/336 |
| 5,438,059 A | 8/1995 | Clough et al. | 514/256 |
| 5,438,070 A * | 8/1995 | Eicken et al. | 514/403 |
| 5,453,531 A | 9/1995 | Seitz et al. | 560/29 |
| 5,468,747 A | 11/1995 | Clough et al. | 514/239.5 |
| 5,480,897 A * | 1/1996 | Eicken et al. | 514/365 |
| 5,486,621 A | 1/1996 | Phillion et al. | 549/4 |
| 5,514,643 A | 5/1996 | Rew et al. | 504/266 |
| 5,523,311 A | 6/1996 | Schurter et al. | 548/361 |
| 5,548,078 A | 8/1996 | Hayase et al. | 544/298 |
| 5,578,725 A | 11/1996 | Portoghese et al. | 546/35 |
| 5,593,996 A | 1/1997 | Pees et al. | 514/258 |
| 5,637,729 A | 6/1997 | Lacroix et al. | 548/316.7 |
| 5,639,918 A | 6/1997 | Hutt et al. | 568/329 |
| 5,650,519 A | 7/1997 | Lacroix et al. | 548/316.7 |
| 5,679,676 A | 10/1997 | Krüger et al. | 514/229.2 |
| 5,723,491 A | 3/1998 | Nuninger et al. | 514/538 |
| 5,747,518 A | 5/1998 | Yoshikawa et al. | 514/403 |
| 5,789,428 A | 8/1998 | Shibata et al. | 514/367 |
| 5,789,430 A | 8/1998 | Jautelat et al. | 514/272.4 |
| 5,859,039 A | 1/1999 | Jautelat et al. | 514/384 |
| 5,876,739 A | 3/1999 | Turnblad et al. | 424/408 |
| 5,883,250 A | 3/1999 | Krüger et al. | 540/544 |
| 5,914,344 A | 6/1999 | Yoshikawa et al. | 514/406 |
| 5,922,905 A | 7/1999 | Curtze | 562/474 |
| 5,945,567 A | 8/1999 | Curtze et al. | 568/333 |
| 5,948,932 A | 9/1999 | Grote et al. | 558/422 |
| 5,986,135 A | 11/1999 | Pfrengle et al. | 564/303 |
| 5,998,450 A | 12/1999 | Eicken et al. | 514/355 |
| 6,001,883 A | 12/1999 | Curtze et al. | 514/687 |
| 6,002,016 A | 12/1999 | Lacroix et al. | 548/318.1 |
| 6,018,052 A | 1/2000 | Lacroix et al. | 548/318.1 |
| 6,020,354 A | 2/2000 | Assmann et al. | 514/380 |
| 6,037,378 A | 3/2000 | Grote et al. | 514/640 |
| 6,054,592 A | 4/2000 | Müller et al. | 548/371.1 |
| 6,103,717 A | 8/2000 | Heinemann et al. | 514/229.2 |
| 6,127,547 A | 10/2000 | Assmann et al. | 548/302.1 |
| 6,160,001 A | 12/2000 | Assmann et al. | 514/395 |
| 6,228,884 B1 | 5/2001 | Nuninger et al. | 514/538 |
| 6,235,743 B1 | 5/2001 | Gayer et al. | 514/269 |
| 6,268,508 B1 | 7/2001 | Assmann et al. | 548/302.1 |
| 6,277,791 B1 | 8/2001 | Assmann et al. | 504/269 |
| 6,277,858 B1 | 8/2001 | Walter | 514/259 |
| 6,344,564 B1 | 2/2002 | Lacroix et al. | 548/318.1 |

(56) References Cited

U.S. PATENT DOCUMENTS

| | | |
|---|---|---|
| 6,355,634 B1 | 3/2002 | Isenring et al. ............ 514/227.5 |
| 6,359,133 B2 | 3/2002 | Gayer et al. .................... 544/319 |
| 6,372,692 B1 | 4/2002 | Assmann et al. ............. 504/269 |
| 6,387,939 B1 | 5/2002 | Assmann et al. ............. 514/395 |
| 6,407,100 B1 | 6/2002 | Isenring et al. ............ 514/227.5 |
| 6,407,233 B1 | 6/2002 | Heinemann et al. ............ 544/65 |
| 6,503,933 B1 | 1/2003 | Moloney et al. ............... 514/357 |
| 6,642,181 B2 | 11/2003 | Assmann et al. ............. 504/269 |
| 6,653,258 B1 | 11/2003 | Clough et al. ................. 504/239 |
| 6,660,690 B2 | 12/2003 | Asrar et al. ................... 504/100 |
| 6,683,211 B1 | 1/2004 | Lamberth et al. ............. 564/175 |
| 6,828,441 B2 | 12/2004 | Moloney et al. ............... 546/296 |
| 6,838,473 B2 | 1/2005 | Asrar et al. .................... 514/365 |
| 6,855,718 B2 | 2/2005 | Blasco et al. ............ 514/259.31 |
| 6,875,783 B2 | 4/2005 | Assmann et al. ............. 514/372 |
| 6,903,093 B2 | 6/2005 | Asrar et al. ................. 514/229.2 |
| 7,098,227 B2 | 8/2006 | Dunkel et al. ................. 514/365 |
| 7,314,958 B2 * | 1/2008 | Elbe et al. ..................... 564/176 |
| 7,358,214 B2 | 4/2008 | Dunkel et al. |
| 7,381,688 B2 | 6/2008 | Dunkel et al. |
| 7,459,477 B2 | 12/2008 | Furuya et al. |
| 7,538,073 B2 * | 5/2009 | Elbe et al. ..................... 504/280 |
| 2002/0091067 A1 | 7/2002 | Assmann et al. ............. 504/269 |
| 2002/0134012 A1 * | 9/2002 | Ding et al. ..................... 47/57.6 |
| 2002/0198222 A1 | 12/2002 | Bruns et al. .............. 514/259.31 |
| 2003/0027842 A1 | 2/2003 | Assmann et al. ............. 514/322 |
| 2003/0171410 A1 | 9/2003 | Moloney et al. ............... 514/357 |
| 2003/0176428 A1 | 9/2003 | Schneidersmann et al. ........................... 514/229.2 |
| 2004/0039043 A1 | 2/2004 | Elbe et al. ..................... 514/406 |
| 2004/0044054 A1 | 3/2004 | Assmann et al. ............. 514/372 |
| 2004/0110771 A1 | 6/2004 | Blasco et al. ............ 514/259.31 |
| 2004/0192672 A1 | 9/2004 | Wegmann et al. ....... 514/217.03 |
| 2004/0204470 A1 | 10/2004 | Elbe et al. ..................... 514/406 |
| 2005/0124815 A1 | 6/2005 | Elbe et al. ..................... 548/136 |
| 2005/0159464 A1 | 7/2005 | Assmann et al. ............. 514/372 |
| 2005/0197251 A1 | 9/2005 | Ding et al. ..................... 504/100 |
| 2006/0089399 A1 | 4/2006 | Dunkel et al. ................. 514/406 |
| 2006/0116414 A1 | 6/2006 | Dunkel et al. ................. 514/406 |
| 2006/0135538 A1 | 6/2006 | Blasco et al. ............ 514/259.31 |

FOREIGN PATENT DOCUMENTS

| | | |
|---|---|---|
| CA | 2 491 868 | 1/2004 |
| DE | 1 081 446 | 9/1956 |
| DE | 140 041 | 2/1980 |
| DE | 151 404 | 10/1981 |
| EP | 258 161 A2 | 3/1988 |
| EP | 329 397 B1 | 10/1993 |
| EP | 0 824 099 | 2/1998 |
| GB | 935981 | 9/1963 |
| GB | 988630 | 4/1965 |
| GB | 1094567 | 12/1967 |
| GB | 1103989 | 2/1968 |
| GB | 1114155 | 5/1968 |
| GB | 1 419 121 | 12/1975 |
| GB | 1 419 122 | 12/1975 |
| GB | 1 591 267 | 6/1981 |
| JP | 44-29464 | 12/1969 |
| JP | 63048269 A * | 2/1988 |
| JP | 7-206608 | 8/1995 |
| JP | 2001-72507 | 3/2001 |
| JP | 2001072508 | 3/2001 |
| WO | 02/38542 | 5/2002 |
| WO | 03/010149 | 2/2003 |
| WO | 2004/005242 | 1/2004 |

OTHER PUBLICATIONS

Pesticide Manual, 9$^{th}$ Edition, (month unavailable) 1991, p. 249, "Dichlofluanid".

Pesticide Manual, 9$^{th}$ Edition, (month unavailable) 1991, p. 827, "Tolyfluanid".

* cited by examiner

SYNERGISTIC FUNGICIDAL ACTIVE COMBINATIONS

The present patent application has been filed under 35 U.S.C. 371 as a national stage application of PCT/EP2004/011403, filed Oct. 12, 2004, which was published in German as International Patent Publication WO 2005/041653 on May 12, 2005, and is entitled to the right of priority of German Patent Application 10349501.0, filed Oct. 23, 2003.

The present invention relates to novel active compound combinations comprising firstly known carboxamides and secondly further known fungicidally active compounds, which novel active compound combinations are highly suitable for controlling unwanted phytopathogenic fungi.

It is already known that certain carboxamides have fungicidal properties: for example N-[2-(1,3-dimethylbutyl)phenyl]-5-fluoro-1,3-dimethyl-1H-pyrazole-4-carboxamide from WO 03/010149 and 3-trifluoromethyl-N-[2-(1,3-dimethylbutyl)phenyl]-5-fluoro-1-methyl-H-pyrazole-carboxamide from DE-A 103 03 589. The activity of these compounds is good; however, at low application rates it is sometimes unsatisfactory. Furthermore, it is already known that numerous triazole derivatives, aniline derivatives, dicarboximides and other heterocycles can be used for controlling fungi (cf. EP-A 0 040 345, DE-A 22 01 063, DE-A 23 24 010, Pesticide Manual, 9th Edition (1991), pages 249 and 827, EP-A 0 382 375 and EP-A 0 515 901). However, the action of these compounds is likewise not always sufficient at low application rates. Furthermore, it is already known that 1-(3, 5-dimethyl-isoxazole-4-sulphonyl)-2-chloro-6,6-difluoro-[1,3]-dioxolo-[4,5f]-benzimidazole has fungicidal properties (cf. WO 97/06171). Finally, it is also known that substituted halopyrimidines have fungicidal properties (cf. DE-A1-196 46 407, EP-B 0 712 396).

We have now found novel active compound combinations having very good fungicidal properties and comprising a carboxamide of the general formula (I) (group 1)

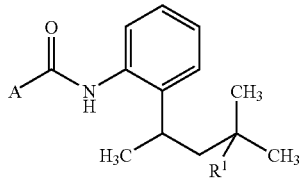

in which $R^1$ represents hydrogen, halogen, $C_1$-$C_3$-alkyl or $C_1$-$C_3$-haloalkyl having 1 to 7 fluorine, chlorine and/or bromine atoms, A represents one of the radicals A1 to A8 below:

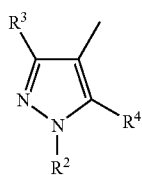

A1

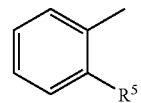

A2

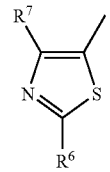

A3

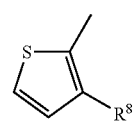

A4

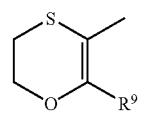

A5

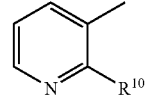

A6

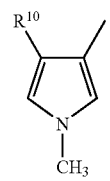

A7

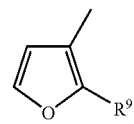

A8

$R^2$ represents $C_1$-$C_3$-alkyl, $R^3$ represents hydrogen, halogen, $C_1$-$C_3$-alkyl or $C_1$-$C_3$-haloalkyl having 1 to 7 fluorine, chlorine and/or bromine atoms, $R^4$ represents hydrogen, halogen or $C_1$-$C_3$-alkyl, $R^5$ represents halogen, $C_1$-$C_3$-alkyl or $C_1$-$C_3$-haloalkyl having 1 to 7 fluorine, chlorine and/or bromine atoms, $R^6$ represents hydrogen, halogen, $C_1$-$C_3$-alkyl, amino, mono- or di($C_1$-$C_3$-alkyl)amino, $R^7$ represents hydrogen, halogen, $C_1$-$C_3$-alkyl or $C_1$-$C_3$-haloalkyl having 1 to 7 fluorine, chlorine and/or bromine atoms, $R^8$ represents halogen, $C_1$-$C_3$-alkyl or $C_1$-$C_3$-haloalkyl having 1 to 7 fluorine, chlorine and/or bromine atoms, $R^9$ represents halogen, $C_1$-$C_3$-alkyl or $C_1$-$C_3$-haloalkyl having 1 to 7 fluorine, chlorine and/or bromine atoms, $R^{10}$ represents hydrogen, halogen, $C_1$-$C_3$-alkyl or $C_1$-$C_3$-haloalkyl having 1 to 7 fluorine, chlorine and/or bromine atoms, and at least one active compound selected from groups (2) to (24) below:

Group (2) Strobilurins of the general formula (II)

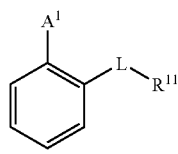
(II)

in which
$A^1$ represents one of the groups

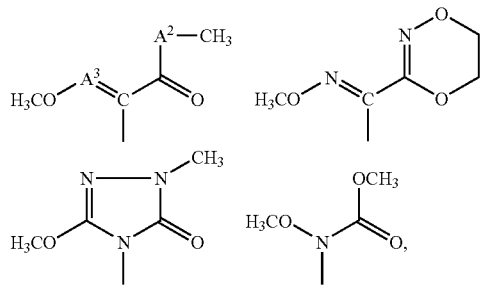

$A^2$ represents NH or O,
$A^3$ represents N or CH,
L represents one of the groups

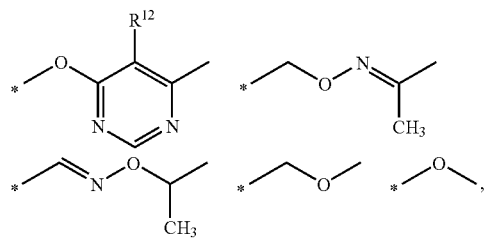

where the bond marked with an asterisk (*) is attached to the phenyl ring,
$R^{11}$ represents phenyl, phenoxy or pyridinyl, each of which is optionally mono- or disubstituted by identical or different substituents from the group consisting of chlorine, cyano, methyl and trifluoromethyl, or represents 1-(4-chlorophenyl)pyrazol-3-yl or represents 1,2-propanedione-bis(O-methyloxime)-1-yl,
$R^{12}$ represents hydrogen or fluorine;

Group (3) Triazoles of the general formula (III)

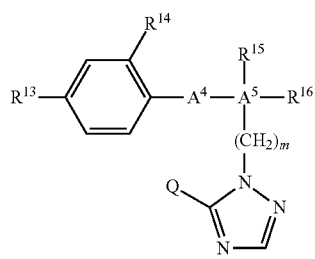
(III)

in which
Q represents hydrogen or SH,
m represents 0 or 1,
$R^{13}$ represents hydrogen, fluorine, chlorine, phenyl or 4-chlorophenoxy,
$R^{14}$ represents hydrogen or chlorine,
$A^4$ represents a direct bond, —CH$_2$—, —(CH$_2$)$_2$— or —O—,
$A^4$ furthermore represents *—CH$_2$—CHR$^{17}$— or *—CH=CR$^{17}$—, where the bond marked with * is attached to the phenyl ring, in which case $R^{15}$ and $R^{17}$ together represent —CH$_2$—CH$_2$—CH[CH(CH$_3$)$_2$]— or —CH$_2$—CH$_2$—C(CH$_3$)$_2$—,
$A^5$ represents C or Si (silicon),
$A^4$ further represents —N(R$^{17}$ and $A^5$ furthermore together with $R^{15}$ and $R^{16}$ represents the group C=N—R$^{18}$, in which case $R^{17}$ and $R^{18}$ together represent the group

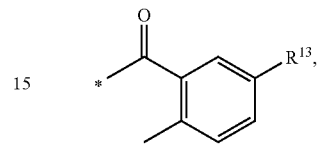

where the bond marked with * is attached to $R^{17}$,
$R^{15}$ represents hydrogen, hydroxyl or cyano,
$R^{16}$ represents 1-cyclopropylethyl, 1-chlorocyclopropyl, $C_1$-$C_4$-alkyl, $C_1$-$C_6$-hydroxyalkyl, $C_1$-$C_4$-alkylcarbonyl, $C_1$-$C_2$-haloalkoxy-$C_1$-$C_2$-alkyl, trimethylsilyl-$C_1$-$C_2$-alkyl, monofluorophenyl or phenyl,
$R^{15}$ and $R^{16}$ furthermore together represent —O—CH$_2$—CH(R$^{18}$)—O—, —O—CH$_2$—CH(R$^{18}$)—CH$_2$—, or —O—CH-(2-chlorophenyl)-,
$R^{18}$ represents hydrogen, $C_1$-$C_4$-alkyl or bromine;

Group (4) Sulphenamides of the general formula (IV)

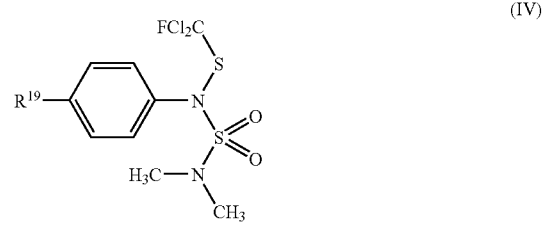
(IV)

in which $R^{19}$ represents hydrogen or methyl;

Group (5) Valinamides selected from
(5-1) iprovalicarb
(5-2) $N^1$-[2-(4-{[3-(4-chlorophenyl)-2-propynyl]oxy}-3-methoxyphenyl)ethyl]-$N^2$-(methylsulphonyl)-D-valinamide
(5-3) benthiavalicarb Group (6) Carboxamides of the general formula (V)

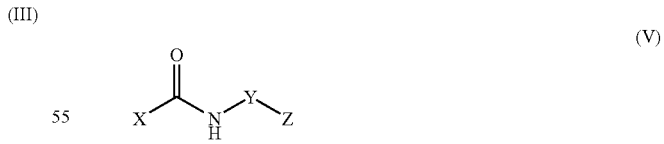
(V)

in which
X represents 2-chloro-3-pyridinyl, represents 1-methylpyrazol-4-yl which is substituted in the 3-position by methyl or trifluoromethyl and in the 5-position by hydrogen or chlorine, represents 4-ethyl-2-ethylamino-1,3-thiazol-5-yl, represents 1-methyl-cyclohexyl, represents 2,2-dichloro-1-ethyl-3-methylcyclopropyl, represents 2-fluoro-2-propyl or represents phenyl which is mono- to trisubstituted by identical or different substituents from the group consisting of chlorine and methyl, X furthermore represents 3,4-dichloroisothiazol-5-yl, 5,6-dihydro-2-methyl-1,4-oxathiin-3-yl, 4-methyl-1,2,3-thiadiazol-5-yl, 4,5-dimethyl-2-trimethylsilylthiophen-3-yl, 1-methylpyrrol-3-yl which is substituted in the 4-position by methyl or trifluoromethyl and in the 5-position by hydrogen or chlorine, Y represents a direct bond, $C_1$-$C_6$-alkanediyl (alkylene) which is optionally substituted by chlorine, cyano or oxo or represents thiophenediyl, Y furthermore represents $C_2$-$C_6$-alkenediyl (alkenylene), Z represents hydrogen or the group

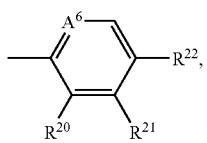

Z furthermore represents $C_1$-$C_6$-alkyl, $A^6$ represents CH or N, $R^{20}$ represents hydrogen, chlorine, phenyl which is optionally mono- or disubstituted by identical or different substituents from the group consisting of chlorine and di($C_1$-$C_3$-alkyl)amino-carbonyl, $R^{20}$ furthermore represents cyano or $C_1$-$C_6$-alkyl, $R^{21}$ represents hydrogen or chlorine, $R^{22}$ represents hydrogen, chlorine, hydroxyl, methyl or trifluoromethyl, $R^{22}$ furthermore represents di($C_1$-$C_3$-alkyl)amino-carbonyl, $R^{20}$ and $R^{21}$ furthermore together represent *—CH(CH$_3$)—CH$_2$—C(CH$_3$)$_2$— or *—CH(CH$_3$)—O—C(CH$_3$)$_2$— where the bond marked with * is attached to $R^{20}$;

group (7) Dithiocarbamates selected from (7-1) mancozeb (7-2) maneb (7-3) metiram (7-4) propineb (7-5) thiram (7-6) zineb (7-7) ziram Group (8) Acylalanines of the general formula (VI)

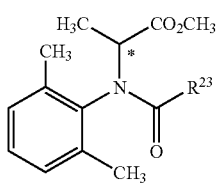

in which

* marks a carbon atom in the R or the S configuration, preferably in the S configuration, $R^{23}$ represents benzyl, furyl or methoxymethyl;

Group (9): Anilinopyrimidines of the general formula (VII)

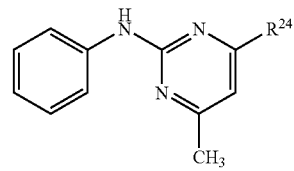

in which $R^{24}$ represents methyl, cyclopropyl or 1-propynyl;

Group (10): Benzimidazoles of the general formula (VIII)

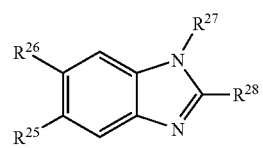

in which $R^{25}$ and $R^{26}$ each represent hydrogen or together represent —O—CF$_2$—O—, $R^{27}$ represents hydrogen, $C_1$-$C_4$-alkylaminocarbonyl or represents 3,5-dimethylisoxazol-4-ylsulphonyl, $R^{28}$ represents chlorine, methoxycarbonylamino, chlorophenyl, furyl or thiazolyl;

Group (11): Carbamates of the general formula (IX)

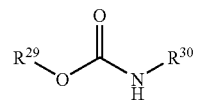

in which $R^{29}$ represents n- or isopropyl, $R^{30}$ represents di($C_1$-$C_2$-alkyl)amino-$C_2$-$C_4$-alkyl or diethoxyphenyl, salts of these compounds being included;

Group (12): Dicarboximides selected from (12-1) captafol (12-2) captan (12-3) folpet (124) iprodione (12-5) procymidone (12-6) vinclozolin Group (13): Guanidines selected from (13-1) dodine (13-2) guazatine (13-3) iminoctadine-triacetate (13-4) iminoctadine tris(albesilate)

Group (14): Imidazoles selected from (14-1) cyazofamid (14-2) prochloraz (14-3) triazoxide (14-4) pefurazoate Group (15): Morpholines of the general formula (X)

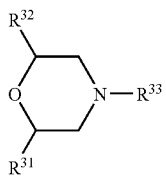

in which
$R^{31}$ and $R^{32}$ independently of one another represent hydrogen or methyl,
$R^{33}$ represents $C_1$-$C_{14}$-alkyl (preferably $C_{12}$-$C_{14}$-alkyl), $C_5$-$C_{12}$-cycloalkyl (preferably $C_{10}$-$C_{12}$-cycloalkyl), phenyl-$C_1$-$C_4$-alkyl, which may be substituted in the phenyl moiety by halogen or $C_1$-$C_4$-alkyl or represents acrylyl which is substituted by chlorophenyl and dimethoxyphenyl;

Group (16): Pyrroles of the general formula (XI)

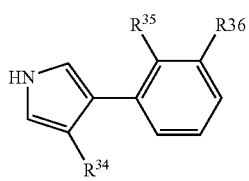

in which
$R^{34}$ represents chlorine or cyano,
$R^{35}$ represents chlorine or nitro,
$R^{36}$ represents chlorine,
$R^{35}$ and $R^{36}$ furthermore together represent —O—$CF_2$—O—;

Group (17): Phosphonates selected From
(17-1) fosetyl-Al
(17-2) phosphonic acid;

Group (18): Phenylethanamides of the general formula (XII)

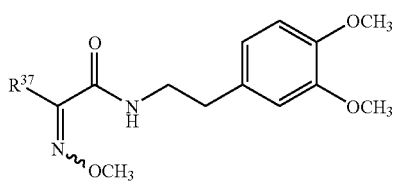

in which
$R^{37}$ represents unsubstituted or fluorine-, chlorine-, bromine-, methyl- or ethyl-substituted phenyl, 2-naphthyl, 1,2,3,4-tetrahydronaphthyl or indanyl;

Group (19): Fungicides selected from
(19-1) acibenzolar-5-methyl
(19-2) chlorothalonil
(19-3) cymoxanil
(19-4) edifenphos
(19-5) famoxadone
(19-6) fluazinam
(19-7) copper oxychloride
(19-8) copper hydroxide
(19-9) oxadixyl
(19-10) spiroxamine
(19-11) dithianon
(19-12) metrafenone
(19-13) fenamidone
(19-14) 2,3-dibutyl-6-chlorothieno[2,3-d]pyrimidin-4-(3H)-one
(19-15) probenazole
(19-16) isoprothiolane
(19-17) kasugamycin
(19-18) phthalide
(19-19) ferimzone
(19-20) tricyclazole.
(19-21) N-({4-[(cyclopropylamino)carbonyl]phenyl}sulphonyl)-2-methoxybenzamide
(19-22) 2-(4-chlorophenyl)-N-{2-[3-methoxy-4-(prop-2-yn-1-yloxy)phenyl]ethyl}-2-(prop-2-yn-1-yloxy)acetamide Group (20): (Thio)urea derivatives selected from
(20-1) pencycuron
(20-2) thiophanate-methyl
(20-3) thiophanate-ethyl Group (21): Amides of the General Formula (XIII)

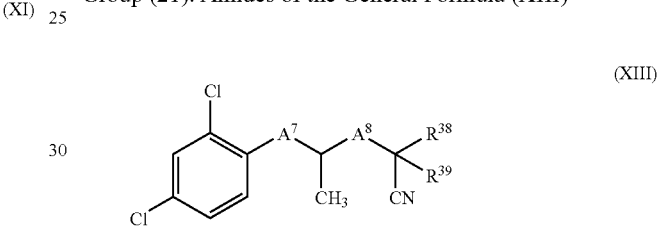

in which
$A^7$ represents a direct bond or —O—,
$A^8$ represents —C(=O)NH— or —NHC(=O)—,
$R^{38}$ represents hydrogen or $C_1$-$C_4$-alkyl,
$R^{39}$ represents $C_1$-$C_6$-alkyl;

Group (22): Triazolopyrimidines of the general formula (XIV)

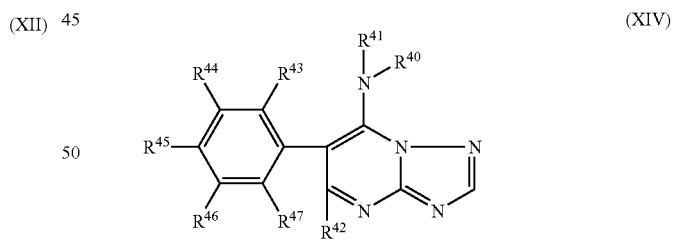

in which
$R^{40}$ represents $C_1$-$C_6$-alkyl or $C_2$-$C_6$-alkenyl,
$R^{41}$ represents $C_1$-$C_6$-alkyl,
$R^{40}$ and $R^{41}$ furthermore together represent $C_4$-$C_5$-alkanediyl (alkylene) which is mono- or disubstituted by $C_1$-$C_6$-alkyl,
$R^{42}$ represents bromine or chlorine,
$R^{43}$ and $R^{47}$ independently of one another represent hydrogen, fluorine, chlorine or methyl,
$R^{44}$ and $R^{46}$ independently of one another represent hydrogen or fluorine,
$R^{45}$ represents hydrogen, fluorine or ethyl, Group (23): Iodochromones of the general formula (XV)

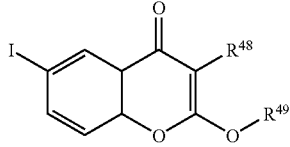
(XV)

in which
$R^{48}$ represents $C_1$-$C_6$-alkyl,
$R^{49}$ represents $C_1$-$C_6$-alkyl, $C_2$-$C_6$-alkenyl or $C_2$-$C_6$-alkynyl;
Group (24): Biphenylcarboxamides of the general formula (XVI)

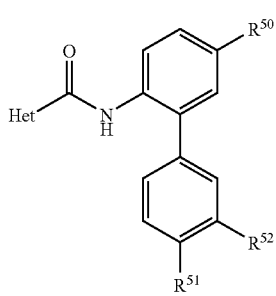
(XVI)

in which
$R^{50}$ represents hydrogen or fluorine,
$R^{51}$ represents fluorine, chlorine, bromine, methyl, trifluoromethyl, trifluoromethoxy, —CH=N—OMe or —C(Me)=N—OMe,
$R^{52}$ represents hydrogen, fluorine, chlorine, bromine, methyl or trifluoromethyl,
Het represents one of the radicals Het1 to Het7 below:

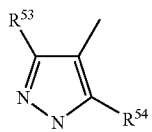
Het1

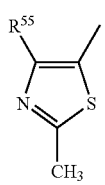
Het2

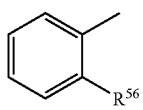
Het3

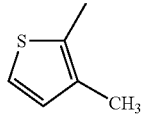
Het4

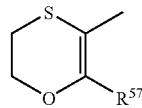
Het5

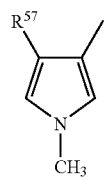
Het6

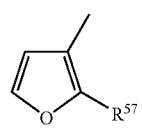
Het7

$R^{53}$ represents iodine, methyl, difluoromethyl or trifluoromethyl,
$R^{54}$ represents hydrogen, fluorine, chlorine or methyl,
$R^{55}$ represents methyl, difluoromethyl or trifluoromethyl,
$R^{56}$ represents chlorine, bromine, iodine, methyl, difluoromethyl or trifluoromethyl,
$R^{57}$ represents methyl or trifluoromethyl.

Surprisingly, the fungicidal action of the active compound combinations according to the invention is considerably better than the sum of the activities of the individual active compound. Thus, an unforeseeable true synergistic effect is present, and not just an addition of actions.

The formula (I) provides a general definition of the compounds of group (1).

Preference is given to carboxamides of the formula (I) in which
$R^1$ represents hydrogen, fluorine, chlorine, methyl, ethyl, n-, isopropyl, monofluoromethyl, difluoromethyl, trifluoromethyl, monochloromethyl, dichloromethyl or trichloromethyl,
A represents one of the radicals A1 to A5 below:

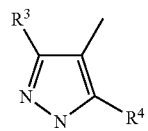
A1

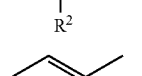
A2

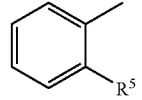
A3

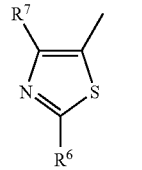

-continued

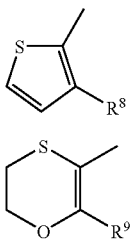
A4

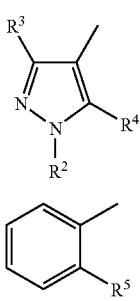
A5

R² represents methyl, ethyl, n- or isopropyl,
R³ represents iodine, methyl, difluoromethyl or trifluoromethyl,
R⁴ represents hydrogen, fluorine, chlorine or methyl,
R⁵ represents chlorine, bromine, iodine, methyl, difluoromethyl or trifluoromethyl,
R⁶ represents hydrogen, chlorine, methyl, amino or dimethylamino,
R⁷ represents methyl, difluoromethyl or trifluoromethyl,
R⁸ represents bromine or methyl,
R⁹ represents methyl or trifluoromethyl.

Particular preference is given to carboxamides of the formula (I) in which
R¹ represents hydrogen, fluorine, chlorine, methyl, ethyl or trifluoromethyl,
A represents one of the radicals A1 or A2 below:

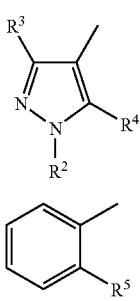
A1

A2

R² represents methyl or isopropyl,
R³ represents methyl, difluoromethyl or trifluoromethyl,
R⁴ represents hydrogen or fluorine,
R⁵ represents iodine, difluoromethyl or trifluoromethyl.

Very particular preference is given to carboxamides of the formula (I) in which
R¹ represents hydrogen or methyl,
A represents one of the radicals A1 or A2 below:

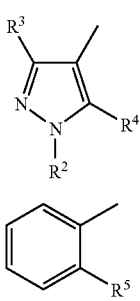
A1

A2

R² represents methyl,
R³ represents methyl,
R⁴ represents fluorine,
R⁵ represents iodine or trifluoromethyl.

Very particular preference is given to using, in mixtures, compounds of the formula (Ia)

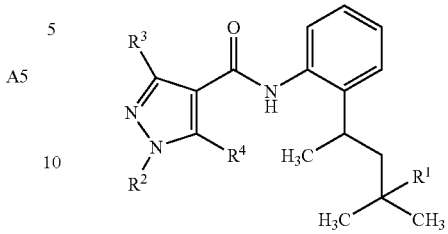
(Ia)

in which R¹, R², R³ and R⁴ are as defined above.

Very particular preference is given to using, in mixtures, compounds of the formula (Ib)

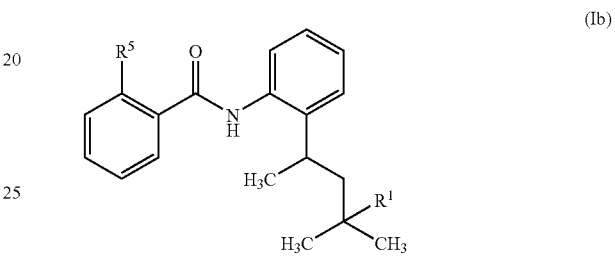
(Ib)

in which R¹ and R⁵ are as defined above.

The formula (I) embraces in particular the following preferred mixing partners of group (1):

(1-1) N-[2-(1,3-dimethylbutyl)phenyl]-1,3-dimethyl-1H-pyrazole-4-carboxamide
(1-2) N-[2-(1,3-dimethylbutyl)phenyl]-5-fluoro-1,3-dimethyl-1H-pyrazole-4-carboxamide (known from WO 03/010149)
(1-3) N-[2-(1,3-dimethylbutyl)phenyl]-5-chloro-1,3-dimethyl-1H-pyrazole-4-carboxamide (known from JP-A 10-251240)
(1-4) 3-difluoromethyl-N-[2-(1,3-dimethylbutyl)phenyl]-1-methyl-1H-pyrazole-4-carboxamide
(1-5) 3-trifluoromethyl-N-[2-(1,3-dimethylbutyl)phenyl]-5-fluoro-1-methyl-1H-pyrazole-4-carboxamide (known from DE-A 103 03 589)
(1-6) 3-trifluoromethyl-N-[2-(1,3-dimethylbutyl)phenyl]-5-chloro-1-methyl-1H-pyrazole-4-carboxamide (known from JP-A 10-251240)
(1-7) 1,3-dimethyl-N-[2-(1,3,3-trimethylbutyl)phenyl]-1H-pyrazole-4-carboxamide (known from JP-A 10-251240)
(1-8) 5-fluoro-1,3-dimethyl-N-[2-(1,3,3-trimethylbutyl)phenyl]-1H-pyrazole-4-carboxamide (known from WO 03/010149)
(1-9) 3-(difluoromethyl)-1-methyl-N-[2-(1,3,3-trimethylbutyl)phenyl]-1H-pyrazole-4-carboxamide
(1-10) 3-(trifluoromethyl)-1-methyl-N-[2-(1,3,3-trimethylbutyl)phenyl]-1H-pyrazole-4-carboxamide
(1-11) 3-trifluoromethyl)-5-fluoro-1-methyl-N-[2-(1,3,3-trimethylbutyl)phenyl]-1H-pyrazole-4-carboxamide (known from DE-A 103 03 589)
(1-12) 3-trifluoromethyl)-5-chloro-1-methyl-N-[2-(1,3,3-trimethylbutyl)phenyl]-1H-pyrazole-4-carboxamide (known from JP-A 10-251240)
(1-13) N-[2-(1,3-dimethylbutyl)phenyl]-2-iodobenzamide (known from DE-A 102 29 595)
(1-14) 2-iodo-N-[2-(1,3,3-trimethylbutyl)phenyl]benzamide (known from DE-A 102 29 595)

(1-15) N-[2-(1,3-dimethylbutyl)phenyl]-2-(trifluoromethyl) benzamide (known from DE-A 102 29 595)

(1-16) 2-(trifluoromethyl)-N-[2-(1,3,3-trimethylbutyl)phenyl]benzamide (known from DE-A 102 29 595)

Emphasis is given to active compound combinations according to the invention which, in addition to the carboxamide (1-8) 5-fluoro-1,3-dimethyl-N-[2-(1,3,3-trimethylbutyl)phenyl]-1H-pyrazole-4-carboxamide (group 1) contain one or more, preferably one, mixing partner of groups (2) to (24).

Emphasis is given to active compound combinations according to the invention which, in addition to the carboxamide (1-2) N-[2-(1,3-dimethylbutyl)phenyl]-5-fluoro-1,3-dimethyl-1H-pyrazole-4-carboxamide (group 1) contain one or more, preferably one, mixing partner of groups (2) to (24).

Emphasis is given to active compound combinations according to the invention which, in addition to the carboxamide (1-15) N-[2-(1,3-dimethylbutyl)phenyl]-2-trifluoromethyl)benzamide (group 1) contain one or more, preferably one, mixing partner of groups (2) to (24).

Emphasis is given to active compound combinations according to the invention which, in addition to the carboxamide (1-13) N-[2-(1,3-dimethylbutyl)phenyl]-2-iodobenzamide (group 1) contain one or more, preferably one, mixing partner of groups (2) to (24).

The formula (II) embraces the following preferred mixing partners of group (2):

(2-1) azoxystrobin (known from EP-A 0 382 375) of the formula

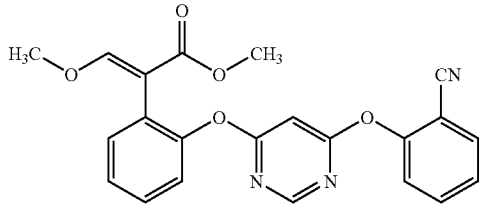 [SMILES: CO/C=C(/C(=O)OC)c1ccccc1Oc1cc(Oc2ccccc2C#N)ncn1]

(2-2) fluoxastrobin (known from DE-A 196 02 095) of the formula

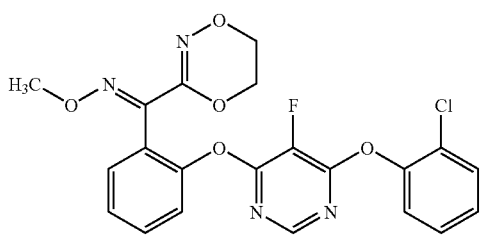 [SMILES: CO/N=C(/C1=NOCCO1)c1ccccc1Oc1ncnc(Oc2ccccc2Cl)c1F]

(2-3) (2E)-2-(2-{[6-(3-chloro-2-methylphenoxy)-5-fluoro-4-pyrimidinyl]oxy}phenyl)$_2$-methoxyimino)-N-methyl-ethanamide (known from DE-A 196 46 407, EP-B 0 712 396) of the formula

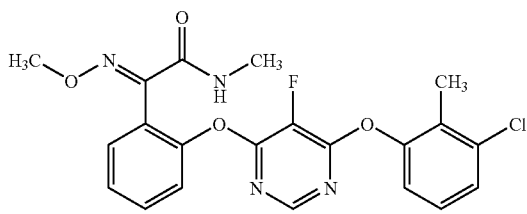 [SMILES: CNC(=O)/C(=N/OC)c1ccccc1Oc1ncnc(Oc2cccc(Cl)c2C)c1F]

(2-4) trifloxystrobin (known from EP-A 0 460 575) of the formula

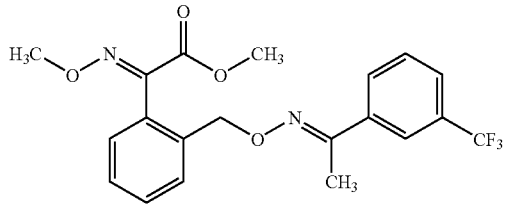 [SMILES: CO/N=C(/C(=O)OC)c1ccccc1CO/N=C(\C)c1cccc(C(F)(F)F)c1]

(2-5) (2E)-2-methoxyimino)-N-methyl-2-(2-{[({(1E)-1-[3-(trifluoromethyl)phenyl]ethyliden}-amino)oxy] methyl}phenyl)ethanamide (known from EP-A 0 569 384) of the formula

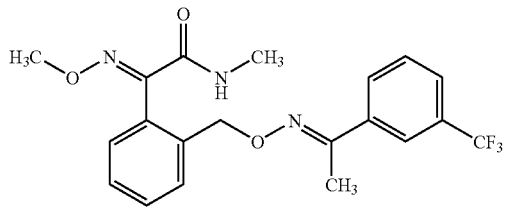 [SMILES: CNC(=O)/C(=N/OC)c1ccccc1CO/N=C(\C)c1cccc(C(F)(F)F)c1]

(2-6) (2E)-2-methoxyimino-N-methyl-2-{2-[(E)-({1-[3-(trifluoromethyl)phenyl)ethoxy}imino]methyl] phenyl}ethanamide (known from EP-A 0 596 254) of the formula

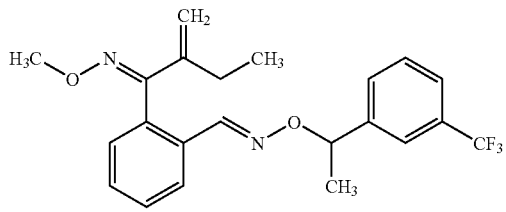 [SMILES: C=C(CC)/C(=N/OC)c1ccccc1/C=N/OC(C)c1cccc(C(F)(F)F)c1]

(2-7) orysastrobin (known from DE-A 195 39 324) of the formula

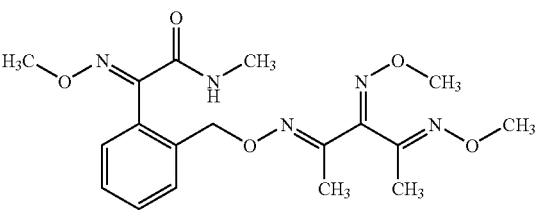

(2-8) 5-methoxy-2-methyl-4-(2-{[({(1E)-1-[3-trifluoromethyl)phenyl]ethyliden}amino)oxy]-methyl}phenyl)-2,4-dihydro-3H-1,2,4-triazol-3-one (known from WO 98/23155) of the formula

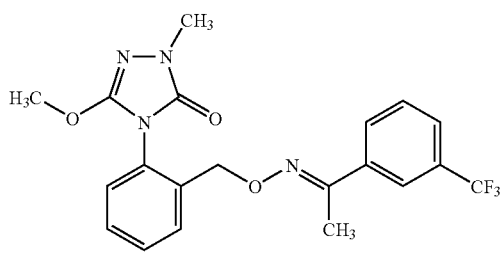 [SMILES: COc1nn(C)c(=O)n1-c1ccccc1CO/N=C(\C)c1cccc(C(F)(F)F)c1]

(2-9) kresoxim-methyl (known from EP-A 0 253 213) of the formula

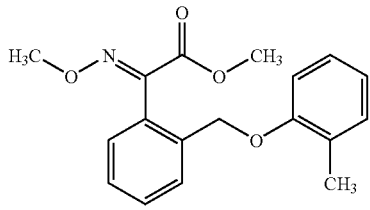 [SMILES: CO/N=C(/C(=O)OC)c1ccccc1COc1ccccc1C]

(2-10) dimoxystrobin (known from EP-A 0 398 692) of the formula

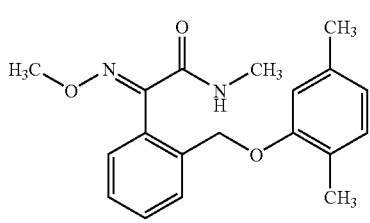 [SMILES: CNC(=O)/C(=N/OC)c1ccccc1COc1cc(C)ccc1C]

(2-11) picoxystrobin (known from EP-A 0 278 595) of the formula

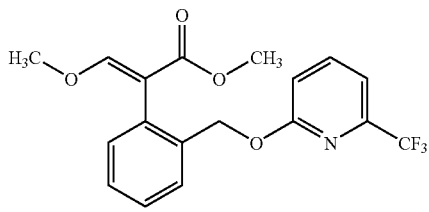 [SMILES: CO/C=C(/C(=O)OC)c1ccccc1COc1cccc(C(F)(F)F)n1]

(2-12) pyraclostrobin (known from DE-A 44 23 612) of the formula

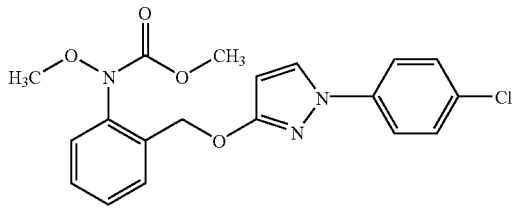

(2-13) metominostrobin (known from EP-A 0 398 692) of the formula

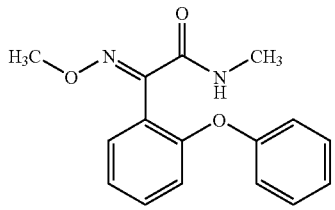

The formula (III) embraces the following preferred mixing partners of group (3):

(3-1) azaconazole (known from DE-A 25 51 560) of the formula

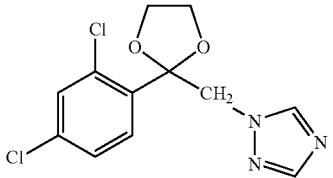 [SMILES: Clc1ccc(C2(Cn3cncn3)OCCO2)c(Cl)c1]

(3-2) etaconazole (known from DE-A 25 51 560) of the formula

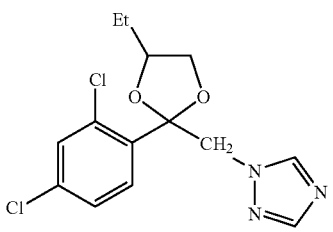 [SMILES: CCC1COC(Cn2cncn2)(c2ccc(Cl)cc2Cl)O1]

(3-3) propiconazole (known from DE-A 25 51 560) of the formula

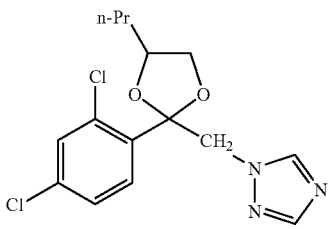

(3-4) difenoconazole (known from EP-A 0 112 284) of the formula

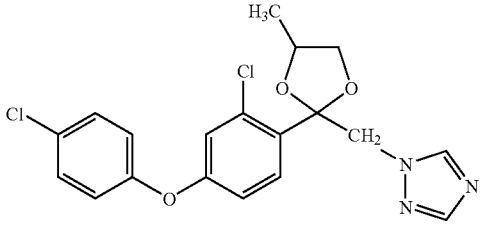 [SMILES: CC1COC(Cn2cncn2)(c2ccc(Oc3ccc(Cl)cc3)cc2Cl)O1]

(3-5) bromuconazole (known from EP-A 0 258 161) of the formula

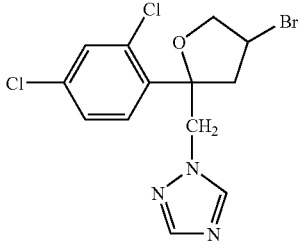 [SMILES: Clc1ccc(C2(Cn3cncn3)CC(Br)CO2)c(Cl)c1]

(3-6) cyproconazole (known from DE-A 34 06 993) of the formula

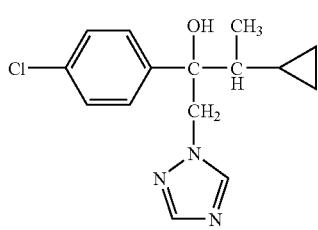 [SMILES: CC(C1CC1)C(O)(Cn1cncn1)c1ccc(Cl)cc1]

(3-7) hexaconazole (known from DE-A 30 42 303) of the formula

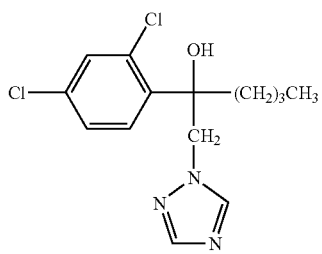

(3-8) penconazole (known from DE-A 27 35 872) of the formula

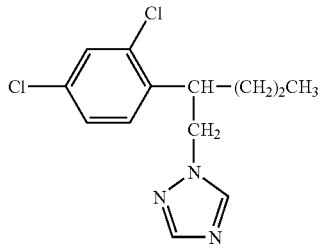

(3-9) myclobutanil (known from EP-A 0 145 294) of the formula

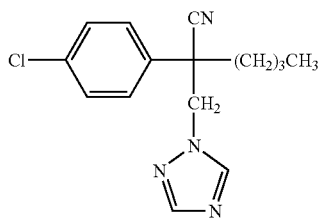

(3-10) tetraconazole (known from EP-A 0 234 242) of the formula

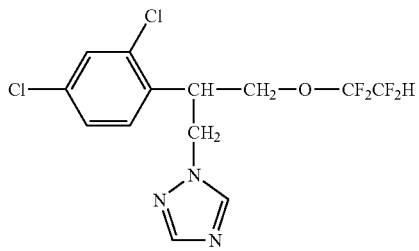

(3-11) flutriafol (known from EP-A 0 015 756) of the formula

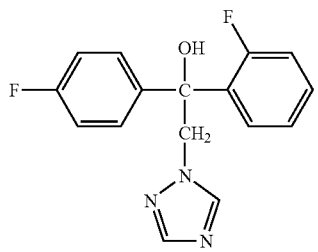 [SMILES: OC(Cn1cncn1)(c1ccc(F)cc1)c1ccccc1F]

(3-12) epoxiconazole (known from EP-A 0 196 038) of the formula

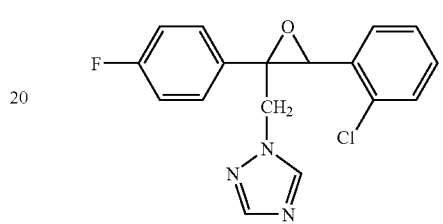

(3-13) flusilazole (known from EP-A 0 068 813) of the formula

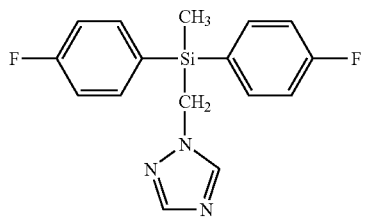 [SMILES: C[Si](Cn1cncn1)(c1ccc(F)cc1)c1ccc(F)cc1]

(3-14) simeconazole (known from EP-A 0 537 957) of the formula

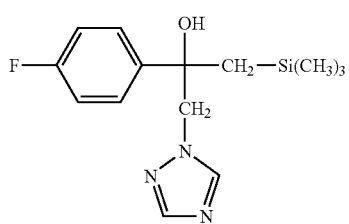

(3-15) prothioconazole (known from WO 96/16048) of the formula

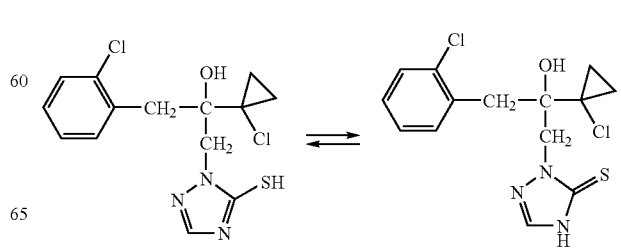

(3-16) fenbuconazole (known from DE-A 37 21 786) of the formula

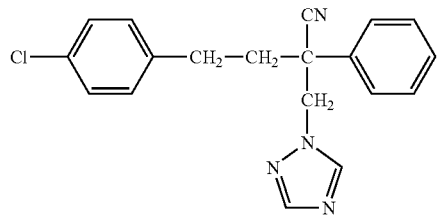

(3-17) tebuconazole (known from EP-A 0 040 345) of the formula

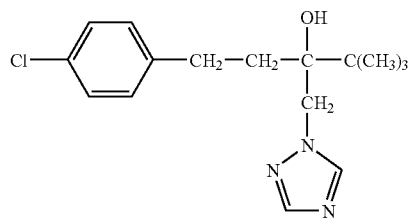 [SMILES: CC(C)(C)C(O)(CCc1ccc(Cl)cc1)Cn1cncn1]

(3-18) ipconazole (known from EP-A 0 329 397) of the formula

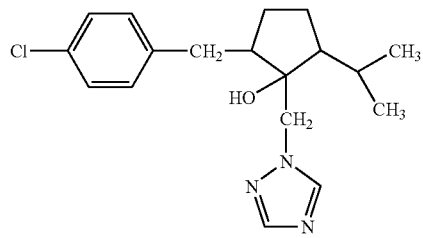 [SMILES: CC(C)C1CCC(Cc2ccc(Cl)cc2)C1(O)Cn1cncn1]

(3-19) metconazole (known from EP-A 0 329 397) of the formula

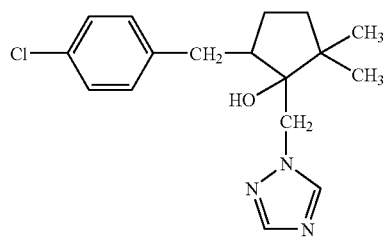 [SMILES: CC1(C)CCC(Cc2ccc(Cl)cc2)C1(O)Cn1cncn1]

(3-20) triticonazole (known from EP-A 0 378 953) of the formula

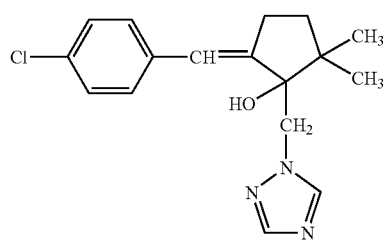 [SMILES: CC1(C)CCC(=Cc2ccc(Cl)cc2)C1(O)Cn1cncn1]

(3-21) bitertanol (known from DE-A 23 24 010) of the formula

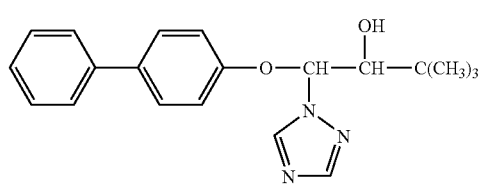

(3-22) triadimenol (known from DE-A 23 24 010) of the formula

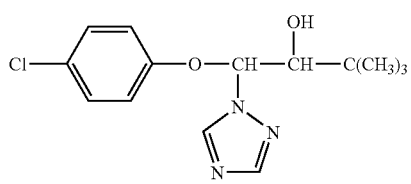 [SMILES: CC(C)(C)C(O)C(Oc1ccc(Cl)cc1)n1cncn1]

(3-23) triadimefon (known from DE-A 22 01 063) of the formula

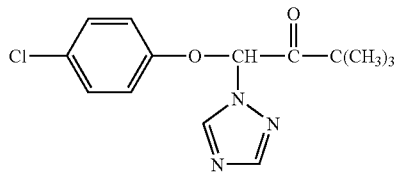 [SMILES: CC(C)(C)C(=O)C(Oc1ccc(Cl)cc1)n1cncn1]

(3-24) fluquinconazole (known from EP-A 0 183 458) of the formula

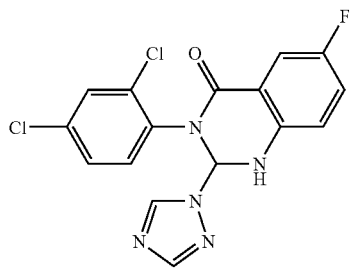 [SMILES: O=C1c2cc(F)ccc2NC(n2cncn2)N1c1ccc(Cl)cc1Cl]

(3-25) quinconazole (known from EP-A 0 183 458) of the formula

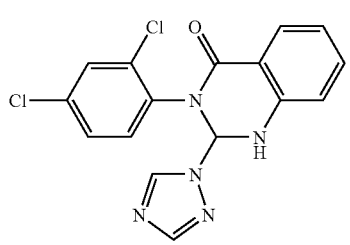 [SMILES: O=C1c2ccccc2NC(n2cncn2)N1c1ccc(Cl)cc1Cl]

The formula (IV) embraces the following preferred mixing partners of group (4):

(4-1) dichlofluanid (known from DE-A 11 93 498) of the formula

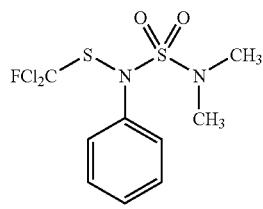

(4-2) tolylfluanid (known from DE-A 11 93 498) of the formula

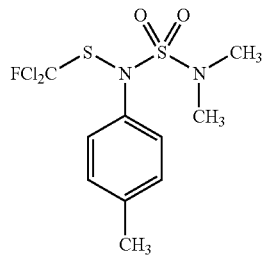

Preferred mixing partners of group (5) are (5-1) iprovalicarb (known from DE-A 40 26 966) of the formula

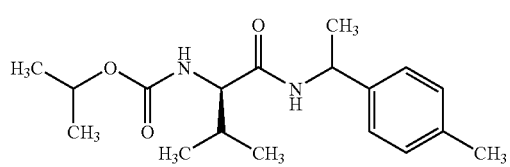 [SMILES: Cc1ccc(C(C)NC(=O)[C@H](NC(=O)OC(C)C)C(C)C)cc1]

(5-3) benthiavalicarb (known from WO 96/04252) of the formula

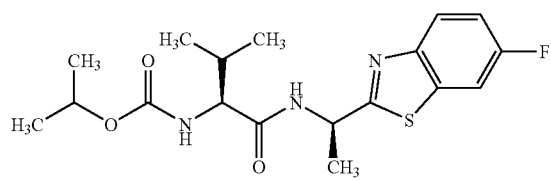 [SMILES: CC(C)OC(=O)N[C@H](C(=O)N[C@H](C)c1nc2ccc(F)cc2s1)C(C)C]

The formula (V) embraces the following preferred mixing partners of group (6):

(6-1) 2-chloro-N-(1,1,3-trimethylindan-4-yl)nicotinamide (known from EP-A 0 256 503) of the formula

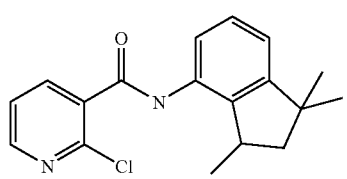 [SMILES: CC1CC(C)(C)c2cccc(NC(=O)c3cccnc3Cl)c21]

(6-2) boscalid (known from DE-A 195 31 813) of the formula

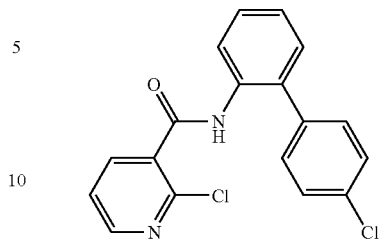

(6-3) furametpyr (known from EP-A 0 315 502) of the formula

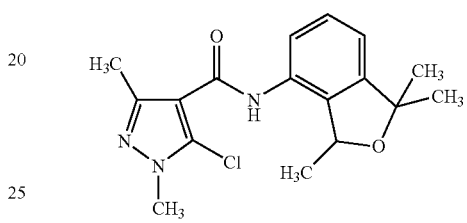

(6-4) N-(3-p-tolylthiophen-2-yl)-1-methyl-3-trifluoromethyl-1H-pyrazole-4-carboxamide (known from EP-A 0 737 682) of the formula

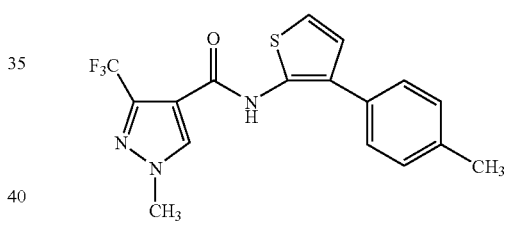

(6-5) ethaboxam (known from EP-A 0 639 574) of the formula

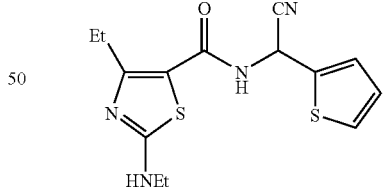

(6-6) fenhexamid (known from EP-A 0 339 418) of the formula

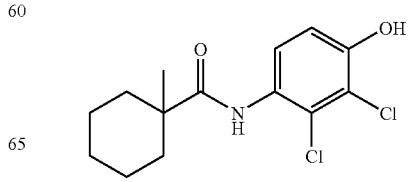

(6-7) carpropamid (known from EP-A 0 341 475) of the formula

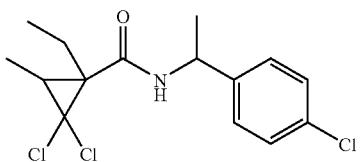 [SMILES: CCC1(C(=O)NC(C)c2ccc(Cl)cc2)C(C)C1(Cl)Cl]

(6-8) 2-chloro-4-(2-fluoro-2-methylpropionylamino)-N,N-dimethylbenzamide (known from EP-A 0 600 629) of the formula

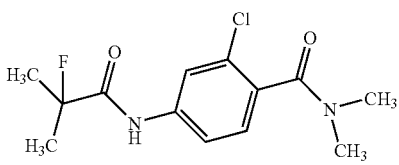 [SMILES: CN(C)C(=O)c1ccc(NC(=O)C(C)(C)F)cc1Cl]

(6-9) picobenzamid (known from WO 99/42447) of the formula

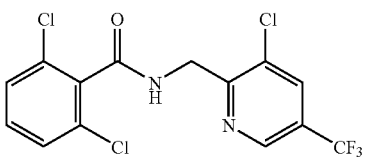 [SMILES: O=C(NCc1ncc(C(F)(F)F)cc1Cl)c1c(Cl)cccc1Cl]

(6-10) zoxamide (known from EP-A 0 604 019) of the formula

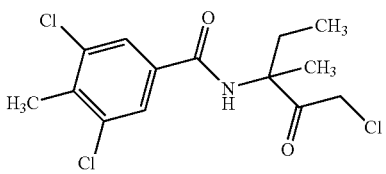 [SMILES: CCC(C)(NC(=O)c1cc(Cl)c(C)c(Cl)c1)C(=O)CCl]

(6-11) 3,4-dichloro-N-(2-cyanophenyl)isothiazole-5-carboxamide (known from WO 99/24413) of the formula

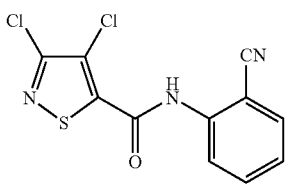 [SMILES: N#Cc1ccccc1NC(=O)c1snc(Cl)c1Cl]

(6-12) carboxin (known from U.S. Pat. No. 3,249,499) of the formula

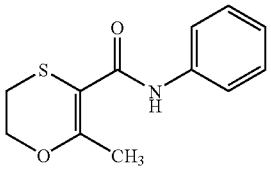 [SMILES: CC1=C(C(=O)Nc2ccccc2)SCCO1]

(6-13) tiadinil of the formula

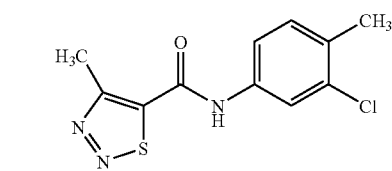 [SMILES: Cc1ccc(NC(=O)c2snnc2C)cc1Cl]

(6-14) penthiopyrad (known from EP-A 0 737 682) of the formula

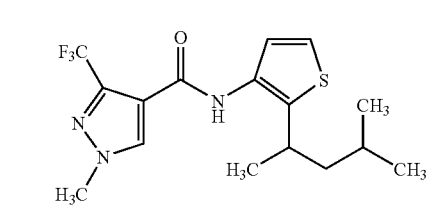 [SMILES: CC(C)CC(C)c1sccc1NC(=O)c1cn(C)nc1C(F)(F)F]

(6-15) silthiofam (known from WO 96/18631) of the formula

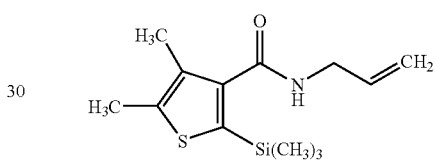

(6-16) N-[2-(1,3-dimethylbutyl)phenyl]-1-methyl-4-(trifluoromethyl)-1H-pyrrole-3-carboxamide (known from WO 02/38542) of the formula

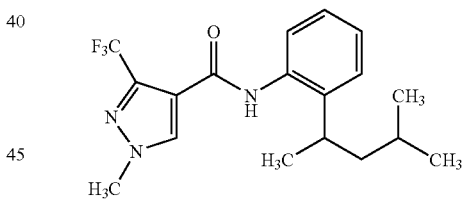

Preferred mixing partners of group (7) are (7-1) mancozeb (known from DE-A 12 34 704) having the IUPAC name manganese ethylenebis(dithiocarbamate) (polymeric) complex with zinc salt (7-2) maneb (known from U.S. Pat. No. 2,504,404) of the formula

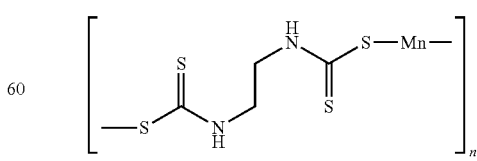

(7-3) metiram (known from DE-A 10 76 434) having the IUPAC name zinc ammoniate ethylenebis(dithiocarbamate)-poly(ethylenethiuram disulphide)

(7-4) propineb (known from GB 935 981) of the formula

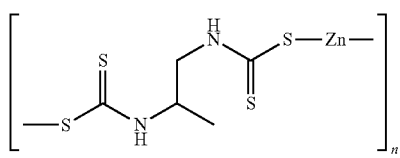

(7-5) thiram (known from U.S. Pat. No. 1,972,961) of the formula

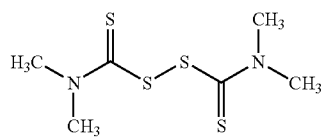

(7-6) zineb (known from DE-A 10 81 446) of the formula

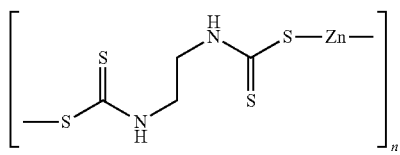

(7-7) ziram (known from U.S. Pat. No. 2,588,428) of the formula

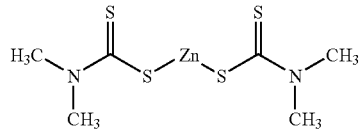

The formula (VI) embraces the following preferred mixing partners of group (8):

(8-1) benalaxyl (known from DE-A 29 03 612) of the formula

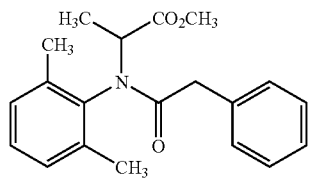 [SMILES: COC(=O)C(C)N(C(=O)Cc1ccccc1)c1c(C)cccc1C]

(8-2) furalaxyl (known from DE-A 25 13 732) of the formula

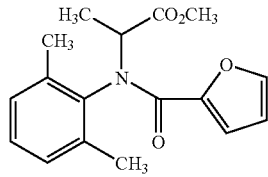 [SMILES: COC(=O)C(C)N(C(=O)c1ccco1)c1c(C)cccc1C]

(8-3) metalaxyl (known from DE-A 25 15 091) of the formula

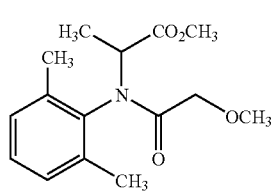 [SMILES: COCC(=O)N(c1c(C)cccc1C)C(C)C(=O)OC]

(8-4) metalaxyl-M (known from WO 96/01559) of the formula

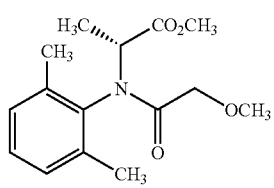 [SMILES: COCC(=O)N(c1c(C)cccc1C)[C@H](C)C(=O)OC]

(8-5) benalaxyl-M of the formula

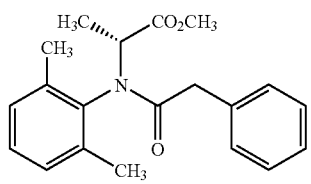 [SMILES: COC(=O)[C@@H](C)N(C(=O)Cc1ccccc1)c1c(C)cccc1C]

The formula (VII) embraces the following preferred mixing partners of group (9):

(9-1) cyprodinil (known from EP-A 0 310 550) of the formula

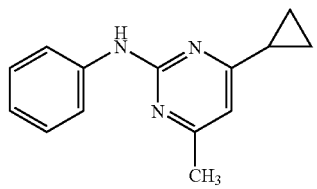 [SMILES: Cc1cc(C2CC2)nc(Nc2ccccc2)n1]

(9-2) mepanipyrim (known from EP-A 0 270 111) of the formula

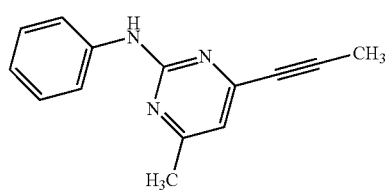 [SMILES: CC#Cc1cc(C)nc(Nc2ccccc2)n1]

(9-3) pyrimethanil (known from DD 151 404) of the formula

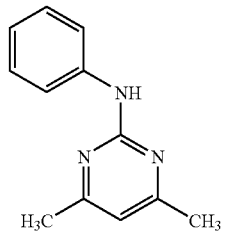

The formula (VIII) embraces the following preferred mixing partners of group (10):

(10-1) 6-chloro-5-[(3,5-dimethylisoxazol-4-yl)sulphonyl]-2,2-difluoro-5H-[1,3]dioxolo[4,5-f]-benzimidazole (known from WO 97/06171) of the formula

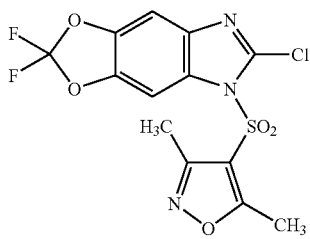 [SMILES: Cc1noc(C)c1S(=O)(=O)n1c(Cl)nc2cc3c(cc21)OC(F)(F)O3]

(10-2) benomyl (known from U.S. Pat. No. 3,631,176) of the formula

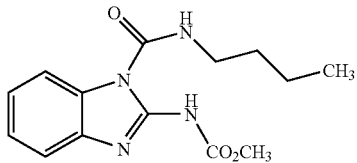

(10-3) carbendazim (known from U.S. Pat. No. 3,010,968) of the formula

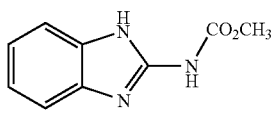

(10-4) chlorfenazole of the formula

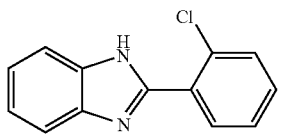

(10-5) fuberidazole (known from DE-A 12 09 799) of the formula

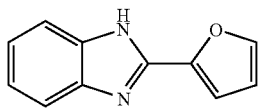 [SMILES: c1coc(-c2nc3ccccc3[nH]2)c1]

(10-6) thiabendazole (known from U.S. Pat. No. 3,206,468) of the formula

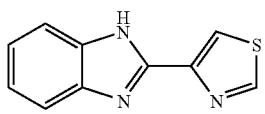

The formula (IX) embraces the following preferred mixing partners of group (11):

(11-1) diethofencarb (known from EP-A 0 078 663) of the formula

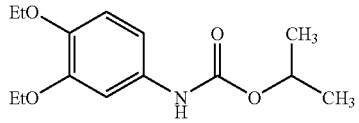 [SMILES: CCOc1ccc(NC(=O)OC(C)C)cc1OCC]

(11-2) propamocarb (known from U.S. Pat. No. 3,513,241) of the formula

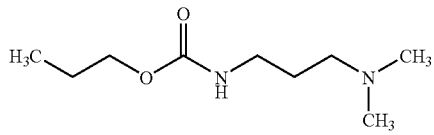

(11-3) propamocarb-hydrochloride (known from U.S. Pat. No. 3,513,241) of the formula

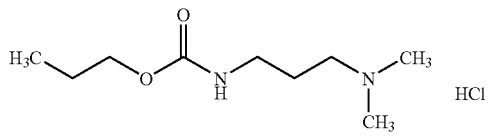

(11-4) propamocarb-fosetyl of the formula

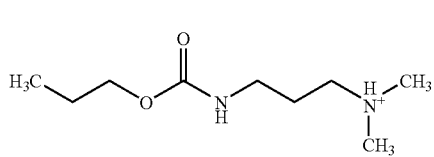

Preferred mixing partners of group (12) are (12-1) captafol (known from U.S. Pat. No. 3,178,447) of the formula

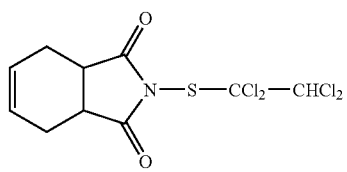

(12-2) captan (known from U.S. Pat. No. 2,553,770) of the formula

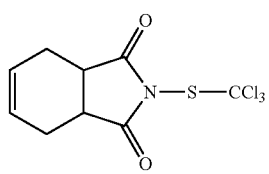

(12-3) folpet (known from U.S. Pat. No. 2,553,770) of the formula

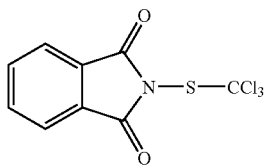

(12-4) iprodione (known from DE-A 21 49 923) of the formula

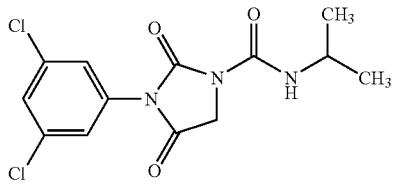 [SMILES: CC(C)NC(=O)N1CC(=O)N(c2cc(Cl)cc(Cl)c2)C1=O]

(12-5) procymidone (known from DE-A 20 12 656) of the formula

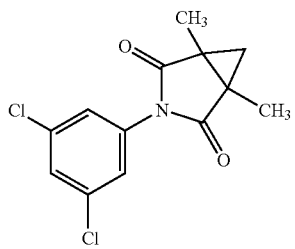 [SMILES: CC12CC1(C)C(=O)N(c1cc(Cl)cc(Cl)c1)C2=O]

(12-6) vinclozolin (known from DE-A 22 07 576) of the formula

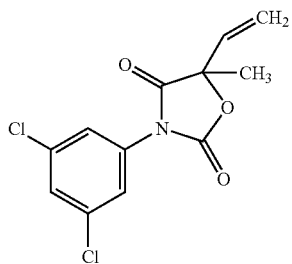 [SMILES: C=CC1(C)OC(=O)N(c2cc(Cl)cc(Cl)c2)C1=O]

Preferred mixing partners of group (13) are
(13-1) dodine (known from GB 11 03 989) of the formula

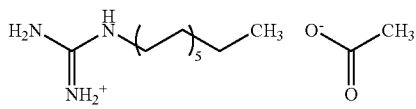

(13-2) guazatine (known from GB 11 14 155)
(13-3) iminoctadine triacetate (known from EP-A 0 155 509) of the formula

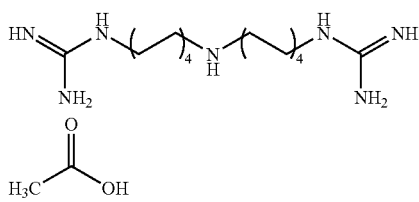

Preferred mixing partners of group (14) are
(14-1) cyazofamid (known from EP-A 0 298 196) of the formula

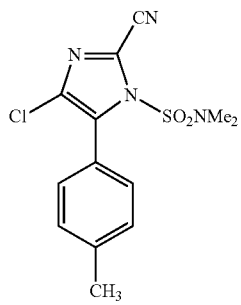

(14-2) prochloraz (known from DE-A 24 29 523) of the formula

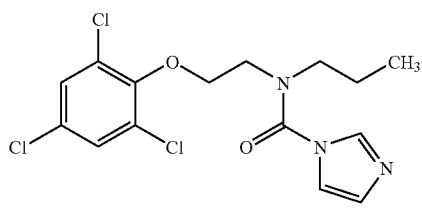 [SMILES: CCCN(CCOc1c(Cl)cc(Cl)cc1Cl)C(=O)n1ccnc1]

(14-3) triazoxide (known from DE-A 28 02 488) of the formula

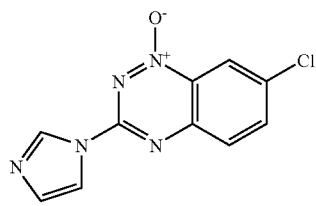 [SMILES: [O-][n+]1nc(-n2ccnc2)nc2ccc(Cl)cc21]

(14-4) pefurazoate (known from EP-A 0 248 086) of the formula

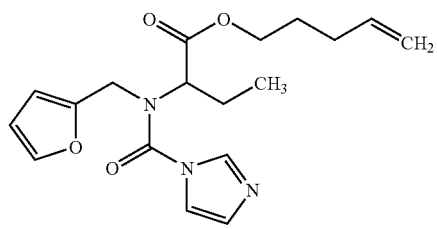 [SMILES: C=CCCCOC(=O)C(CC)N(Cc1ccco1)C(=O)n1ccnc1]

The formula (X) embraces the following preferred mixing partners of group (15):
(15-1) aldimorph (known from DD 140 041) of the formula

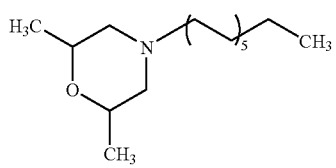

(15-2) tridemorph (known from GB 988 630) of the formula

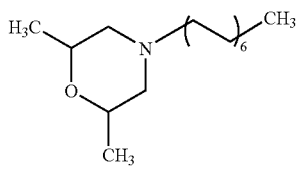

(15-3) dodemorph (known from DE-A 25 432 79) of the formula

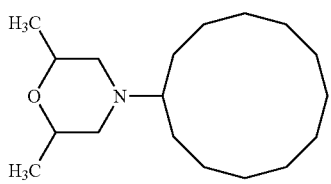

(15-4) fenpropimorph (known from DE-A 26 56 747) of the formula

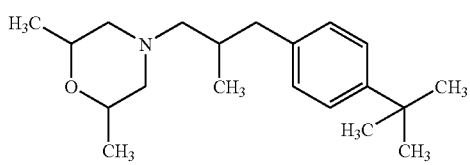 [SMILES: CC(Cc1ccc(C(C)(C)C)cc1)CN1CC(C)OC(C)C1]

(15-5) dimethomorph (known from EP-A 0 219 756) of the formula

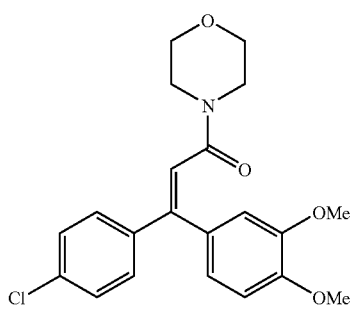 [SMILES: COc1ccc(/C(=C\C(=O)N2CCOCC2)c2ccc(Cl)cc2)cc1OC]

The formula (XI) embraces the following preferred mixing partners of group (16):

(16-1) fenpiclonil (known from EP-A 0 236 272) of the formula

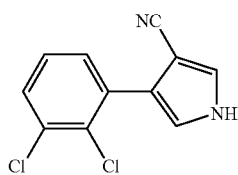

(16-2) fludioxonil (known from EP-A 0 206 999) of the formula

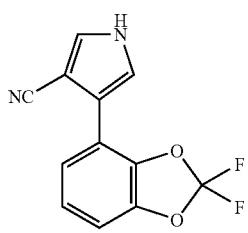

(16-3) pyrrolnitrin of the formula

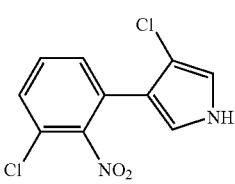 [SMILES: O=[N+]([O-])c1c(Cl)cccc1-c1c[nH]cc1Cl]

Preferred mixing partners of group (17) are (17-1) fosetyl-Al (known from DE-A 24 56 627) of the formula

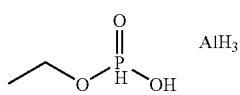

(17-2) phosphonic acid (known chemical) of the formula

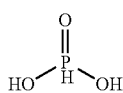

The formula (XII) embraces the following preferred mixing partners of group (18) which are known from WO 96/23793 and can in each case be present as E or Z isomers. Accordingly, compounds of the formula (XII) can be present as a mixture of different isomers or else in the form of a single isomer. Preference is given to compounds of the formula (XII) in the form of their E isomers:

(18-1) the compound 2-(2,3-dihydro-1H-inden-5-yl)-N-[2-(3,4-dimethoxyphenyl)ethyl]-2-(methoxyimino)acetamide of the formula

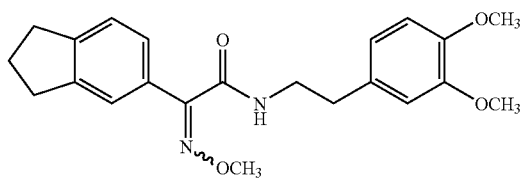 [SMILES: CON=C(C(=O)NCCc1ccc(OC)c(OC)c1)c1ccc2c(c1)CCC2]

(18-2) the compound N-[2-(3,4-dimethoxyphenyl)ethyl]-2-(methoxyimino)-2-(5,6,7,8-tetrahydro-naphthalen-2-yl)acetamide of the formula

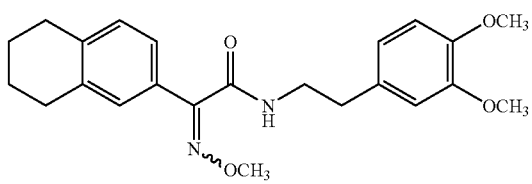 [SMILES: CON=C(C(=O)NCCc1ccc(OC)c(OC)c1)c1ccc2c(c1)CCCC2]

(18-3) the compound 2-(4-chlorophenyl)-N-[2-(3,4-dimethoxyphenyl)ethyl]-2-(methoxyimino)-acetamide of the formula

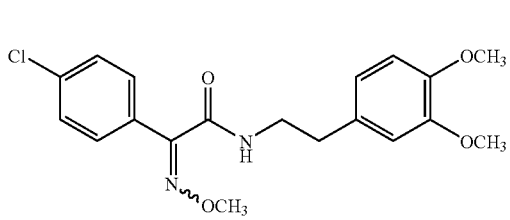 [SMILES: CON=C(C(=O)NCCc1ccc(OC)c(OC)c1)c1ccc(Cl)cc1]

(18-4) the compound 2-(4-bromophenyl)-N-[2-(3,4-dimethoxyphenyl)ethyl]-2-(methoxyimino)-acetamide of the formula

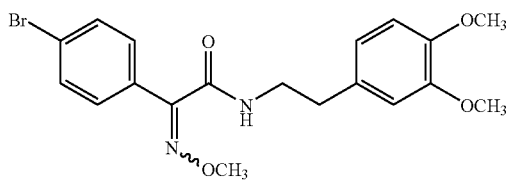

(18-5) the compound 2-(4-methylphenyl)-N-[2-(3,4-dimethoxyphenyl)ethyl]-2-methoxyimino)-acetamide of the formula

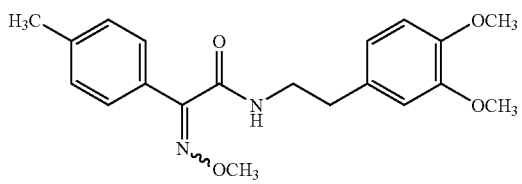 [SMILES: CON=C(C(=O)NCCc1ccc(OC)c(OC)c1)c1ccc(C)cc1]

(18-6) the compound 2-(4-ethylphenyl)-N-[2-(3,4-dimethoxyphenyl)ethyl]-2-(methoxyimino)-acetamide of the formula

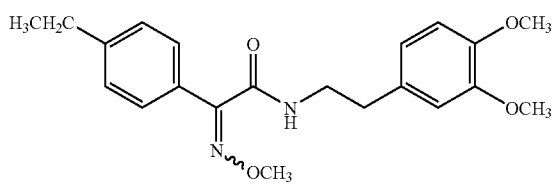

Preferred mixing partners of group (19) are (19-1) acibenzolar-S-methyl (known from EP-A 0 313 512) of the formula

(19-2) chlorothalonil (known from U.S. Pat. No. 3,290,353) of the formula

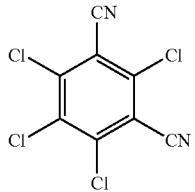 [SMILES: N#Cc1c(Cl)c(Cl)c(Cl)c(C#N)c1Cl]

(19-3) cymoxanil (known from DE-A 23 12 956) of the formula

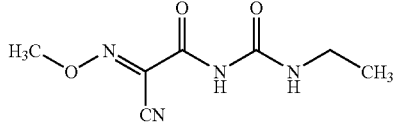

(19-4) edifenphos (known from DE-A 14 93 736) of the formula

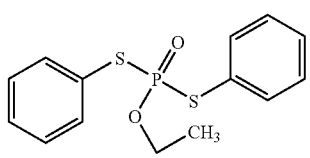 [SMILES: CCOP(=O)(Sc1ccccc1)Sc1ccccc1]

(19-5) famoxadone (known from EP-A 0 393 911) of the formula

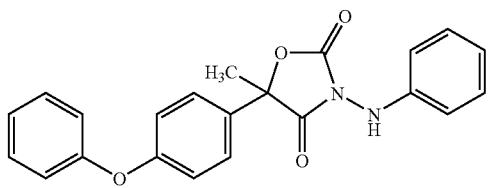 [SMILES: CC1(c2ccc(Oc3ccccc3)cc2)OC(=O)N(Nc2ccccc2)C1=O]

(19-6) fluazinam (known from EP-A 0 031 257) of the formula

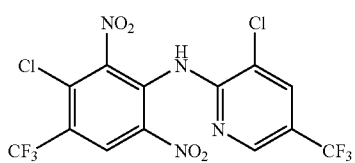

(19-7) copper oxychloride (19-9) oxadixyl (known from DE-A 30 30 026) of the formula

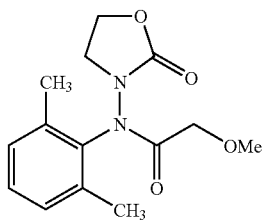 [SMILES: COCC(=O)N(c1c(C)cccc1C)N1CCOC1=O]

(19-10) spiroxamine (known from DE-A 37 35 555) of the formula

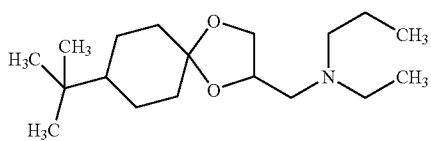 [SMILES: CCCN(CC)CC1COC2(CCC(C(C)(C)C)CC2)O1]

(19-11) dithianon (known from JP-A 44-29464) of the formula

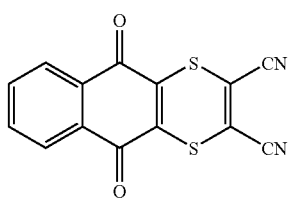 [SMILES: N#Cc1sc2c(=O)c3ccccc3c(=O)c=2sc1C#N]

(19-12) metrafenone (known from EP-A 0 897 904) of the formula

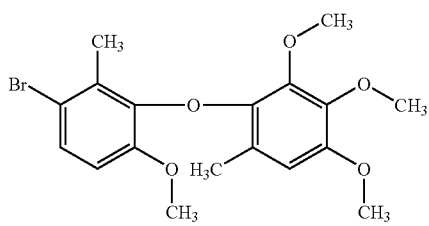 [SMILES: COc1ccc(Br)c(C)c1Oc1c(C)cc(OC)c(OC)c1OC]

(19-13) fenamidone (known from EP-A 0 629 616) of the formula

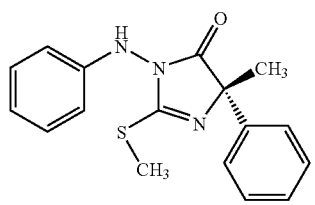 [SMILES: CSC1=N[C@@](C)(c2ccccc2)C(=O)N1Nc1ccccc1]

(19-14) 2,3-dibutyl-6-chlorothieno[2,3-d]pyrimidin-4(3H)one (known from WO 99/14202) of the formula

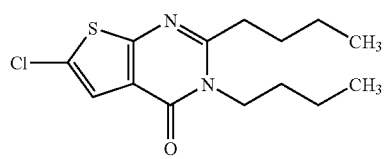 [SMILES: CCCCc1nc2sc(Cl)cc2c(=O)n1CCCC]

(19-15) probenazole (known from U.S. Pat. No. 3,629,428) of the formula

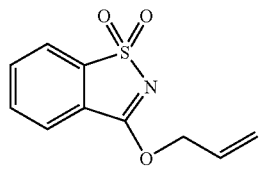

(19-16) isoprothiolane (known from U.S. Pat. No. 3,856,814) of the formula

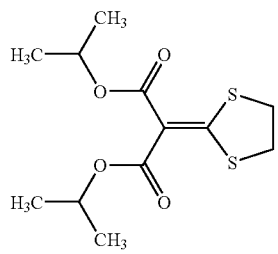 [SMILES: CC(C)OC(=O)C(C(=O)OC(C)C)=C1SCCS1]

(19-17) kasugamycin (known from GB 1 094 567) of the formula

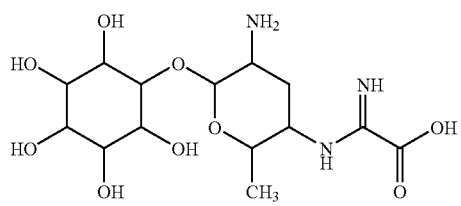 [SMILES: CC1OC(OC2C(O)C(O)C(O)C(O)C2O)C(N)CC1NC(=N)C(=O)O]

(19-18) phthalide (known from DE 1643347) of the formula

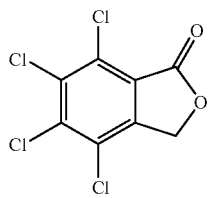 [SMILES: O=C1OCc2c(Cl)c(Cl)c(Cl)c(Cl)c21]

(19-19) ferimzone (known from EP-A 0 019 450) of the formula

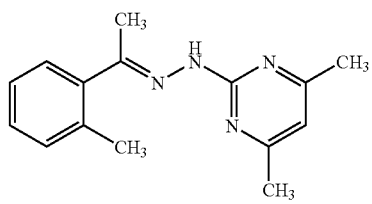 [SMILES: C/C(=N\Nc1nc(C)cc(C)n1)c1ccccc1C]

(19-20) tricyclazole (known from DE-A 22 50 077) of the formula

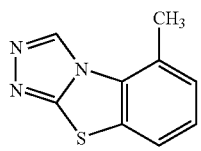

(19-21) N-({4-[(cyclopropylamino)carbonyl]phenyl}sulphonyl)-2-methoxybenzamide of the formula

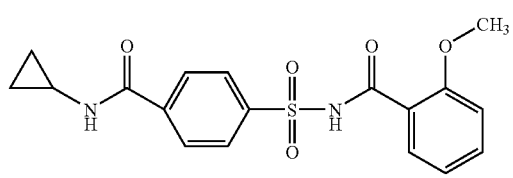 [SMILES: COc1ccccc1C(=O)NS(=O)(=O)c1ccc(C(=O)NC2CC2)cc1]

(19-22) 2-(4-chlorophenyl)-N-{2-[3-methoxy-4-prop-2-yn-1-yloxy)phenyl]ethyl}-2-prop-2-yn-1-yloxy)acetamide (known from WO 01/87822) of the formula

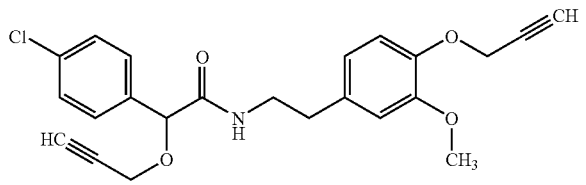 [SMILES: C#CCOc1ccc(CCNC(=O)C(OCC#C)c2ccc(Cl)cc2)cc1OC]

Preferred mixing partners of group (20) are (20-1) pencycuron (known from DE-A 27 32 257) of the formula

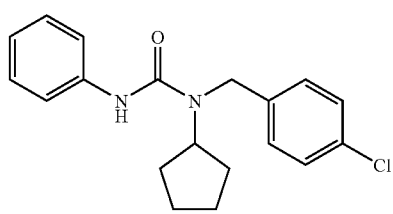 [SMILES: O=C(Nc1ccccc1)N(Cc1ccc(Cl)cc1)C1CCCC1]

(20-2) thiophanate-methyl (known from DE-A 18 06 123) of the formula

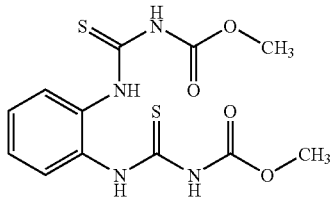 [SMILES: COC(=O)NC(=S)Nc1ccccc1NC(=S)NC(=O)OC]

(20-3) thiophanate-ethyl (known from DE-A 18 06 123) of the formula

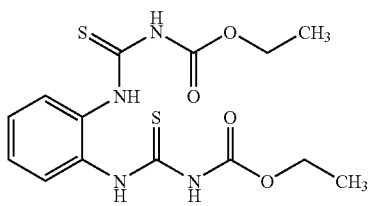 [SMILES: CCOC(=O)NC(=S)Nc1ccccc1NC(=S)NC(=O)OCC]

Preferred mixing partners of group (21) are (21-1) fenoxanil (known from EP-A 0 262 393) of the formula

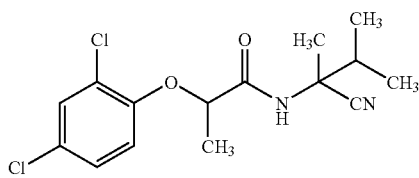 [SMILES: CC(Oc1ccc(Cl)cc1Cl)C(=O)NC(C)(C#N)C(C)C]

(21-2) diclocymet (known from JP-A 7-206608) of the formula

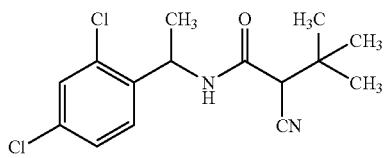 [SMILES: CC(NC(=O)C(C#N)C(C)(C)C)c1ccc(Cl)cc1Cl]

Preferred mixing partners of group (22) are (22-1) 5-chloro-N-[(1S)-2,2,2-trifluoro-1-methylethyl]-6-(2,4,6-trifluorophenyl)[1,2,4]triazolo-[1,5-a]pyrimidine-7-amine (known from U.S. Pat. No. 5,986,135) of the formula

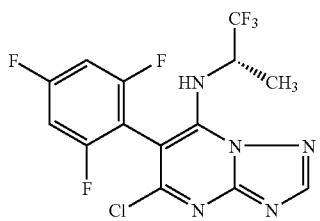 [SMILES: C[C@H](Nc1c(-c2c(F)cc(F)cc2F)c(Cl)nc2ncnn12)C(F)(F)F]

(22-2) 5-chloro-N-[(1R)-1,2-dimethylpropyl]-6-(2,4,6-trifluorophenyl)[1,2,4]triazolo[1,5-a]-pyrimidine-7-amine (known from WO 02/38565) of the formula

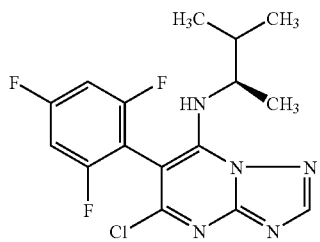 [SMILES: CC(C)[C@@H](C)Nc1c(-c2c(F)cc(F)cc2F)c(Cl)nc2ncnn12]

(22-3) 5-chloro-6-(2-chloro-6-fluorophenyl)-7-(4-methylpiperidin-1-yl)[1,2,4]triazolo[1,5-a]-pyrimidine (known from U.S. Pat. No. 5,593,996) of the formula

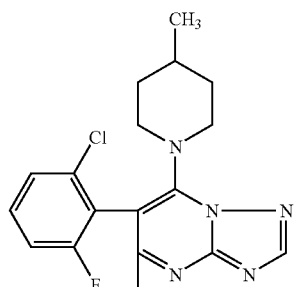

(22-4) 5-chloro-6-(2,4,6-trifluorophenyl)-7-(4-methylpiperidin-1-yl)[1,2,4]triazolo[1,5-a]pyrimidine (known from DE-A 101 24 208) of the formula

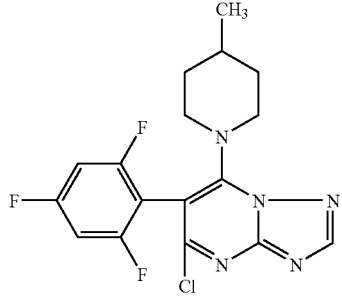 [SMILES: CC1CCN(c2c(-c3c(F)cc(F)cc3F)c(Cl)nc3ncnn23)CC1]

Preferred mixing partners of group (23) are (23-1) 2-butoxy-6-iodo-3-propylbenzopyran-4-one (known from WO 03/014103) of the formula

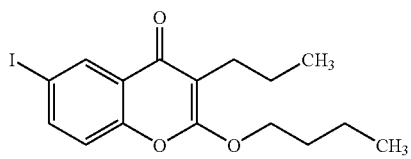 [SMILES: CCCCOc1oc2ccc(I)cc2c(=O)c1CCC]

(23-2) 2-ethoxy-6-iodo-3-propylbenzopyran-4-one (known from WO 03/014103) of the formula

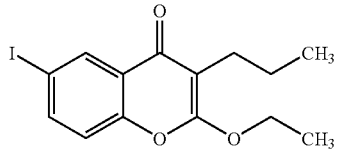 [SMILES: CCCc1c(OCC)oc2ccc(I)cc2c1=O]

(23-3) 6-iodo-2-propoxy-3-propylbenzopyran-4-one (known from WO 03/014103) of the formula

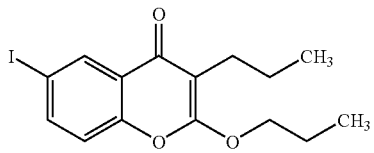

(23-4) 2-but-2-ynyloxy-6-iodo-3-propylbenzopyran-4-one (known from WO 03/014103) of the formula

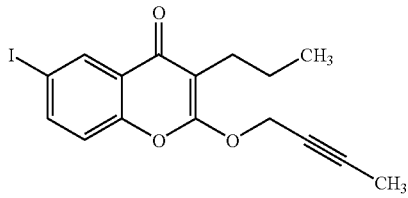 [SMILES: CC#CCOc1oc2ccc(I)cc2c(=O)c1CCC]

(23-5) 6-iodo-2-(1-methylbutoxy)-3-propylbenzopyran-4-one (known from WO 03/014103) of the formula

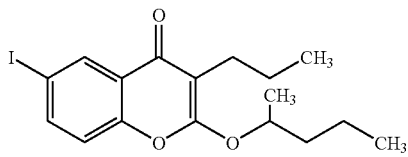 [SMILES: CCCc1c(OC(C)CCC)oc2ccc(I)cc2c1=O]

(23-6) 2-but-3-enyloxy-6-iodobenzopyran-4-one (known from WO 03/014103) of the formula

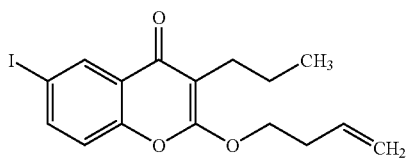 [SMILES: C=CCCOc1oc2ccc(I)cc2c(=O)c1CCC]

(23-7) 3-butyl-6-iodo-2-isopropoxybenzopyran-4-one (known from WO 03/014103) of the formula

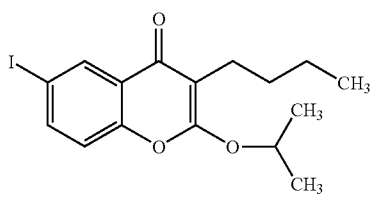 [SMILES: CCCCc1c(OC(C)C)oc2ccc(I)cc2c1=O]

Preferred mixing partners of group (24) are (24-1) N-(3',4'-dichloro-5-fluoro-1,1'-biphenyl-2-yl)-3-difluoromethyl)-1-methyl-1H-pyrazole-4-carboxamide (known from WO 03/070705) of the formula

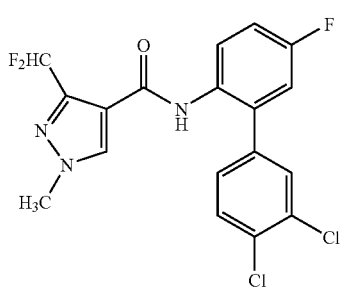 [SMILES: Cn1cc(C(=O)Nc2ccc(F)cc2-c2ccc(Cl)c(Cl)c2)c(C(F)F)n1]

(24-2) 3-difluoromethyl-N-{3'-fluoro-4'-[(E)-(methoxyimino)methyl]-1,1'-biphenyl-2-yl}-1-methyl-1H-pyrazole-4-carboxamide (known from WO 02/08197) of the formula

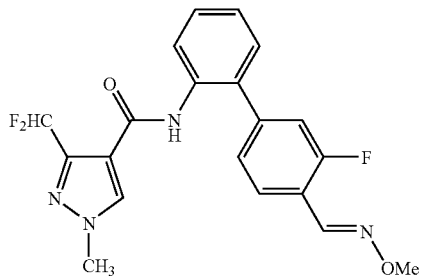 [SMILES: CO/N=C/c1ccc(-c2ccccc2NC(=O)c2cn(C)nc2C(F)F)cc1F]

(24-3) 3-(trifluoromethyl)-N-{3'-fluoro-4'-[(E)-(methoxyimino)methyl]-1,1'-biphenyl-2-yl}-1-methyl-1H-pyrazole-4-carboxamide (known from WO 02/08197) of the formula

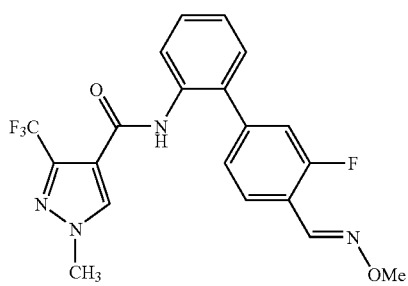 [SMILES: CO/N=C/c1ccc(-c2ccccc2NC(=O)c2cn(C)nc2C(F)(F)F)cc1F]

(24-4) N-(3',4'-dichloro-1,1'-biphenyl-2-yl)-5-fluoro-1,3-dimethyl-1H-pyrazole-4-carboxamide (known from WO 03/70705) of the formula

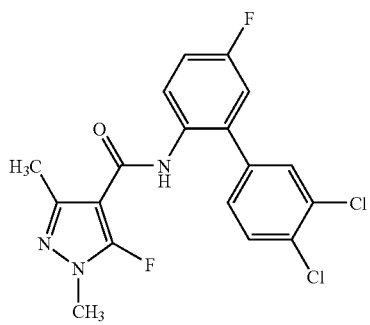 [SMILES: Cc1nn(C)c(F)c1C(=O)Nc1ccc(F)cc1-c1ccc(Cl)c(Cl)c1]

(24-5) N-(4'-chloro-3'-fluoro-1,1'-biphenyl-2-yl)-2-methyl-4-trifluoromethyl)-1,3-thiazole-5-carboxamide (known from WO 03/066609) of the formula

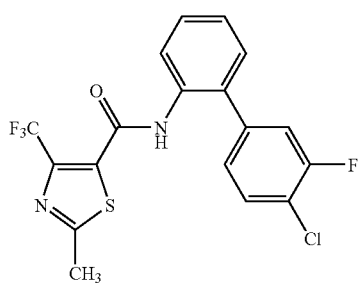 [SMILES: Cc1nc(C(F)(F)F)c(C(=O)Nc2ccccc2-c2ccc(Cl)c(F)c2)s1]

(24-6) N-(4'-chloro-1,1'-biphenyl-2-yl)-4-(difluoromethyl)-2-methyl-1,3-thiazole-5-carboxamide (known from WO 03/066610) of the formula

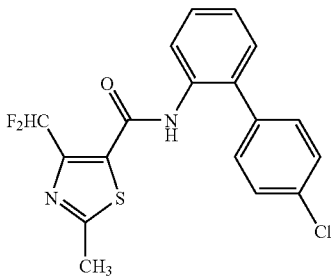 [SMILES: Cc1nc(C(F)F)c(C(=O)Nc2ccccc2-c2ccc(Br)cc2)s1]

(24-7) N-(4'-bromo-1,1'-biphenyl-2-yl)-4-(difluoromethyl)-2-methyl-1,3-thiazole-5-carboxamide (known from WO 03/066610) of the formula

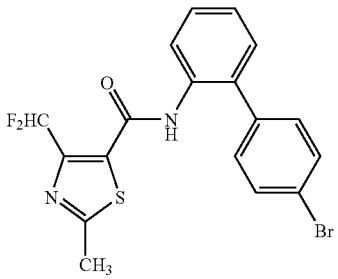

(24-8) 4-(difluoromethyl)-2-methyl-N-[4'-(trifluoromethyl)-1,1'-biphenyl-2-yl]-1,3-thiazole-5-carboxamide (known from WO 03/066610) of the formula

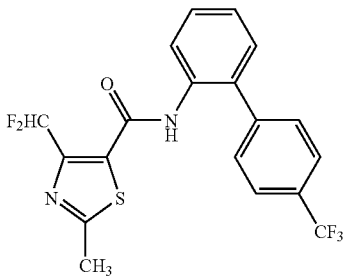 [SMILES: Cc1nc(C(F)F)c(C(=O)Nc2ccccc2-c2ccc(C(F)(F)F)cc2)s1]

Compound (6-7), carpropamid, has three asymmetrically substituted carbon atoms. Accordingly, compound (6-7) can be present as a mixture of different isomers or else in the form of a single component. Particular preference is given to the compounds (1S,3R)-2,2-dichloro-N-[(1R)-1-(4-chlorophenyl)ethyl]-1-ethyl-3-methylcyclopropanecarboxamide of the formula

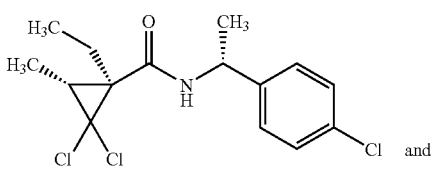 [SMILES: CC[C@@]1(C(=O)N[C@H](C)c2ccc(Cl)cc2)[C@@H](C)C1(Cl)Cl ; "and"]

and (1R,3S)-2,2-dichloro-N-[(1R)-1-(4-chlorophenyl)ethyl]-1-ethyl-3-methylcyclopropanecarboxamide of the formula

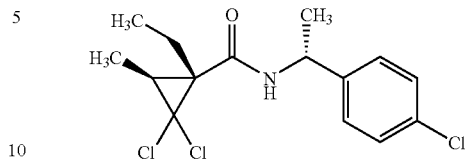

Particularly preferred mixing partners are the following active compounds:
(2-1) azoxystrobin
(2-2) fluoxastrobin
(2-3) (2E)-2-(2-{[6-(3-chloro-2-methylphenoxy)-5-fluoro-4-pyrimidinyl]oxy}phenyl)-2-(methoxyimino)-N-methylethanamide
(2-4) trifloxystrobin
(2-5) (2E)-2-(methoxyimino)-N-methyl-2-(2-{[({(1E)-1-[3-(trifluoromethyl)-phenyl]ethyliden}amino)oxy]methyl}phenyl)ethanamide
(2-6) (2E)-2-methoxyimino-N-methyl-2-{2-[(E)-({1-[3-(trifluoromethyl)phenyl]-ethoxy}imino)methyl]phenyl}ethanamide.
(2-8) 5-methoxy-2-methyl-4-{[({(1E)-1-[3-trifluoromethyl)phenyl]ethyliden}-amino)oxy]methyl}phenyl)-2,4-dihydro-3H-1,2,4-triazol-3-one
(2-11) picoxystrobin
(2-9) kresoxim-methyl
(2-10) dimoxystrobin
(2-12) pyraclostrobin
(2-13) metominostrobin
(3-3) propiconazole
(3-4) difenoconazole
(3-6) cyproconazole
(3-7) hexaconazole
(3-8) penconazole
(3-9) myclobutanil
(3-10) tetraconazole
(3-12) epoxiconazole
(3-13) flusilazole
(3-15) prothioconazole
(3-16) fenbuconazole
(3-17) tebuconazole
(3-19) metconazole
(3-21) bitertanol
(3-22) triadimenol
(3-23) triadimefon
(3-24) fluquinconazole
(4-1) dichlofluanid
(4-2) tolylfluanid
(5-1) iprovalicarb
(5-3) benthiavalicarb
(6-2) boscalid
(6-5) ethaboxam
(6-6) fenhexamid
(6-7) carpropamid
(6-8) 2-chloro-4-[(2-fluoro-2-methylpropanoyl)amino]-N,N-dimethylbenzamide
(6-9) picobenzamid
(6-10) zoxamide
(6-11) 3,4-dichloro-N-(2-cyanophenyl)isothiazole-5-carboxamide
(6-14) penthiopyrad
(6-16) N-[2-(1,3-dimethylbutyl)phenyl]-1-methyl-4-(trifluoromethyl) 1H-pyrrole-3-carboxamide (7-1) mancozeb
(7-2) maneb
(7-4) propineb
(7-5) thiram
(7-6) zineb
(8-1) benalaxyl
(8-2) furalaxyl
(8-3) metalaxyl
(8-4) metalaxyl M
(8-5) benalaxyl-M
(9-1) cyprodinil
(9-2) mepanipyrim
(9-3) pyrimethanil
(10-1) 6-chloro-5-[(3,5-dimethylisoxazol-4-yl)sulphonyl]-2,2-difluoro-5H-[1,3]dioxolo[4,5-f]-benzimidazole
(10-3) carbendazim
(11-1) diethofencarb
(11-2) propamocarb
(11-3) propamocarb-hydrochloride
(11-4) propamocarb-fosetyl
(12-2) captan
(12-3) folpet
(12-4) iprodione
(12-5) procymidone
(13-1) dodine
(13-2) guazatine
(13-3) iminoctadine triacetate
(14-1) cyazofamid
(14-2) prochloraz
(14-3) triazoxide
(15-5) dimethomorph
(15-4) fenpropimorph
(16-2) fludioxonil
(17-1) fosetyl-Al
(17-2) phosphonic acid
(19-1) acibenzolar-S-methyl
(19-2) chlorothalonil
(19-3) cymoxanil
(19-5) famoxadone
(19-6) fluazinam
(19-9) oxadixyl
(19-10) spiroxamine
(19-7) copper oxychloride
(19-13) fenamidone
(19-22) 2-(4-chlorophenyl)-N-{2-[3-methoxy-4-(prop-2-yn-1-yloxy)phenyl]ethyl}-2-(prop-2-yn-1-yloxy)acetamide
(20-1) pencycuron
(20-2) thiophanate-methyl
(22-1) 5-chloro-N-[(1S)-2,2,2-trifluoro-1-methylethyl]-6-(2,4,6-trifluorophenyl)[1,2,4]-triazolo[1,5-a]pyrimidine-7-amine
(22-2) 5-chloro-N-[(1R)-1,2-dimethylpropyl]-6-(2,4,6-trifluorophenyl)[1,2,4]triazolo[1,5-a]-pyrimidine-7-amine
(22-4) 5-chloro-6-(2,4,6-trifluorophenyl)-7-(4-methylpiperidin-1-yl)[1,2,4]triazolo[1,5-a]pyrimidine
(23-1) 2-butoxy-6-iodo-3-propylbenzopyran-4-one
(23-2) 2-ethoxy-6-iodo-3-propylbenzopyran-4-one
(23-3) 6-iodo-2-propoxy-3-propylbenzopyran-4-one
(24-1) N-(3',4'-dichloro-5-fluoro-1,1'-biphenyl-2-yl)-3-(difluoromethyl)-1-methyl-1H-pyrazole-4-carboxamide
(24-3) 3-(trifluoromethyl)-N-{3'-fluoro-4'-[(E)-(methoxyimino)methyl]-1,1'-biphenyl-2-yl}-1-methyl-1H-pyrazole-4-carboxamide
(24-7) N-(4'-bromo-1,1'-biphenyl-2-yl)-4-(difluoromethyl)-2-methyl-1,3-thiazole-5-carboxamide.

Very particularly preferred mixing partners are the following active compounds:
(2-2) fluoxastrobin
(2-4) trifloxystrobin
(2-3) (2E)-2-(2-{[6-(3-chloro-2-methylphenoxy-5-fluoro-4-pyrimidinyl]oxy}phenyl)-2-(methoxyimino)-N-methylethanamide
(3-15) prothioconazole
(3-17) tebuconazole
(3-21) bitertanol
(3-22) triadimenol
(3-24) fluquinconazole
(4-1) dichlofluanid
(4-2) tolylfluanid
(5-1) iprovalicarb
(6-6) fenhexamid
(6-9) picobenzamid
(6-7) carpropamid
(6-14) penthiopyrad
(7-4) propineb
(8-4) metalaxyl-M
(8-5) benalaxyl-M
(9-3) pyrimethanil
(10-3) carbendazim
(11-4) propamocarb-fosetyl
(12-4) iprodione
(14-2) prochloraz
(14-3) triazoxide
(16-2) fludioxonil
(19-10) spiroxamine
(19-22) 2-(4-chlorophenyl)-N-{2-[3-methoxy-4-(prop-2-yn-1-yloxy)phenyl]ethyl}-2-(prop-2-yn-1-yloxy)acetamide
(22-4) 5-chloro-6-(2,4,6-trifluorophenyl)-7-(4-methylpiperidin-1-yl)[1,2,4]triazolo[1,5-a]pyrimidine
(24-1) N-(3',4'-dichloro-5-fluoro-1,1'-biphenyl-2-yl)-3-(difluoromethyl)-1-methyl-1H-pyrazole-4-carboxamide.

Preferred active compound combinations comprising two groups of active compounds and in each case at least one carboxamide of the formula (I) (group 1) and at least one active compound of the given group (2) to (24) are described below. These combinations are the active compound combinations A to U.

Among the preferred active compound combinations A to U, emphasis is given to those comprising a carboxamide of the formula (I) (group 1)

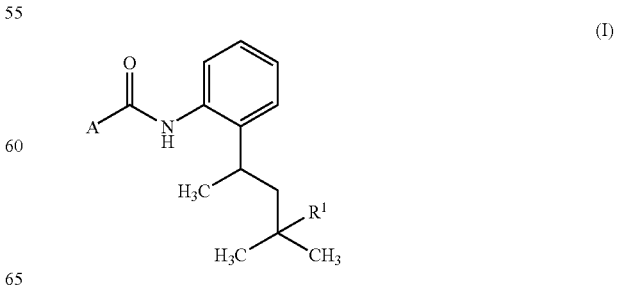

in which $R^1$ and A are as defined above.

Particularly preferred are active compound combinations A to U comprising a carboxamide of the formula (I) (group 1)

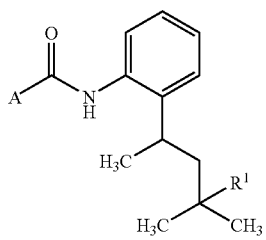

in which
R¹ represents hydrogen, fluorine, chlorine, methyl, ethyl or trifluoromethyl,
A represents one of the radicals A1 or A2 below:

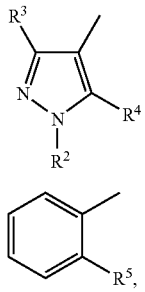

R² represents methyl,
R³ represents methyl, difluoromethyl or trifluoromethyl,
R⁴ represents hydrogen or fluorine,
R⁵ represents iodine or trifluoromethyl.

Very particularly preferred are active compound combinations A to U in which the carboxamide of the formula (I) (group 1) is selected from the list below:
(1-1) N-[2-(1,3-dimethylbutyl)phenyl]-1,3-dimethyl-1H-pyrazole-4-carboxamide
(1-2) N-[2-(1,3-dimethylbutyl)phenyl]-5-fluoro-1,3-dimethyl-1H-pyrazole-4-carboxamide
(1-3) N-[2-(1,3-dimethylbutyl)phenyl]-5-chloro-1,3-dimethyl-1H-pyrazole-4-carboxamide
(14) 3-(difluoromethyl)-N-[2-(1,3-dimethylbutyl)phenyl]-1-methyl-1H-pyrazole-4-carboxamide
(1-5) 3-(trifluoromethyl)-N-[2-(1,3-dimethylbutyl)phenyl]-5-fluoro-1-methyl-1H-pyrazole-4-carboxamide
(1-6) 3-(trifluoromethyl)-N-[2-(1,3-dimethylbutyl)phenyl]-5-chloro-1-methyl-1H-pyrazole-4-carboxamide
(1-7) 1,3-dimethyl-N-[2-(1,3,3-trimethylbutyl)phenyl]-1H-pyrazole-4-carboxamide
(1-8) 5-fluoro-1,3-dimethyl-N-[2-(1,3,3-trimethylbutyl)phenyl]-1H-pyrazole-4-carboxamide
(1-9) 3-(difluoromethyl)-1-methyl-N-[2-(1,3,3-trimethylbutyl)phenyl]-1H-pyrazole-4-carboxamide
(1-10) 3-(trifluoromethyl)-1-methyl-N-[2-(1,3,3-trimethylbutyl)phenyl]-1H-pyrazole-4-carboxamide
(1-11) 3-trifluoromethyl-5-fluoro-1-methyl-N-[2-(1,3,3-trimethylbutyl)phenyl]-1H-pyrazole-4-carboxamide
(1-12) 3-trifluoromethyl-5-chloro-1-methyl-N-[2-(1,3,3-trimethylbutyl)phenyl]-1H-pyrazole-4-carboxamide
(1-13) N-[2-(1,3-dimethylbutyl)phenyl]-2-iodobenzamide
(1-14) 2-iodo-N-[2-(1,3,3-trimethylbutyl)phenyl]benzamide
(1-15) N-[2-(1,3-dimethylbutyl)phenyl]-2-(trifluoromethyl)benzamide
(1-16) 2-(trifluoromethyl)-N-[2-(1,3,3-trimethylbutyl)phenyl]benzamide Especially preferred are active compound combinations A to U in which the carboxamide of the formula (I) (group 1) is selected from the list below:
(1-2) N-[2-(1,3-dimethylbutyl)phenyl]-5-fluoro-1,3-dimethyl-1H-pyrazole-4-carboxamide
(1-8) 5-fluoro-1,3-dimethyl-N-[2-(1,3,3-trimethylbutyl)phenyl]-1H-pyrazole-4-carboxamide
(1-10) 3-trifluoromethyl) 1-methyl-N-[2-(1,3,3-trimethylbutyl)phenyl]-1H-pyrazole-4-carboxamide
(1-13) N-[2-(1,3-dimethylbutyl)phenyl]-2-iodobenzamide
(1-14) 2-iodo-N-[2-(1,3,3-trimethylbutyl)phenyl]benzamide
(1-15) N-[2-(1,3-dimethylbutyl)phenyl]-2-(trifluoromethyl)benzamide
(1-16) 2-trifluoromethyl)-N-[2-(1,3,3-trimethylbutyl)phenyl]benzamide In addition to a carboxamide of the formula (I) (group 1), the active compound combinations A also comprise a strobilurin of the formula (II) (group 2)

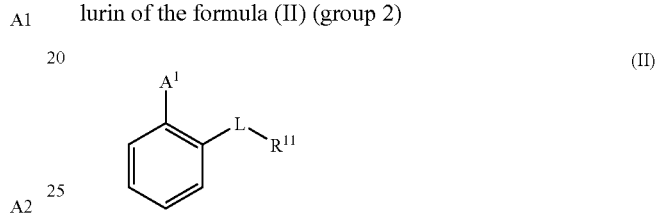

in which A¹, L and R¹¹ are as defined above.

Preferred are active compound combinations A in which the strobilurin of the formula (II) (group 2) is selected from the list below:
(2-1) azoxystrobin
(2-2) fluoxastrobin
(2-3) (2E)-2-(2-{[6-(3-chloro-2-methylphenoxy)-5-fluoro-4-pyrimidinyl]oxy}-3-phenyl)-2-(methoxyimino)-N-methylethanamide
(2-4) trifloxystrobin
(2-5) (2E)-2-(methoxyimino)-N-methyl-2-(2-{[({(1E)-1-[3-trifluoromethyl)phenyl]-ethyliden}amino)oxy]methyl}phenyl)ethanamide
(2-6) (2E)-2-methoxyimino-N-methyl-2-{2-[(E)({1-[3-(trifluoromethyl)phenyl]ethoxy}-imino)methyl]phenyl}ethanamide
(2-7) orysastrobin
(2-8) 5-methoxy-2-methyl-4-(2-{[({(1E)-1-[3-trifluoromethyl)phenyl]ethyliden}-amino)oxy]methyl}phenyl)-2,4-dihydro-3H-1,2,4-triazol-3-one
(2-9) kresoxim-methyl
(2-10) dimoxystrobin
(2-11) picoxystrobin
(2-12) pyraclostrobin
(2-13) metominostrobin Particularly preferred are active compound combinations A in which the strobilurin of the formula (II) (group 2) is selected from the list below:
(2-1) azoxystrobin
(2-2) fluoxastrobin
(2-3) (2E)₂-₂-{[6-(3-chloro-2-methylphenoxy)-5-fluoro-4-pyrimidinyl]oxy}phenyl)-2-(methoxyimino)-N-methylethanamide
(2-4) trifloxystrobin
(2-12) pyraclostrobin
(2-9) kresoxim-methyl
(2-10) dimoxystrobin
(2-11) picoxystrobin
(2-13) metominostrobin Emphasis is given to the active compound combinations A listed in Table 1 below:

TABLE 1

| | Active compound combinations A | |
|---|---|---|
| No. | Carboxamide of the formula (I) | Strobilurin of the formula (II) |
| A-1 | (1-2) N-[2-(1,3-dimethylbutyl)phenyl]-5-fluoro-1,3-dimethyl-1H-pyrazole-4-carboxamide | (2-2) fluoxastrobin |
| A-2 | (1-2) N-[2-(1,3-dimethylbutyl)phenyl]-5-fluoro-1,3-dimethyl-1H-pyrazole-4-carboxamide | (2-3) (2E)-2-(2-{[6-(3-chloro-2-methylphenoxy)-5-fluoro-4-pyrimidinyl]oxy}phenyl)-2-(methoxyimino)-N-methylethanamide |
| A-3 | (1-2) N-[2-(1,3-dimethylbutyl)phenyl]-5-fluoro-1,3-dimethyl-1H-pyrazole-4-carboxamide | (2-4) trifloxystrobin |
| A-4 | (1-8) 5-fluoro-1,3-dimethyl-N-[2-(1,3,3-trimethylbutyl)phenyl]-1H-pyrazole-4-carboxamide | (2-2) fluoxastrobin |
| A-5 | (1-8) 5-fluoro-1,3-dimethyl-N-[2-(1,3,3-trimethylbutyl)phenyl]-1H-pyrazole-4-carboxamide | (2-3) (2E)-2-(2-{[6-(3-chloro-2-methylphenoxy)-5-fluoro-4-pyrimidinyl]oxy}phenyl)-2-(methoxyimino)-N-methylethanamide |
| A-6 | (1-8) 5-fluoro-1,3-dimethyl-N-[2-(1,3,3-trimethylbutyl)phenyl]-1H-pyrazole-4-carboxamide | (2-4) trifloxystrobin |
| A-7 | (1-10) 3-(trifluoromethyl)-1-methyl-N-[2-(1,3,3-trimethylbutyl)phenyl]-1H-pyrazole-4-carboxamide | (2-2) fluoxastrobin |
| A-8 | (1-10) 3-(trifluoromethyl)-1-methyl-N-[2-(1,3,3-trimethylbutyl)phenyl]-1H-pyrazole-4-carboxamide | (2-3) (2E)-2-(2-{[6-(3-chloro-2-methylphenoxy)-5-fluoro-4-pyrimidinyl]oxy}phenyl)-2-(methoxyimino)-N-methylethanamide |
| A-9 | (1-10) 3-(trifluoromethyl)-1-methyl-N-[2-(1,3,3-trimethylbutyl)phenyl]-1H-pyrazole-4-carboxamide | (2-4) trifloxystrobin |
| A-10 | (1-13) N-[2-(1,3-dimethylbutyl)phenyl]-2-iodobenzamide | (2-2) fluoxastrobin |
| A-11 | (1-13) N-[2-(1,3-dimethylbutyl)phenyl]-2-iodobenzamide | (2-3) (2E)-2-(2-{[6-(3-chloro-2-methylphenoxy)-5-fluoro-4-pyrimidinyl]oxy}phenyl)-2-(methoxyimino)-N-methylethanamide |
| A-12 | (1-13) N-[2-(1,3-dimethylbutyl)phenyl]-2-iodobenzamide | (2-4) trifloxystrobin |
| A-13 | (1-14) 2-iodo-N-[2-(1,3,3-trimethylbutyl)phenyl]-benzamide | (2-2) fluoxastrobin |
| A-14 | (1-14) 2-iodo-N-[2-(1,3,3-trimethylbutyl)phenyl]-benzamide | (2-3) (2E)-2-(2-{[6-(3-chloro-2-methylphenoxy)-5-fluoro-4-pyrimidinyl]oxy}phenyl)-2-(methoxyimino)-N-methylethanamide |
| A-15 | (1-14) 2-iodo-N-[2-(1,3,3-trimethylbutyl)phenyl]-benzamide | (2-4) trifloxystrobin |
| A-16 | (1-15) N-[2-(1,3-dimethylbutyl)phenyl]-2-(trifluoromethyl)benzamide | (2-2) fluoxastrobin |
| A-17 | (1-15) N-[2-(1,3-dimethylbutyl)phenyl]-2-(trifluoromethyl)benzamide | (2-3) (2E)-2-(2-{[6-(3-chloro-2-methylphenoxy)-5-fluoro-4-pyrimidinyl]oxy}-phenyl)-2-(methoxyimino)-N-methylethanamide |
| A-18 | (1-15) N-[2-(1,3-dimethylbutyl)phenyl]-2-(trifluoromethyl)benzamide | (2-4) trifloxystrobin |
| A-19 | (1-16) 2-(trifluoromethyl)-N-[2-(1,3,3-trimethylbutyl)phenyl]benzamide | (2-2) fluoxastrobin |
| A-20 | (1-16) 2-(trifluoromethyl)-N-[2-(1,3,3-trimethylbutyl)phenyl]benzamide | (2-3) (2E)-2-(2-{[6-(3-chloro-2-methylphenoxy)-5-fluoro-4-pyrimidinyl]oxy}phenyl)-2-(methoxyimino)-N-methylethanamide |
| A-21 | (1-16) 2-(trifluoromethyl)-N-[2-(1,3,3-trimethylbutyl)phenyl]benzamide | (2-4) trifloxystrobin |
| A-22 | (1-2) N-[2-(1,3-dimethylbutyl)phenyl]-5-fluoro-1,3-dimethyl-1H-pyrazole-4-carboxamide | (2-1) azoxystrobin |
| A-23 | (1-2) N-[2-(1,3-dimethylbutyl)phenyl]-5-fluoro-1,3-dimethyl-1H-pyrazole-4-carboxamide | (2-12) pyraclostrobin |
| A-24 | (1-2) N-[2-(1,3-dimethylbutyl)phenyl]-5-fluoro-1,3-dimethyl-1H-pyrazole-4-carboxamide | (2-9) kresoxim-methyl |
| A-25 | (1-2) N-[2-(1,3-dimethylbutyl)phenyl]-5-fluoro-1,3-dimethyl-1H-pyrazole-4-carboxamide | (2-10) dimoxystrobin |
| A-26 | (1-2) N-[2-(1,3-dimethylbutyl)phenyl]-5-fluoro-1,3-dimethyl-1H-pyrazole-4-carboxamide | (2-11) picoxystrobin |
| A-27 | (1-2) N-[2-(1,3-dimethylbutyl)phenyl]-5-fluoro-1,3-dimethyl-1H-pyrazole-4-carboxamide | (2-13) metominostrobin |
| A-28 | (1-8) 5-fluoro-1,3-dimethyl-N-[2-(1,3,3-trimethylbutyl)phenyl]-1H-pyrazole-4-carboxamide | (2-1) azoxystrobin |
| A-29 | (1-8) 5-fluoro-1,3-dimethyl-N-[2-(1,3,3-trimethylbutyl)phenyl]-1H-pyrazole-4-carboxamide | (2-12) pyraclostrobin |
| A-30 | (1-8) 5-fluoro-1,3-dimethyl-N-[2-(1,3,3-trimethylbutyl)phenyl]-1H-pyrazole-4-carboxamide | (2-9) kresoxim-methyl |
| A-31 | (1-8) 5-fluoro-1,3-dimethyl-N-[2-(1,3,3-trimethylbutyl)phenyl]-1H-pyrazole-4-carboxamide | (2-10) dimoxystrobin |
| A-32 | (1-8) 5-fluoro-1,3-dimethyl-N-[2-(1,3,3-trimethylbutyl)phenyl]-1H-pyrazole-4-carboxamide | (2-11) picoxystrobin |

TABLE 1-continued

Active compound combinations A

| No. | Carboxamide of the formula (I) | Strobilurin of the formula (II) |
|---|---|---|
| A-33 | (1-8) 5-fluoro-1,3-dimethyl-N-[2-(1,3,3-trimethylbutyl)-phenyl]-1H-pyrazole-4-carboxamide | (2-13) metominostrobin |
| A-34 | (1-10) 3-(trifluoromethyl)-1-methyl-N-[2-(1,3,3-trimethylbutyl)phenyl]-1H-pyrazole-4-carboxamide | (2-1) azoxystrobin |
| A-35 | (1-10) 3-(trifluoromethyl)-1-methyl-N-[2-(1,3,3-trimethylbutyl)phenyl]-1H-pyrazole-4-carboxamide | (2-12) pyraclostrobin |
| A-36 | (1-10) 3-(trifluoromethyl)-1-methyl-N-[2-(1,3,3-trimethylbutyl)phenyl]-1H-pyrazole-4-carboxamide | (2-9) kresoxim-methyl |
| A-37 | (1-10) 3-(trifluoromethyl)-1-methyl-N-[2-(1,3,3-trimethylbutyl)phenyl]-1H-pyrazole-4-carboxamide | (2-10) dimoxystrobin |
| A-38 | (1-10) 3-(trifluoromethyl)-1-methyl-N-[2-(1,3,3-trimethylbutyl)phenyl]-1H-pyrazole-4-carboxamide | (2-11) picoxystrobin |
| A-39 | (1-10) 3-(trifluoromethyl)-1-methyl-N-[2-(1,3,3-trimethylbutyl)phenyl]-1H-pyrazole-4-carboxamide | (2-13) metominostrobin |
| A-40 | (1-13) N-[2-(1,3-dimethylbutyl)phenyl]-2-iodobenzamide | (2-1) azoxystrobin |
| A-41 | (1-13) N-[2-(1,3-dimethylbutyl)phenyl]-2-iodobenzamide | (2-12) pyraclostrobin |
| A-42 | (1-13) N-[2-(1,3-dimethylbutyl)phenyl]-2-iodobenzamide | (2-9) kresoxim-methyl |
| A-43 | (1-13) N-[2-(1,3-dimethylbutyl)phenyl]-2-iodobenzamide | (2-10) dimoxystrobin |
| A-44 | (1-13) N-[2-(1,3-dimethylbutyl)phenyl]-2-iodobenzamide | (2-11) picoxystrobin |
| A-45 | (1-13) N-[2-(1,3-dimethylbutyl)phenyl]-2-iodobenzamide | (2-13) metominostrobin |
| A-46 | (1-14) 2-iodo-N-[2-(1,3,3-trimethylbutyl)phenyl]-benzamide | (2-1) azoxystrobin |
| A-47 | (1-14) 2-iodo-N-[2-(1,3,3-trimethylbutyl)phenyl]-benzamide | (2-12) pyraclostrobin |
| A-48 | (1-14) 2-iodo-N-[2-(1,3,3-trimethylbutyl)phenyl]-benzamide | (2-9) kresoxim-methyl |
| A-49 | (1-14) 2-iodo-N-[2-(1,3,3-trimethylbutyl)phenyl]-benzamide | (2-10) dimoxystrobin |
| A-50 | (1-14) 2-iodo-N-[2-(1,3,3-trimethylbutyl)phenyl]-benzamide | (2-11) picoxystrobin |
| A-51 | (1-14) 2-iodo-N-[2-(1,3,3-trimethylbutyl)phenyl]-benzamide | (2-13) metominostrobin |
| A-52 | (1-15) N-[2-(1,3-dimethylbutyl)phenyl]-2-(trifluoro-methyl)benzamide | (2-1) azoxystrobin |
| A-53 | (1-15) N-[2-(1,3-dimethylbutyl)phenyl]-2-(trifluoro-methyl)benzamide | (2-12) pyraclostrobin |
| A-54 | (1-15) N-[2-(1,3-dimethylbutyl)phenyl]-2-(trifluoro-methyl)benzamide | (2-9) kresoxim-methyl |
| A-55 | (1-15) N-[2-(1,3-dimethylbutyl)phenyl]-2-(trifluoro-methyl)benzamide | (2-10) dimoxystrobin |
| A-56 | (1-15) N-[2-(1,3-dimethylbutyl)phenyl]-2-(trifluoro-methyl)benzamide | (2-11) picoxystrobin |
| A-57 | (1-15) N-[2-(1,3-dimethylbutyl)phenyl]-2-(trifluoro-methyl)benzamide | (2-13) metominostrobin |
| A-58 | (1-16) 2-(trifluoromethyl)-N-[2-(1,3,3-trimethylbutyl)-phenyl]benzamide | (2-1) azoxystrobin |
| A-59 | (1-16) 2-(trifluoromethyl)-N-[2-(1,3,3-trimethylbutyl)-phenyl]benzamide | (2-12) pyraclostrobin |
| A-60 | (1-16) 2-(trifluoromethyl)-N-[2-(1,3,3-trimethylbutyl)-phenyl]benzamide | (2-9) kresoxim-methyl |
| A-61 | (1-16) 2-(trifluoromethyl)-N-[2-(1,3,3-trimethylbutyl)-phenyl]benzamide | (2-10) dimoxystrobin |
| A-62 | (1-16) 2-(trifluoromethyl)-N-[2-(1,3,3-trimethylbutyl)-phenyl]benzamide | (2-11) picoxystrobin |
| A-63 | (1-16) 2-(trifluoromethyl)-N-[2-(1,3,3-trimethylbutyl)-phenyl]benzamide | (2-13) metominostrobin |

In addition to a carboxamide of the formula (I) (group 1), the active compound combinations B also comprise a triazole of the formula (III) (group 3)

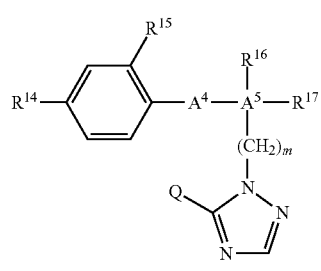

(III)

in which Q, m, $R^{14}$, $R^{15}$, $A^4$, $A^5$, $R^{16}$ and $R^{17}$ are as defined above.

Preference is given to active compound combinations B in which the triazole of the formula (III) (group 3) is selected from the list below:

(3-1) azaconazole
(3-2) etaconazole
(3-3) propiconazole
(3-4) difenoconazole
(3-5) bromuconazole
(3-6) cyproconazole
(3-7) hexaconazole
(3-8) penconazole
(3-9) myclobutanil
(3-10) tetraconazole (3-11) flutriafol
(3-12) epoxiconazole
(3-13) flusilazole
(3-14) simeconazole
(3-15) prothioconazole
(3-16) fenbuconazole
(3-17) tebuconazole
(3-18) ipconazole
(3-19) metconazole
(3-20) triticonazole
(3-21) bitertanol
(3-22) triadimenol
(3-23) triadimefon
(3-24) fluquinconazole
(3-25) quinconazole Particular preference is given to active compound combinations B in which the triazole of the formula (III) (group 3) is selected from the list below:
(3-3) propiconazole
(3-6) cyproconazole
(3-15) prothioconazole
(3-17) tebuconazole
(3-21) bitertanol
(3-4) difenoconazole
(3-7) hexaconazole
(3-19) metconazole
(3-22) triadimenol
(3-24) fluquinconazole Emphasis is given to the active compound combinations B listed in Table 2 below:

TABLE 2

Active compound combinations B

| No. | Carboxamide of the formula (I) | Triazole of the formula (III) |
|---|---|---|
| B-1 | (1-2) N-[2-(1,3-dimethylbutyl)phenyl]-5-fluoro-1,3-dimethyl-1H-pyrazole-4-carboxamide | (3-3) propiconazole |
| B-2 | (1-2) N-[2-(1,3-dimethylbutyl)phenyl]-5-fluoro-1,3-dimethyl-1H-pyrazole-4-carboxamide | (3-6) cyproconazole |
| B-3 | (1-2) N-[2-(1,3-dimethylbutyl)phenyl]-5-fluoro-1,3-dimethyl-1H-pyrazole-4-carboxamide | (3-15) prothioconazole |
| B-4 | (1-2) N-[2-(1,3-dimethylbutyl)phenyl]-5-fluoro-1,3-dimethyl-1H-pyrazole-4-carboxamide | (3-17) tebuconazole |
| B-5 | (1-2) N-[2-(1,3-dimethylbutyl)phenyl]-5-fluoro-1,3-dimethyl-1H-pyrazole-4-carboxamide | (3-21) bitertanol |
| B-6 | (1-8) 5-fluoro-1,3-dimethyl-N-[2-(1,3,3-trimethylbutyl)phenyl]-1H-pyrazole-4-carboxamide | (3-3) propiconazole |
| B-7 | (1-8) 5-fluoro-1,3-dimethyl-N-[2-(1,3,3-trimethylbutyl)phenyl]-1H-pyrazole-4-carboxamide | (3-6) cyproconazole |
| B-8 | (1-8) 5-fluoro-1,3-dimethyl-N-[2-(1,3,3-trimethylbutyl)phenyl]-1H-pyrazole-4-carboxamide | (3-15) prothioconazole |
| B-9 | (1-8) 5-fluoro-1,3-dimethyl-N-[2-(1,3,3-trimethylbutyl)phenyl]-1H-pyrazole-4-carboxamide | (3-17) tebuconazole |
| B-10 | (1-8) 5-fluoro-1,3-dimethyl-N-[2-(1,3,3-trimethylbutyl)phenyl]-1H-pyrazole-4-carboxamide | (3-21) bitertanol |
| B-11 | (1-10) 3-(trifluoromethyl)-1-methyl-N-[2-(1,3,3-trimethylbutyl)-phenyl]-1H-pyrazole-4-carboxamide | (3-3) propiconazole |
| B-12 | (1-10) 3-(trifluoromethyl)-1-methyl-N-[2-(1,3,3-trimethylbutyl)-phenyl]-1H-pyrazole-4-carboxamide | (3-6) cyproconazole |
| B-13 | (1-10) 3-(trifluoromethyl)-1-methyl-N-[2-(1,3,3-trimethylbutyl)-phenyl]-1H-pyrazole-4-carboxamide | (3-15) prothioconazole |
| B-14 | (1-10) 3-(trifluoromethyl)-1-methyl-N-[2-(1,3,3-trimethylbutyl)-phenyl]-1H-pyrazole-4-carboxamide | (3-17) tebuconazole |
| B-15 | (1-10) 3-(trifluoromethyl)-1-methyl-N-[2-(1,3,3-trimethylbutyl)-phenyl]-1H-pyrazole-4-carboxamide | (3-21) bitertanol |
| B-16 | (1-13) N-[2-(1,3-dimethylbutyl)phenyl]-2-iodobenzamide | (3-3) propiconazole |
| B-17 | (1-13) N-[2-(1,3-dimethylbutyl)phenyl]-2-iodobenzamide | (3-6) cyproconazole |
| B-18 | (1-13) N-[2-(1,3-dimethylbutyl)phenyl]-2-iodobenzamide | (3-15) prothioconazole |
| B-19 | (1-13) N-[2-(1,3-dimethylbutyl)phenyl]-2-iodobenzamide | (3-17) tebuconazole |
| B-20 | (1-13) N-[2-(1,3-dimethylbutyl)phenyl]-2-iodobenzamide | (3-21) bitertanol |
| B-21 | (1-14) 2-iodo-N-[2-(1,3,3-trimethylbutyl)phenyl]benzamide | (3-3) propiconazole |
| B-22 | (1-14) 2-iodo-N-[2-(1,3,3-trimethylbutyl)phenyl]benzamide | (3-6) cyproconazole |
| B-23 | (1-14) 2-iodo-N-[2-(1,3,3-trimethylbutyl)phenyl]benzamide | (3-15) prothioconazole |
| B-24 | (1-14) 2-iodo-N-[2-(1,3,3-trimethylbutyl)phenyl]benzamide | (3-17) tebuconazole |
| B-25 | (1-14) 2-iodo-N-[2-(1,3,3-trimethylbutyl)phenyl]benzamide | (3-21) bitertanol |
| B-26 | (1-15) N-[2-(1,3-dimethylbutyl)phenyl]-2-(trifluoromethyl)benzamide | (3-3) propiconazole |
| B-27 | (1-15) N-[2-(1,3-dimethylbutyl)phenyl]-2-(trifluoromethyl)benzamide | (3-6) cyproconazole |
| B-28 | (1-15) N-[2-(1,3-dimethylbutyl)phenyl]-2-(trifluoromethyl)benzamide | (3-15) prothioconazole |
| B-29 | (1-15) N-[2-(1,3-dimethylbutyl)phenyl]-2-(trifluoromethyl)benzamide | (3-17) tebuconazole |
| B-30 | (1-15) N-[2-(1,3-dimethylbutyl)phenyl]-2-(trifluoromethyl)benzamide | (3-21) bitertanol |
| B-31 | (1-16) 2-(trifluoromethyl)-N-[2-(1,3,3-trimethylbutyl)phenyl]-benzamide | (3-3) propiconazole |
| B-32 | (1-16) 2-(trifluoromethyl)-N-[2-(1,3,3-trimethylbutyl)phenyl]-benzamide | (3-6) cyproconazole |
| B-33 | (1-16) 2-(trifluoromethyl)-N-[2-(1,3,3-trimethylbutyl)phenyl]-benzamide | (3-15) prothioconazole |
| B-34 | (1-16) 2-(trifluoromethyl)-N-[2-(1,3,3-trimethylbutyl)phenyl]-benzamide | (3-17) tebuconazole |
| B-35 | (1-16) 2-(trifluoromethyl)-N-[2-(1,3,3-trimethylbutyl)phenyl]-benzamide | (3-21) bitertanol |

TABLE 2-continued

Active compound combinations B

| No. | Carboxamide of the formula (I) | Triazole of the formula (III) |
|---|---|---|
| B-36 | (1-2) N-[2-(1,3-dimethylbutyl)phenyl]-5-fluoro-1,3-dimethyl-1H-pyrazole-4-carboxamide | (3-4) difenoconazole |
| B-37 | (1-2) N-[2-(1,3-dimethylbutyl)phenyl]-5-fluoro-1,3-dimethyl-1H-pyrazole-4-carboxamide | (3-7) hexaconazole |
| B-38 | (1-2) N-[2-(1,3-dimethylbutyl)phenyl]-5-fluoro-1,3-dimethyl-1H-pyrazole-4-carboxamide | (3-19) metconazole |
| B-39 | (1-2) N-[2-(1,3-dimethylbutyl)phenyl]-5-fluoro-1,3-dimethyl-1H-pyrazole-4-carboxamide | (3-22) triadimenol |
| B-40 | (1-2) N-[2-(1,3-dimethylbutyl)phenyl]-5-fluoro-1,3-dimethyl-1H-pyrazole-4-carboxamide | (3-24) fluquinconazole |
| B-41 | (1-8) 5-fluoro-1,3-dimethyl-N-[2-(1,3,3-trimethylbutyl)phenyl]-1H-pyrazole-4-carboxamide | (3-4) difenoconazole |
| B-42 | (1-8) 5-fluoro-1,3-dimethyl-N-[2-(1,3,3-trimethylbutyl)phenyl]-1H-pyrazole-4-carboxamide | (3-7) hexaconazole |
| B-43 | (1-8) 5-fluoro-1,3-dimethyl-N-[2-(1,3,3-trimethylbutyl)phenyl]-1H-pyrazole-4-carboxamide | (3-19) metconazole |
| B-44 | (1-8) 5-fluoro-1,3-dimethyl-N-[2-(1,3,3-trimethylbutyl)phenyl]-1H-pyrazole-4-carboxamide | (3-22) triadimenol |
| B-45 | (1-8) 5-fluoro-1,3-dimethyl-N-[2-(1,3,3-trimethylbutyl)phenyl]-1H-pyrazole-4-carboxamide | (3-24) fluquinconazole |
| B-46 | (1-10) 3-(trifluoromethyl)-1-methyl-N-[2-(1,3,3-trimethylbutyl)-phenyl]-1H-pyrazole-4-carboxamide | (3-4) difenoconazole |
| B-47 | (1-10) 3-(trifluoromethyl)-1-methyl-N-[2-(1,3,3-trimethylbutyl)-phenyl]-1H-pyrazole-4-carboxamide | (3-7) hexaconazole |
| B-48 | (1-10) 3-(trifluoromethyl)-1-methyl-N-[2-(1,3,3-trimethylbutyl)-phenyl]-1H-pyrazole-4-carboxamide | (3-19) metconazole |
| B-49 | (1-10) 3-(trifluoromethyl)-1-methyl-N-[2-(1,3,3-trimethylbutyl)-phenyl]-1H-pyrazole-4-carboxamide | (3-22) triadimenol |
| B-50 | (1-10) 3-(trifluoromethyl)-1-methyl-N-[2-(1,3,3-trimethylbutyl)-phenyl]-1H-pyrazole-4-carboxamide | (3-24) fluquinconazole |
| B-51 | (1-13) N-[2-(1,3-dimethylbutyl)phenyl]-2-iodobenzamide | (3-4) difenoconazole |
| B-52 | (1-13) N-[2-(1,3-dimethylbutyl)phenyl]-2-iodobenzamide | (3-7) hexaconazole |
| B-53 | (1-13) N-[2-(1,3-dimethylbutyl)phenyl]-2-iodobenzamide | (3-19) metconazole |
| B-54 | (1-13) N-[2-(1,3-dimethylbutyl)phenyl]-2-iodobenzamide | (3-22) triadimenol |
| B-55 | (1-13) N-[2-(1,3-dimethylbutyl)phenyl]-2-iodobenzamide | (3-24) fluquinconazole |
| B-56 | (1-14) 2-iodo-N-[2-(1,3,3-trimethylbutyl)phenyl]benzamide | (3-4) difenoconazole |
| B-57 | (1-14) 2-iodo-N-[2-(1,3,3-trimethylbutyl)phenyl]benzamide | (3-7) hexaconazole |
| B-58 | (1-14) 2-iodo-N-[2-(1,3,3-trimethylbutyl)phenyl]benzamide | (3-19) metconazole |
| B-59 | (1-14) 2-iodo-N-[2-(1,3,3-trimethylbutyl)phenyl]benzamide | (3-22) triadimenol |
| B-60 | (1-14) 2-iodo-N-[2-(1,3,3-trimethylbutyl)phenyl]benzamide | (3-24) fluquinconazole |
| B-61 | (1-15) N-[2-(1,3-dimethylbutyl)phenyl]-2-(trifluoromethyl)benzamide | (3-4) difenoconazole |
| B-62 | (1-15) N-[2-(1,3-dimethylbutyl)phenyl]-2-(trifluoromethyl)benzamide | (3-7) hexaconazole |
| B-63 | (1-15) N-[2-(1,3-dimethylbutyl)phenyl]-2-(trifluoromethyl)benzamide | (3-19) metconazole |
| B-64 | (1-15) N-[2-(1,3-dimethylbutyl)phenyl]-2-(trifluoromethyl)benzamide | (3-22) triadimenol |
| B-65 | (1-15) N-[2-(1,3-dimethylbutyl)phenyl]-2-(trifluoromethyl)benzamide | (3-24) fluquinconazole |
| B-66 | (1-16) 2-(trifluoromethyl)-N-[2-(1,3,3-trimethylbutyl)phenyl]-benzamide | (3-4) difenoconazole |
| B-67 | (1-16) 2-(trifluoromethyl)-N-[2-(1,3,3-trimethylbutyl)phenyl]-benzamide | (3-7) hexaconazole |
| B-68 | (1-16) 2-(trifluoromethyl)-N-[2-(1,3,3-trimethylbutyl)phenyl]-benzamide | (3-19) metconazole |
| B-69 | (1-16) 2-(trifluoromethyl)-N-[2-(1,3,3-trimethylbutyl)phenyl]-benzamide | (3-22) triadimenol |
| B-70 | (1-16) 2-(trifluoromethyl)-N-[2-(1,3,3-trimethylbutyl)phenyl]-benzamide | (3-24) fluquinconazole |

In addition to a carboxamide of the formula (I) (group 1), the active compound combinations C also comprise a stilphenamide of the formula (IV) (group 4)

(IV)

in which $R^{19}$ is as defined above.

Preference is given to active compound combinations C in which the sulphenamide of the formula (IV) (group 4) is selected from the list below:

(4-1) dichlofluanid (4-2) tolylfluanid

Emphasis is given to the active compound combinations C listed in Table 3 below:

TABLE 3

Active compound combinations C

| No. | Carboxamide of the formula (I) | Sulphenamide of the formula (IV) |
|---|---|---|
| C-1 | (1-2) N-[2-(1,3-dimethylbutyl)phenyl]-5-fluoro-1,3-dimethyl-1H-pyrazole-4-carboxamide | (4-1) dichlofluanid |
| C-2 | (1-2) N-[2-(1,3-dimethylbutyl)phenyl]-5-fluoro-1,3-dimethyl-1H-pyrazole-4-carboxamide | (4-2) tolylfluanid |
| C-3 | (1-8) 5-fluoro-1,3-dimethyl-N-[2-(1,3,3-trimethylbutyl)phenyl]-1H-pyrazole-4-carboxamide | (4-1) dichlofluanid |
| C-4 | (1-8) 5-fluoro-1,3-dimethyl-N-[2-(1,3,3-trimethylbutyl)phenyl]-1H-pyrazole-4-carboxamide | (4-2) tolylfluanid |
| C-5 | (1-10) 3-(trifluoromethyl)-1-methyl-N-[2-(1,3,3-trimethylbutyl)phenyl]-1H-pyrazole-4-carboxamide | (4-1) dichlofluanid |
| C-6 | (1-10) 3-(trifluoromethyl)-1-methyl-N-[2-(1,3,3-trimethylbutyl)phenyl]-1H-pyrazole-4-carboxamide | (4-2) tolylfluanid |
| C-7 | (1-13) N-[2-(1,3-dimethylbutyl)phenyl]-2-iodobenzamide | (4-1) dichlofluanid |
| C-8 | (1-13) N-[2-(1,3-dimethylbutyl)phenyl]-2-iodobenzamide | (4-2) tolylfluanid |
| C-9 | (1-14) 2-iodo-N-[2-(1,3,3-trimethylbutyl)phenyl]benzamide | (4-1) dichlofluanid |
| C-10 | (1-14) 2-iodo-N-[2-(1,3,3-trimethylbutyl)phenyl]benzamide | (4-2) tolylfluanid |
| C-11 | (1-15) N-[2-(1,3-dimethylbutyl)phenyl]-2-(trifluoromethyl)benzamide | (4-1) dichlofluanid |
| C-12 | (1-15) N-[2-(1,3-dimethylbutyl)phenyl]-2-(trifluoromethyl)benzamide | (4-2) tolylfluanid |
| C-13 | (1-16) 2-(trifluoromethyl)-N-[2-(1,3,3-trimethylbutyl)phenyl]benzamide | (4-1) dichlofluanid |
| C-14 | (1-16) 2-(trifluoromethyl)-N-[2-(1,3,3-trimethylbutyl)phenyl]benzamide | (4-2) tolylfluanid |

In addition to a carboxamide of the formula (I) (group 1), the active compound combinations D also comprise a valinamide (group 5) selected from (5-1) iprovalicarb
(5-2) $N^1$-[2-(4-{[3-(4-chlorophenyl)-2-propynyl]oxy}-3-methoxyphenyl)ethyl]-$N^2$-(methyl-sulphonyl)-D-valinamide
(5-3) benthiavalicarb Preference is given to active compound combinations D in which the valinamide (group 5) is selected from the list below:

(5-1) iprovalicarb
(5-3) benthiavalicarb

Emphasis is given to the active compound combinations D listed in Table 4 below:

In addition to a carboxamide of the formula (I) (group 1), the active compound combinations E also comprise a carboxamide of the formula (V) (group 6)

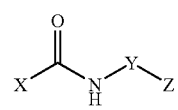 (V)

in which X, Y and Z are as defined above.

Preference is given to active compound combinations E in which the carboxamide of the formula (V) (group 6) is selected from the list below:

(6-1) 2-chloro-N-(1,1,3-trimethylindan-4-yl)nicotinamide
(6-2) boscalid
(6-3) furametpyr

TABLE 4

Active compound combinations D

| No. | Carboxamide of the formula (I) | Valinamide |
|---|---|---|
| D-1 | (1-2) N-[2-(1,3-dimethylbutyl)phenyl]-5-fluoro-1,3-dimethyl-1H-pyrazole-4-carboxamide | (5-1) iprovalicarb |
| D-2 | (1-2) N-[2-(1,3-dimethylbutyl)phenyl]-5-fluoro-1,3-dimethyl-1H-pyrazole-4-carboxamide | (5-3) benthiavalicarb |
| D-3 | (1-8) 5-fluoro-1,3-dimethyl-N-[2-(1,3,3-trimethylbutyl)phenyl]-1H-pyrazole-4-carboxamide | (5-1) iprovalicarb |
| D-4 | (1-8) 5-fluoro-1,3-dimethyl-N-[2-(1,3,3-trimethylbutyl)phenyl]-1H-pyrazole-4-carboxamide | (5-3) benthiavalicarb |
| D-5 | (1-10) 3-(trifluoromethyl)-1-methyl-N-[2-(1,3,3-trimethylbutyl)phenyl]-1H-pyrazole-4-carboxamide | (5-1) iprovalicarb |
| D-6 | (1-10) 3-(trifluoromethyl)-1-methyl-N-[2-(1,3,3-trimethylbutyl)phenyl]-1H-pyrazole-4-carboxamide | (5-3) benthiavalicarb |
| D-7 | (1-13) N-[2-(1,3-dimethylbutyl)phenyl]-2-iodobenzamide | (5-1) iprovalicarb |
| D-8 | (1-13) N-[2-(1,3-dimethylbutyl)phenyl]-2-iodobenzamide | (5-3) benthiavalicarb |
| D-9 | (1-14) 2-iodo-N-[2-(1,3,3-trimethylbutyl)phenyl]benzamide | (5-1) iprovalicarb |
| D-10 | (1-14) 2-iodo-N-[2-(1,3,3-trimethylbutyl)phenyl]benzamide | (5-3) benthiavalicarb |
| D-11 | (1-15) N-[2-(1,3-dimethylbutyl)phenyl]-2-(trifluoromethyl)benzamide | (5-1) iprovalicarb |
| D-12 | (1-15) N-[2-(1,3-dimethylbutyl)phenyl]-2-(trifluoromethyl)benzamide | (5-3) benthiavalicarb |
| D-13 | (1-16) 2-(trifluoromethyl)-N-[2-(1,3,3-trimethylbutyl)phenyl]benzamide | (5-1) iprovalicarb |
| D-14 | (1-16) 2-(trifluoromethyl)-N-[2-(1,3,3-trimethylbutyl)phenyl]benzamide | (5-3) benthiavalicarb |

(6-4) N-3-p-tolylthiophen-2-yl)-1-methyl-3-trifluoromethyl-1H-pyrazole-4-carboxamide
(6-5) ethaboxam
(6-6) fenhexamid
(6-7) carpropamid
(6-8) 2-chloro-4-(2-fluoro-2-methylpropionylamino)-N,N-dimethylbenzamide
(6-9) picobenzamid
(6-10) zoxamide
(6-11) 3,4-dichloro-N-(2-cyanophenyl)isothiazole-5-carboxamide
(6-12) carboxin
(6-13) tiadinil
(6-14) penthiopyrad
(6-15) silthiofam
(6-16) N-[2-(1,3-dimethylbutyl)phenyl]-1-methyl-4-trifluoromethyl-1H-pyrrole-3-carboxamide Particular preference is given to active compound combinations E in which the carboxamide of the formula (V) (group 6) is selected from the list below:

(6-2) boscalid
(6-5) ethaboxam
(6-6) fenhexamid
(6-7) carpropamid
(6-8) 2-chloro-4-(2-fluoro-2-methyl-propionylamino)-N,N-dimethylbenzamide
(6-9) picobenzamid
(6-10) zoxamide
(6-11) 3,4-dichloro-N-(2-cyanophenyl)isothiazole-5-carboxamide
(6-14) penthiopyrad
(6-16) N-[2-(1,3-dimethylbutyl)phenyl]-1-methyl-4-(trifluoromethyl)-1H-pyrrole-3-carboxamide Very particular preference is given to active compound combinations E in which the carboxamide of the formula (V) (group 6) is selected from the list below:

(6-2) boscalid
(6-6) fenhexamid
(6-7) carpropamid
(6-9) picobenzamid
(6-14) penthiopyrad Emphasis is given to the active compound combinations E listed in Table 5 below:

TABLE 5

Active compound combinations E

| No. | Carboxamide of the formula (I) | Carboxamide of the formula (V) |
|---|---|---|
| E-1 | (1-2) N-[2-(1,3-dimethylbutyl)phenyl]-5-fluoro-1,3-dimethyl-1H-pyrazole-4-carboxamide | (6-2) boscalid |
| E-2 | (1-2) N-[2-(1,3-dimethylbutyl)phenyl]-5-fluoro-1,3-dimethyl-1H-pyrazole-4-carboxamide | (6-6) fenhexamid |
| E-3 | (1-2) N-[2-(1,3-dimethylbutyl)phenyl]-5-fluoro-1,3-dimethyl-1H-pyrazole-4-carboxamide | (6-7) carpropamid |
| E-4 | (1-2) N-[2-(1,3-dimethylbutyl)phenyl]-5-fluoro-1,3-dimethyl-1H-pyrazole-4-carboxamide | (6-9) picobenzamid |
| E-5 | (1-2) N-[2-(1,3-dimethylbutyl)phenyl]-5-fluoro-1,3-dimethyl-1H-pyrazole-4-carboxamide | (6-14) penthiopyrad |
| E-6 | (1-8) 5-fluoro-1,3-dimethyl-N-[2-(1,3,3-trimethylbutyl)phenyl]-1H-pyrazole-4-carboxamide | (6-2) boscalid |
| E-7 | (1-8) 5-fluoro-1,3-dimethyl-N-[2-(1,3,3-trimethylbutyl)phenyl]-1H-pyrazole-4-carboxamide | (6-6) fenhexamid |
| E-8 | (1-8) 5-fluoro-1,3-dimethyl-N-[2-(1,3,3-trimethylbutyl)phenyl]-1H-pyrazole-4-carboxamide | (6-7) carpropamid |
| E-9 | (1-8) 5-fluoro-1,3-dimethyl-N-[2-(1,3,3-trimethylbutyl)phenyl]-1H-pyrazole-4-carboxamide | (6-9) picobenzamid |
| E-10 | (1-8) 5-fluoro-1,3-dimethyl-N-[2-(1,3,3-trimethylbutyl)phenyl]-1H-pyrazole-4-carboxamide | (6-14) penthiopyrad |
| E-11 | (1-10) 3-(trifluoromethyl)-1-methyl-N-[2-(1,3,3-trimethylbutyl)phenyl]-1H-pyrazole-4-carboxamide | (6-2) boscalid |
| E-12 | (1-10) 3-(trifluoromethyl)-1-methyl-N-[2-(1,3,3-trimethylbutyl)phenyl]-1H-pyrazole-4-carboxamide | (6-6) fenhexamid |
| E-13 | (1-10) 3-(trifluoromethyl)-1-methyl-N-[2-(1,3,3-trimethylbutyl)phenyl]-1H-pyrazole-4-carboxamide | (6-7) carpropamid |
| E-14 | (1-10) 3-(trifluoromethyl)-1-methyl-N-[2-(1,3,3-trimethylbutyl)phenyl]-1H-pyrazole-4-carboxamide | (6-9) picobenzamid |
| E-15 | (1-10) 3-(trifluoromethyl)-1-methyl-N-[2-(1,3,3-trimethylbutyl)phenyl]-1H-pyrazole-4-carboxamide | (6-14) penthiopyrad |
| E-16 | (1-13) N-[2-(1,3-dimethylbutyl)phenyl]-2-iodobenzamide | (6-2) boscalid |
| E-17 | (1-13) N-[2-(1,3-dimethylbutyl)phenyl]-2-iodobenzamide | (6-6) fenhexamid |
| E-18 | (1-13) N-[2-(1,3-dimethylbutyl)phenyl]-2-iodobenzamide | (6-7) carpropamid |
| E-19 | (1-13) N-[2-(1,3-dimethylbutyl)phenyl]-2-iodobenzamide | (6-9) picobenzamid |
| E-20 | (1-13) N-[2-(1,3-dimethylbutyl)phenyl]-2-iodobenzamide | (6-14) penthiopyrad |
| E-21 | (1-14) 2-iodo-N-[2-(1,3,3-trimethylbutyl)phenyl]benzamide | (6-2) boscalid |
| E-22 | (1-14) 2-iodo-N-[2-(1,3,3-trimethylbutyl)phenyl]benzamide | (6-6) fenhexamid |
| E-23 | (1-14) 2-iodo-N-[2-(1,3,3-trimethylbutyl)phenyl]benzamide | (6-7) carpropamid |
| E-24 | (1-14) 2-iodo-N-[2-(1,3,3-trimethylbutyl)phenyl]benzamide | (6-9) picobenzamid |
| E-25 | (1-14) 2-iodo-N-[2-(1,3,3-trimethylbutyl)phenyl]benzamide | (6-14) penthiopyrad |
| E-26 | (1-15) N-[2-(1,3-dimethylbutyl)phenyl]-2-(trifluoromethyl)benzamide | (6-2) boscalid |
| E-27 | (1-15) N-[2-(1,3-dimethylbutyl)phenyl]-2-(trifluoromethyl)benzamide | (6-6) fenhexamid |
| E-28 | (1-15) N-[2-(1,3-dimethylbutyl)phenyl]-2-(trifluoromethyl)benzamide | (6-7) carpropamid |
| E-29 | (1-15) N-[2-(1,3-dimethylbutyl)phenyl]-2-(trifluoromethyl)benzamide | (6-9) picobenzamid |
| E-30 | (1-15) N-[2-(1,3-dimethylbutyl)phenyl]-2-(trifluoromethyl)benzamide | (6-14) penthiopyrad |
| E-31 | (1-16) 2-(trifluoromethyl)-N-[2-(1,3,3-trimethylbutyl)phenyl]benzamide | (6-2) boscalid |
| E-32 | (1-16) 2-(trifluoromethyl)-N-[2-(1,3,3-trimethylbutyl)phenyl]benzamide | (6-6) fenhexamid |

TABLE 5-continued

Active compound combinations E

| No. | Carboxamide of the formula (I) | Carboxamide of the formula (V) |
|---|---|---|
| E-33 | (1-16) 2-(trifluoromethyl)-N-[2-(1,3,3-trimethylbutyl)phenyl]benzamide | (6-7) carpropamid |
| E-34 | (1-16) 2-(trifluoromethyl)-N-[2-(1,3,3-trimethylbutyl)phenyl]benzamide | (6-9) picobenzamid |
| E-35 | (1-16) 2-(trifluoromethyl)-N-[2-(1,3,3-trimethylbutyl)phenyl]benzamide | (6-14) penthiopyrad |

In addition to a carboxamide of the formula (I) (group 1), the active compound combinations F also comprise a dithiocarbamate (group 7) selected from (7-1) mancozeb
(7-2) maneb
(7-3) metiram
(7-4) propineb
(7-5) thiram
(7-6) zineb
(7-7) ziram Preference is given to active compound combinations F in which the dithiocarbamate (group 7) is selected from the list below:

(7-1) mancozeb
(7-2) maneb
(7-4) propineb
(7-5) thiram
(7-6) zineb

Particular preference is given to active compound combinations F in which the dithiocarbamate (group 7) is selected from the list below:

(7-1) mancozeb
(74) propineb

Emphasis is given to the active compound combinations F listed in Table 6 below:

In addition to a carboxamide of the formula (I) (group 1), the active compound combinations G also comprise an acylalanine of the formula (VI) (group 8)

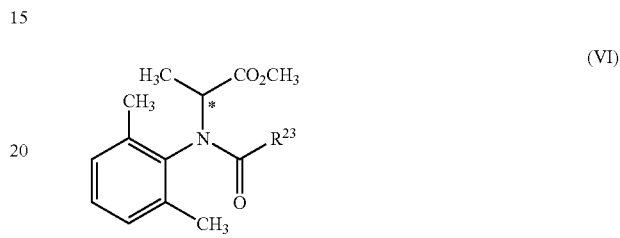

in which * and $R^{23}$ are as defined above.

Preference is given to active compound combinations G in which the acylalanine of the formula (VI) (group 8) is selected from the list below:

(8-1) benalaxyl
(8-2) furalaxyl
(8-3) metalaxyl
(8-4) metalaxyl-M
(8-5) benalaxyl-M Particular preference is given to active compound combinations G in which the acylalanine of the formula (VI) (group 8) is selected from the list below:

(8-3) metalaxyl
(8-4) metalaxyl-M
(8-5) benalaxyl-M

Emphasis is given to the active compound combinations G listed in Table 7 below:

TABLE 6

Active compound combinations F

| No. | Carboxamide of the formula (I) | Dithiocarbamate |
|---|---|---|
| F-1 | (1-2) N-[2-(1,3-dimethylbutyl)phenyl]-5-fluoro-1,3-dimethyl-1H-pyrazole-4-carboxamide | (7-1) mancozeb |
| F-2 | (1-2) N-[2-(1,3-dimethylbutyl)phenyl]-5-fluoro-1,3-dimethyl-1H-pyrazole-4-carboxamide | (7-4) propineb |
| F-3 | (1-8) 5-fluoro-1,3-dimethyl-N-[2-(1,3,3-trimethylbutyl)phenyl]-1H-pyrazole-4-carboxamide | (7-1) mancozeb |
| F-4 | (1-8) 5-fluoro-1,3-dimethyl-N-[2-(1,3,3-trimethylbutyl)phenyl]-1H-pyrazole-4-carboxamide | (7-4) propineb |
| F-5 | (1-10) 3-(trifluoromethyl)-1-methyl-N-[2-(1,3,3-trimethylbutyl)phenyl]-1H-pyrazole-4-carboxamide | (7-1) mancozeb |
| F-6 | (1-10) 3-(trifluoromethyl)-1-methyl-N-[2-(1,3,3-trimethylbutyl)phenyl]-1H-pyrazole-4-carboxamide | (7-4) propineb |
| F-7 | (1-13) N-[2-(1,3-dimethylbutyl)phenyl]-2-iodobenzamide | (7-1) mancozeb |
| F-8 | (1-13) N-[2-(1,3-dimethylbutyl)phenyl]-2-iodobenzamide | (7-4) propineb |
| F-9 | (1-14) 2-iodo-N-[2-(1,3,3-trimethylbutyl)phenyl]benzamide | (7-1) mancozeb |
| F-10 | (1-14) 2-iodo-N-[2-(1,3,3-trimethylbutyl)phenyl]benzamide | (7-4) propineb |
| F-11 | (1-15) N-[2-(1,3-dimethylbutyl)phenyl]-2-(trifluoromethyl)benzamide | (7-1) mancozeb |
| F-12 | (1-15) N-[2-(1,3-dimethylbutyl)phenyl]-2-(trifluoromethyl)benzamide | (7-4) propineb |
| F-13 | (1-16) 2-(trifluoromethyl)-N-[2-(1,3,3-trimethylbutyl)phenyl]benzamide | (7-1) mancozeb |
| F-14 | (1-16) 2-(trifluoromethyl)-N-[2-(1,3,3-trimethylbutyl)phenyl]benzamide | (7-4) propineb |

TABLE 7

Active compound combinations G

| No. | Carboxamide of the formula (I) | Acylalanine of the formula (VI) |
| --- | --- | --- |
| G-1 | (1-2) N-[2-(1,3-dimethylbutyl)phenyl]-5-fluoro-1,3-dimethyl-1H-pyrazole-4-carboxamide | (8-3) metalaxyl |
| G-2 | (1-2) N-[2-(1,3-dimethylbutyl)phenyl]-5-fluoro-1,3-dimethyl-1H-pyrazole-4-carboxamide | (8-4) metalaxyl-M |
| G-3 | (1-2) N-[2-(1,3-dimethylbutyl)phenyl]-5-fluoro-1,3-dimethyl-1H-pyrazole-4-carboxamide | (8-5) benalaxyl-M |
| G-4 | (1-8) 5-fluoro-1,3-dimethyl-N-[2-(1,3,3-trimethylbutyl)phenyl]-1H-pyrazole-4-carboxamide | (8-3) metalaxyl |
| G-5 | (1-8) 5-fluoro-1,3-dimethyl-N-[2-(1,3,3-trimethylbutyl)phenyl]-1H-pyrazole-4-carboxamide | (8-4) metalaxyl-M |
| G-6 | (1-8) 5-fluoro-1,3-dimethyl-N-[2-(1,3,3-trimethylbutyl)phenyl]-1H-pyrazole-4-carboxamide | (8-5) benalaxyl-M |
| G-7 | (1-10) 3-(trifluoromethyl)-1-methyl-N-[2-(1,3,3-trimethylbutyl)phenyl]-1H-pyrazole-4-carboxamide | (8-3) metalaxyl |
| G-8 | (1-10) 3-(trifluoromethyl)-1-methyl-N-[2-(1,3,3-trimethylbutyl)phenyl]-1H-pyrazole-4-carboxamide | (8-4) metalaxyl-M |
| G-9 | (1-10) 3-(trifluoromethyl)-1-methyl-N-[2-(1,3,3-trimethylbutyl)phenyl]-1H-pyrazole-4-carboxamide | (8-5) benalaxyl-M |
| G-10 | (1-13) N-[2-(1,3-dimethylbutyl)phenyl]-2-iodobenzamide | (8-3) metalaxyl |
| G-11 | (1-13) N-[2-(1,3-dimethylbutyl)phenyl]-2-iodobenzamide | (8-4) metalaxyl-M |
| G-12 | (1-13) N-[2-(1,3-dimethylbutyl)phenyl]-2-iodobenzamide | (8-5) benalaxyl-M |
| G-13 | (1-14) 2-iodo-N-[2-(1,3,3-trimethylbutyl)phenyl]benzamide | (8-3) metalaxyl |
| G-14 | (1-14) 2-iodo-N-[2-(1,3,3-trimethylbutyl)phenyl]benzamide | (8-4) metalaxyl-M |
| G-15 | (1-14) 2-iodo-N-[2-(1,3,3-trimethylbutyl)phenyl]benzamide | (8-5) benalaxyl-M |
| G-16 | (1-15) N-[2-(1,3-dimethylbutyl)phenyl]-2-(trifluoromethyl)-benzamide | (8-3) metalaxyl |
| G-17 | (1-15) N-[2-(1,3-dimethylbutyl)phenyl]-2-(trifluoromethyl)-benzamide | (8-4) metalaxyl-M |
| G-18 | (1-15) N-[2-(1,3-dimethylbutyl)phenyl]-2-(trifluoromethyl)-benzamide | (8-5) benalaxyl-M |
| G-19 | (1-16) 2-(trifluoromethyl)-N-[2-(1,3,3-trimethylbutyl)phenyl]-benzamide | (8-3) metalaxyl |
| G-20 | (1-16) 2-(trifluoromethyl)-N-[2-(1,3,3-trimethylbutyl)phenyl]-benzamide | (8-4) metalaxyl-M |
| G-21 | (1-16) 2-(trifluoromethyl)-N-[2-(1,3,3-trimethylbutyl)phenyl]-benzamide | (8-5) benalaxyl-M |

In addition to a carboxamide of the formula (I) (group 1), the active compound combinations H also comprise an anilinopyrimidine (group 9) selected from
(9-1) cyprodinil
(9-2) mepanipyrim
(9-3) pyrimethanil Emphasis is given to the active compound combinations H listed in Table 8 below:

TABLE 8

Active compound combinations H

| No. | Carboxamide of the formula (I) | Anilinopyrimidine |
| --- | --- | --- |
| H-1 | (1-2) N-[2-(1,3-dimethylbutyl)phenyl]-5-fluoro-1,3-dimethyl-1H-pyrazole-4-carboxamide | (9-1) cyprodinil |
| H-2 | (1-2) N-[2-(1,3-dimethylbutyl)phenyl]-5-fluoro-1,3-dimethyl-1H-pyrazole-4-carboxamide | (9-2) mepanipyrim |
| H-3 | (1-2) N-[2-(1,3-dimethylbutyl)phenyl]-5-fluoro-1,3-dimethyl-1H-pyrazole-4-carboxamide | (9-3) pyrimethanil |
| H-4 | (1-8) 5-fluoro-1,3-dimethyl-N-[2-(1,3,3-trimethylbutyl)phenyl]-1H-pyrazole-4-carboxamide | (9-1) cyprodinil |
| H-5 | (1-8) 5-fluoro-1,3-dimethyl-N-[2-(1,3,3-trimethylbutyl)phenyl]-1H-pyrazole-4-carboxamide | (9-2) mepanipyrim |
| H-6 | (1-8) 5-fluoro-1,3-dimethyl-N-[2-(1,3,3-trimethylbutyl)phenyl]-1H-pyrazole-4-carboxamide | (9-3) pyrimethanil |
| H-7 | (1-10) 3-(trifluoromethyl)-1-methyl-N-[2-(1,3,3-trimethylbutyl)phenyl]-1H-pyrazole-4-carboxamide | (9-1) cyprodinil |
| H-8 | (1-10) 3-(trifluoromethyl)-1-methyl-N-[2-(1,3,3-trimethylbutyl)phenyl]-1H-pyrazole-4-carboxamide | (9-2) mepanipyrim |
| H-9 | (1-10) 3-(trifluoromethyl)-1-methyl-N-[2-(1,3,3-trimethylbutyl)phenyl]-1H-pyrazole-4-carboxamide | (9-3) pyrimethanil |
| H-10 | (1-13) N-[2-(1,3-dimethylbutyl)phenyl]-2-iodobenzamide | (9-1) cyprodinil |

TABLE 8-continued

Active compound combinations H

| No. | Carboxamide of the formula (I) | Anilinopyrimidine |
|---|---|---|
| H-11 | (1-13) N-[2-(1,3-dimethylbutyl)phenyl]-2-iodobenzamide | (9-2) mepanipyrim |
| H-12 | (1-13) N-[2-(1,3-dimethylbutyl)phenyl]-2-iodobenzamide | (9-3) pyrimethanil |
| H-13 | (1-14) 2-iodo-N-[2-(1,3,3-trimethylbutyl)phenyl]benzamide | (9-1) cyprodinil |
| H-14 | (1-14) 2-iodo-N-[2-(1,3,3-trimethylbutyl)phenyl]benzamide | (9-2) mepanipyrim |
| H-15 | (1-14) 2-iodo-N-[2-(1,3,3-trimethylbutyl)phenyl]benzamide | (9-3) pyrimethanil |
| H-16 | (1-15) N-[2-(1,3-dimethylbutyl)phenyl]-2-(trifluoromethyl)benzamide | (9-1) cyprodinil |
| H-17 | (1-15) N-[2-(1,3-dimethylbutyl)phenyl]-2-(trifluoromethyl)benzamide | (9-2) mepanipyrim |
| H-18 | (1-15) N-[2-(1,3-dimethylbutyl)phenyl]-2-(trifluoromethyl)benzamide | (9-3) pyrimethanil |
| H-19 | (1-16) 2-(trifluoromethyl)-N-[2-(1,3,3-trimethylbutyl)phenyl]benzamide | (9-1) cyprodinil |
| H-20 | (1-16) 2-(trifluoromethyl)-N-[2-(1,3,3-trimethylbutyl)phenyl]benzamide | (9-2) mepanipyrim |
| H-21 | (1-16) 2-(trifluoromethyl)-N-[2-(1,3,3-trimethylbutyl)phenyl]benzamide | (9-3) pyrimethanil |

In addition to a carboxamide of the formula (I) (group 1), the active compound combinations I also comprise a benzimidazole of the formula (VIII) (group 10)

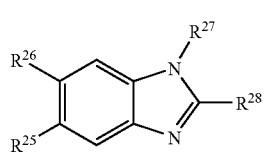

in which $R^{25}$, $R^{26}$, $R^{27}$ and $R^{28}$ are as defined above.

Preference is given to active compound combinations I in which the benzimidazole of the formula (VII) (group 10) is selected from the list below:

(10-1) 6-chloro-5-[(3,5-dimethylisoxazol-4-yl)sulphonyl]-2,2-difluoro-5H-[1,3]dioxolo[4,5-f]-benzimidazole
(10-2) benomyl
(10-3) carbendazim
(10-4) chlorfenazole
(10-5) fuberidazole
(10-6) thiabendazole Particular preference is given to active compound combinations I in which the benzimidazole of the formula (VIII) (group 10) is:

(10-3) carbendazim

Emphasis is given to the active compound combinations I listed in Table 9 below:

In addition to a carboxamide of the formula (I) (group 1), the active compound combinations J also comprise a carbamate (group 11) of the formula (IX).

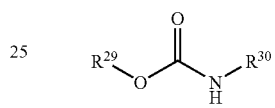

in which $R^{29}$ and $R^{30}$ are as defined above.

Preference is given to active compound combinations J in which the carbamate (group 11) is selected from the list below:

(11-1) diethofencarb (11-2) propamocarb (11-3) propamocarb-hydrochloride (11-4) propamocarb-fosetyl Emphasis is given to the active compound combinations J listed in Table 10 below:

TABLE 9

Active compound combinations I

| No. | Carboxamide of the formula (I) | Benzimidazole of the formula (VIII) |
|---|---|---|
| I-1 | (1-2) N-[2-(1,3-dimethylbutyl)phenyl]-5-fluoro-1,3-dimethyl-1H-pyrazole-4-carboxamide | (10-3) carbendazim |
| I-2 | (1-8) 5-fluoro-1,3-dimethyl-N-[2-(1,3,3-trimethylbutyl)phenyl]-1H-pyrazole-4-carboxamide | (10-3) carbendazim |
| I-3 | (1-10) 3-(trifluoromethyl)-1-methyl-N-[2-(1,3,3-trimethylbutyl)phenyl]-1H-pyrazole-4-carboxamide | (10-3) carbendazim |
| I-4 | (1-13) N-[2-(1,3-dimethylbutyl)phenyl]-2-iodobenzamide | (10-3) carbendazim |
| I-5 | (1-14) 2-iodo-N-[2-(1,3,3-trimethylbutyl)phenyl]benzamide | (10-3) carbendazim |
| I-6 | (1-15) N-[2-(1,3-dimethylbutyl)phenyl]-2-(trifluoromethyl)benzamide | (10-3) carbendazim |
| I-7 | (1-16) 2-(trifluoromethyl)-N-[2-(1,3,3-trimethylbutyl)phenyl]benzamide | (10-3) carbendazim |

TABLE 10

Active compound combinations J

| No. | Carboxamide of the formula (I) | Carbamate of the formula (IX) |
|---|---|---|
| J-1 | (1-2) N-[2-(1,3-dimethylbutyl)phenyl]-5-fluoro-1,3-dimethyl-1H-pyrazole-4-carboxamide | (11-2) propamocarb |
| J-2 | (1-2) N-[2-(1,3-dimethylbutyl)phenyl]-5-fluoro-1,3-dimethyl-1H-pyrazole-4-carboxamide | (11-3) propamocarb-hydrochloride |
| J-3 | (1-2) N-[2-(1,3-dimethylbutyl)phenyl]-5-fluoro-1,3-dimethyl-1H-pyrazole-4-carboxamide | (11-4) propamocarb-fosetyl |
| J-4 | (1-8) 5-fluoro-1,3-dimethyl-N-[2-(1,3,3-trimethylbutyl)phenyl]-1H-pyrazole-4-carboxamide | (11-2) propamocarb |
| J-5 | (1-8) 5-fluoro-1,3-dimethyl-N-[2-(1,3,3-trimethylbutyl)phenyl]-1H-pyrazole-4-carboxamide | (11-3) propamocarb-hydrochloride |
| J-6 | (1-8) 5-fluoro-1,3-dimethyl-N-[2-(1,3,3-trimethylbutyl)phenyl]-1H-pyrazole-4-carboxamide | (11-4) propamocarb-fosetyl |
| J-7 | (1-10) 3-(trifluoromethyl)-1-methyl-N-[2-(1,3,3-trimethylbutyl)phenyl]-1H-pyrazole-4-carboxamide | (11-2) propamocarb |
| J-8 | (1-10) 3-(trifluoromethyl)-1-methyl-N-[2-(1,3,3-trimethylbutyl)phenyl]-1H-pyrazole-4-carboxamide | (11-3) propamocarb-hydrochloride |
| J-9 | (1-10) 3-(trifluoromethyl)-1-methyl-N-[2-(1,3,3-trimethylbutyl)phenyl]-1H-pyrazole-4-carboxamide | (11-4) propamocarb-fosetyl |
| J-10 | (1-13) N-[2-(1,3-dimethylbutyl)phenyl]-2-iodobenzamide | (11-2) propamocarb |
| J-11 | (1-13) N-[2-(1,3-dimethylbutyl)phenyl]-2-iodobenzamide | (11-3) propamocarb-hydrochloride |
| J-12 | (1-13) N-[2-(1,3-dimethylbutyl)phenyl]-2-iodobenzamide | (11-4) propamocarb-fosetyl |
| J-13 | (1-14) 2-iodo-N-[2-(1,3,3-trimethylbutyl)phenyl]benzamide | (11-2) propamocarb |
| J-14 | (1-14) 2-iodo-N-[2-(1,3,3-trimethylbutyl)phenyl]benzamide | (11-3) propamocarb-hydrochloride |
| J-15 | (1-14) 2-iodo-N-[2-(1,3,3-trimethylbutyl)phenyl]benzamide | (11-4) propamocarb-fosetyl |
| J-16 | (1-15) N-[2-(1,3-dimethylbutyl)phenyl]-2-(trifluoromethyl)benzamide | (11-2) propamocarb |
| J-17 | (1-15) N-[2-(1,3-dimethylbutyl)phenyl]-2-(trifluoromethyl)-benzamide | (11-3) propamocarb-hydrochloride |
| J-18 | (1-15) N-[2-(1,3-dimethylbutyl)phenyl]-2-(trifluoromethyl)-benzamide | (11-4) propamocarb-fosetyl |
| J-19 | (1-16) 2-(trifluoromethyl)-N-[2-(1,3,3-trimethylbutyl)phenyl]-benzamide | (11-2) propamocarb |
| J-20 | (1-16) 2-(trifluoromethyl)-N-[2-(1,3,3-trimethylbutyl)phenyl]-benzamide | (11-3) propamocarb-hydrochloride |
| J-21 | (1-16) 2-(trifluoromethyl)-N-[2-(1,3,3-trimethylbutyl)phenyl]-benzamide | (11-4) propamocarb-fosetyl |

In addition to a carboxamide of the formula (I) (group 1), the active compound combinations K also comprise a dicarboximide (group 12) selected from
(12-1) captafol
(12-2) captan
(12-3) folpet
(12-4) iprodione
(12-5) procymidone
(12-6) vinclozolin Preference is given to active compound combinations K in which the dicarboximide (group 12) is selected from the list below:
(12-2) captan
(12-3) folpet
(12-4) iprodione Emphasis is given to the active compound combinations K listed in Table 11 below:

TABLE 11

Active compound combinations K

| No. | Carboxamide of the formula (I) | Dicarboximide |
|---|---|---|
| K-1 | (1-2) N-[2-(1,3-dimethylbutyl)phenyl]-5-fluoro-1,3-dimethyl-1H-pyrazole-4-carboxamide | (12-2) captan |
| K-2 | (1-2) N-[2-(1,3-dimethylbutyl)phenyl]-5-fluoro-1,3-dimethyl-1H-pyrazole-4-carboxamide | (12-3) folpet |
| K-3 | (1-2) N-[2-(1,3-dimethylbutyl)phenyl]-5-fluoro-1,3-dimethyl-1H-pyrazole-4-carboxamide | (12-4) iprodione |
| K-4 | (1-8) 5-fluoro-1,3-dimethyl-N-[2-(1,3,3-trimethylbutyl)phenyl]-1H-pyrazole-4-carboxamide | (12-2) captan |
| K-5 | (1-8) 5-fluoro-1,3-dimethyl-N-[2-(1,3,3-trimethylbutyl)phenyl]-1H-pyrazole-4-carboxamide | (12-3) folpet |
| K-6 | (1-8) 5-fluoro-1,3-dimethyl-N-[2-(1,3,3-trimethylbutyl)phenyl]-1H-pyrazole-4-carboxamide | (12-4) iprodione |
| K-7 | (1-10) 3-(trifluoromethyl)-1-methyl-N-[2-(1,3,3-trimethylbutyl)phenyl]-1H-pyrazole-4-carboxamide | (12-2) captan |

TABLE 11-continued

Active compound combinations K

| No. | Carboxamide of the formula (I) | Dicarboximide |
| --- | --- | --- |
| K-8 | (1-10) 3-(trifluoromethyl)-1-methyl-N-[2-(1,3,3-trimethylbutyl)phenyl]-1H-pyrazole-4-carboxamide | (12-3) folpet |
| K-9 | (1-10) 3-(trifluoromethyl)-1-methyl-N-[2-(1,3,3-trimethylbutyl)phenyl]-1H-pyrazole-4-carboxamide | (12-4) iprodione |
| K-10 | (1-13) N-[2-(1,3-dimethylbutyl)phenyl]-2-iodobenzamide | (12-2) captan |
| K-11 | (1-13) N-[2-(1,3-dimethylbutyl)phenyl]-2-iodobenzamide | (12-3) folpet |
| K-12 | (1-13) N-[2-(1,3-dimethylbutyl)phenyl]-2-iodobenzamide | (12-4) iprodione |
| K-13 | (1-14) 2-iodo-N-[2-(1,3,3-trimethylbutyl)phenyl]benzamide | (12-2) captan |
| K-14 | (1-14) 2-iodo-N-[2-(1,3,3-trimethylbutyl)phenyl]benzamide | (12-3) folpet |
| K-15 | (1-14) 2-iodo-N-[2-(1,3,3-trimethylbutyl)phenyl]benzamide | (12-4) iprodione |
| K-16 | (1-15) N-[2-(1,3-dimethylbutyl)phenyl]-2-(trifluoromethyl)benzamide | (12-2) captan |
| K-17 | (1-15) N-[2-(1,3-dimethylbutyl)phenyl]-2-(trifluoromethyl)benzamide | (12-3) folpet |
| K-18 | (1-15) N-[2-(1,3-dimethylbutyl)phenyl]-2-(trifluoromethyl)benzamide | (12-4) iprodione |
| K-19 | (1-16) 2-(trifluoromethyl)-N-[2-(1,3,3-trimethylbutyl)phenyl]benzamide | (12-2) captan |
| K-20 | (1-16) 2-(trifluoromethyl)-N-[2-(1,3,3-trimethylbutyl)phenyl]benzamide | (12-3) folpet |
| K-21 | (1-16) 2-(trifluoromethyl)-N-[2-(1,3,3-trimethylbutyl)phenyl]benzamide | (12-4) iprodione |

In addition to a carboxamide of the formula (I) (group 1), the active compound combinations L also comprise a guanidine (group 13) selected from (13-1) dodine
(13-2) guazatine
(13-3) iminoctadine triacetate
(13-4) iminoctadine tris(albesilate)

Preference is given to active compound combinations L in which the guanidine (group 13) is selected from the list below:

(13-1) dodine
(13-2) guazatine

Emphasis is given to the active compound combinations L listed in Table 12 below:

In addition to a carboxamide of the formula (I) (group 1), the active compound combinations M also comprise an imidazole (group 14) selected from (14-1) cyazofamid
(14-2) prochloraz
(14-3) triazoxide
(14-4) pefurazoate Preference is given to active compound combinations M in which the imidazole (group 14) is selected from the list below:

(14-2) prochloraz
(14-3) triazoxide

Emphasis is given to the active compound combinations M listed in Table 13 below:

TABLE 12

Active compound combinations L

| No. | Carboxamide of the formula (I) | Guanidine |
| --- | --- | --- |
| L-1 | (1-2) N-[2-(1,3-dimethylbutyl)phenyl]-5-fluoro-1,3-dimethyl-1H-pyrazole-4-carboxamide | (13-1) dodine |
| L-2 | (1-2) N-[2-(1,3-dimethylbutyl)phenyl]-5-fluoro-1,3-dimethyl-1H-pyrazole-4-carboxamide | (13-2) guazatine |
| L-3 | (1-8) 5-fluoro-1,3-dimethyl-N-[2-(1,3,3-trimethylbutyl)phenyl]-1H-pyrazole-4-carboxamide | (13-1) dodine |
| L-4 | (1-8) 5-fluoro-1,3-dimethyl-N-[2-(1,3,3-trimethylbutyl)phenyl]-1H-pyrazole-4-carboxamide | (13-2) guazatine |
| L-5 | (1-10) 3-(trifluoromethyl)-1-methyl-N-[2-(1,3,3-trimethylbutyl)phenyl]-1H-pyrazole-4-carboxamide | (13-1) dodine |
| L-6 | (1-10) 3-(trifluoromethyl)-1-methyl-N-[2-(1,3,3-trimethylbutyl)phenyl]-1H-pyrazole-4-carboxamide | (13-2) guazatine |
| L-7 | (1-13) N-[2-(1,3-dimethylbutyl)phenyl]-2-iodobenzamide | (13-1) dodine |
| L-8 | (1-13) N-[2-(1,3-dimethylbutyl)phenyl]-2-iodobenzamide | (13-2) guazatine |
| L-9 | (1-14) 2-iodo-N-[2-(1,3,3-trimethylbutyl)phenyl]benzamide | (13-1) dodine |
| L-10 | (1-14) 2-iodo-N-[2-(1,3,3-trimethylbutyl)phenyl]benzamide | (13-2) guazatine |
| L-11 | (1-15) N-[2-(1,3-dimethylbutyl)phenyl]-2-(trifluoromethyl)benzamide | (13-1) dodine |
| L-12 | (1-15) N-[2-(1,3-dimethylbutyl)phenyl]-2-(trifluoromethyl)benzamide | (13-2) guazatine |
| L-13 | (1-16) 2-(trifluoromethyl)-N-[2-(1,3,3-trimethylbutyl)phenyl]benzamide | (13-1) dodine |
| L-14 | (1-16) 2-(trifluoromethyl)-N-[2-(1,3,3-trimethylbutyl)phenyl]benzamide | (13-2) guazatine |

TABLE 13

Active compound combinations M

| No. | Carboxamide of the formula (I) | Imidazole |
|---|---|---|
| M-1 | (1-2) N-[2-(1,3-dimethylbutyl)phenyl]-5-fluoro-1,3-dimethyl-1H-pyrazole-4-carboxamide | (14-2) prochloraz |
| M-2 | (1-2) N-[2-(1,3-dimethylbutyl)phenyl]-5-fluoro-1,3-dimethyl-1H-pyrazole-4-carboxamide | (14-3) triazoxide |
| M-3 | (1-8) 5-fluoro-1,3-dimethyl-N-[2-(1,3,3-trimethylbutyl)phenyl]-1H-pyrazole-4-carboxamide | (14-2) prochloraz |
| M-4 | (1-8) 5-fluoro-1,3-dimethyl-N-[2-(1,3,3-trimethylbutyl)phenyl]-1H-pyrazole-4-carboxamide | (14-3) triazoxide |
| M-5 | (1-10) 3-(trifluoromethyl)-1-methyl-N-[2-(1,3,3-trimethylbutyl)phenyl]-1H-pyrazole-4-carboxamide | (14-2) prochloraz |
| M-6 | (1-10) 3-(trifluoromethyl)-1-methyl-N-[2-(1,3,3-trimethylbutyl)phenyl]-1H-pyrazole-4-carboxamide | (14-3) triazoxide |
| M-7 | (1-13) N-[2-(1,3-dimethylbutyl)phenyl]-2-iodobenzamide | (14-2) prochloraz |
| M-8 | (1-13) N-[2-(1,3-dimethylbutyl)phenyl]-2-iodobenzamide | (14-3) triazoxide |
| M-9 | (1-14) 2-iodo-N-[2-(1,3,3-trimethylbutyl)phenyl]benzamide | (14-2) prochloraz |
| M-10 | (1-14) 2-iodo-N-[2-(1,3,3-trimethylbutyl)phenyl]benzamide | (14-3) triazoxide |
| M-11 | (1-15) N-[2-(1,3-dimethylbutyl)phenyl]-2-(trifluoromethyl)benzamide | (14-2) prochloraz |
| M-12 | (1-15) N-[2-(1,3-dimethylbutyl)phenyl]-2-(trifluoromethyl)benzamide | (14-3) triazoxide |
| M-13 | (1-16) 2-(trifluoromethyl)-N-[2-(1,3,3-trimethylbutyl)phenyl]benzamide | (14-2) prochloraz |
| M-14 | (1-16) 2-(trifluoromethyl)-N-[2-(1,3,3-trimethylbutyl)phenyl]benzamide | (14-3) triazoxide |

In addition to a carboxamide of the formula (I) (group 1), the active compound combinations N also comprise a morpholine (group 15) of the formula (X)

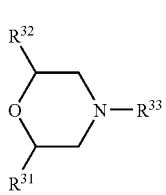

(X)

in which $R^{31}$, $R^{32}$ and $R^{33}$ are as defined above.

Preference is given to active compound combinations N in which the morpholine (group 15) of the formula (x) is selected from the list below:
(15-1) aldimorph
(15-2) tridemorph
(15-3) dodemorph
(15-4) fenpropimorph
(15-5) dimethomorph Particular preference is given to active compound combinations N in which the morpholine (group 15) of the formula (X) is selected from the list below:
(15-4) fenpropimorph
(15-5) dimethomorph Emphasis is given to the active compound combinations N listed in Table 14 below:

In addition to a carboxamide of the formula (I) (group 1), the active compound combinations O also comprise a pyrrole (group 16) of the formula (XI)

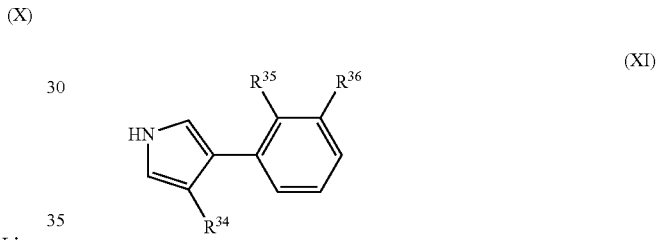

(XI)

in which $R^3$, $R^{35}$ and $R^{36}$ are as defined above.

Preference is given to active compound combinations 0 in which the pyrrole (group 16) of the formula (XI) is selected from the list below:
(16-1) fenpiclonil
(16-2) fludioxonil
(16-3) pyrrolnitrin Particular preference is given to active compound combinations 0 in which the pyrrole (group 16) of the formula (XI) is selected from the list below:
(16-2) fludioxonil Emphasis is given to the active compound combinations O listed in Table 15 below:

TABLE 14

Active compound combinations N

| No. | Carboxamide of the formula (I) | Morpholine of the formula (X) |
|---|---|---|
| N-1 | (1-2) N-[2-(1,3-dimethylbutyl)phenyl]-5-fluoro-1,3-dimethyl-1H-pyrazole-4-carboxamide | (15-4) fenpropimorph |
| N-2 | (1-8) 5-fluoro-1,3-dimethyl-N-[2-(1,3,3-trimethylbutyl)phenyl]-1H-pyrazole-4-carboxamide | (15-4) fenpropimorph |
| N-3 | (1-10) 3-(trifluoromethyl)-1-methyl-N-[2-(1,3,3-trimethylbutyl)phenyl]-1H-pyrazole-4-carboxamide | (15-4) fenpropimorph |
| N-4 | (1-13) N-[2-(1,3-dimethylbutyl)phenyl]-2-iodobenzamide | (15-4) fenpropimorph |
| N-5 | (1-14) 2-iodo-N-[2-(1,3,3-trimethylbutyl)phenyl]benzamide | (15-4) fenpropimorph |
| N-6 | (1-15) N-[2-(1,3-dimethylbutyl)phenyl]-2-(trifluoromethyl)-benzamide | (15-4) fenpropimorph |
| N-7 | (1-16) 2-(trifluoromethyl)-N-[2-(1,3,3-trimethylbutyl)phenyl]-benzamide | (15-4) fenpropimorph |

TABLE 15

Active compound combinations O

| No. | Carboxamide of the formula (I) | Pyrrole of the formula (XI) |
|---|---|---|
| O-1 | (1-2) N-[2-(1,3-dimethylbutyl)phenyl]-5-fluoro-1,3-dimethyl-1H-pyrazole-4-carboxamide | (16-2) fludioxonil |
| O-2 | (1-8) 5-fluoro-1,3-dimethyl-N-[2-(1,3,3-trimethylbutyl)phenyl]-1H-pyrazole-4-carboxamide | (16-2) fludioxonil |
| O-3 | (1-10) 3-(trifluoromethyl)-1-methyl-N-[2-(1,3,3-trimethylbutyl)-phenyl]-1H-pyrazole-4-carboxamide | (16-2) fludioxonil |
| O-4 | (1-13) N-[2-(1,3-dimethylbutyl)phenyl]-2-iodobenzamide | (16-2) fludioxonil |
| O-5 | (1-14) 2-iodo-N-[2-(1,3,3-trimethylbutyl)phenyl]benzamide | (16-2) fludioxonil |
| O-6 | (1-15) N-[2-(1,3-dimethylbutyl)phenyl]-2-(trifluoromethyl)benzamide | (16-2) fludioxonil |
| O-7 | (1-16) 2-(trifluoromethyl)-N-[2-(1,3,3-trimethylbutyl)phenyl]-benzamide | (16-2) fludioxonil |

In addition to a carboxamide of the formula (I) (group 1), the active compound combinations P also comprise a phosphonate (group 17) selected from
(17-1) fosetyl-Al
(17-2) phosphonic acid Emphasis is given to the active compound combinations P listed in Table 16 below:

TABLE 16

Active compound combinations P

| No. | Carboxamide of the formula (I) | Phosphonate |
|---|---|---|
| P-1 | (1-2) N-[2-(1,3-dimethylbutyl)phenyl]-5-fluoro-1,3-dimethyl-1H-pyrazole-4-carboxamide | (17-1) fosetyl-Al |
| P-2 | (1-8) 5-fluoro-1,3-dimethyl-N-[2-(1,3,3-trimethylbutyl)phenyl]-1H-pyrazole-4-carboxamide | (17-1) fosetyl-Al |
| P-3 | (1-10) 3-(trifluoromethyl)-1-methyl-N-[2-(1,3,3-trimethylbutyl)-phenyl]-1H-pyrazole-4-carboxamide | (17-1) fosetyl-Al |
| P-4 | (1-13) N-[2-(1,3-dimethylbutyl)phenyl]-2-iodobenzamide | (17-1) fosetyl-Al |
| P-5 | (1-14) 2-iodo-N-[2-(1,3,3-trimethylbutyl)phenyl]benzamide | (17-1) fosetyl-Al |
| P-6 | (1-15) N-[2-(1,3-dimethylbutyl)phenyl]-2-(trifluoromethyl)benzamide | (17-1) fosetyl-Al |
| P-7 | (1-16) 2-(trifluoromethyl)-N-[2-(1,3,3-trimethylbutyl)phenyl]-benzamide | (17-1) fosetyl-Al |

In addition to a carboxamide of the formula (I) (group 1), the active compound combinations Q also comprise a fungicide (group 19) selected from
(19-1) acibenzolar-S-methyl
(19-2) chlorothalonil
(19-3) cymoxanil
(19-4) edifenphos
(19-5) famoxadone
(19-6) fluazinam
(19-7) copper oxychloride
(19-8) copper hydroxide
(19-9) oxadixyl
(19-10) spiroxamine
(19-11) dithianon
(19-12) metrafenone
(19-13) fenamidone
(19-14) 2,3-dibutyl-6-chlorothieno[2,3-d]pyrimidin-4(3H)-one
(19-15) probenazole
(19-16) isoprothiolane
(19-17) kasugamycin
(19-18) phthalide
(19-19) ferimzone
(19-20) tricyclazole
(19-21) N-({4-[(cyclopropylamino)carbonyl]phenyl}sulphonyl)-2-methoxybenzamide
(19-22) 2-(4-chlorophenyl)-N-{2-[3-methoxy-4-prop-2-yn-1-yloxy)phenyl]ethyl}-2-(prop-2-yn-1-yloxy)acetamide Preference is given to active compound combinations Q in which the fungicide (group 19) is selected from the list below:
(19-1) acibenzolar-S-methyl
(19-2) chlorothalonil
(19-3) cymoxanil
(19-5) famoxadone
(19-6) fluazinam
(19-7) copper oxychloride
(19-9) oxadixyl
(19-10) spiroxamine
(19-13) fenamidone
(19-21) N-({4-[(cyclopropylamino)carbonyl]phenyl}sulphonyl)-2-methoxybenzamide
(19-22) 2-(4-chlorophenyl)-N-{2-[3-methoxy-4-(prop-2-yn-1-yloxy)phenyl]ethyl}-2-(prop-2-yn-1-yloxy)acetamide Particular preference is given to active compound combinations Q in which the fungicide (group 19) is selected from the following list:
(19-2) chlorothalonil
(19-7) copper oxychloride
(19-10) spiroxamine
(19-21) N-({4-[(cyclopropylamino)carbonyl]phenyl}sulphonyl)-2-methoxybenzamide
(19-22) 2-(4-chlorophenyl)-N-{2-[3-methoxy-4-(prop-2-yn-1-yloxy)phenyl]ethyl}-2-(prop-2-yn-1-yloxy)acetamide Emphasis is given to the active compound combinations Q listed in Table 17 below:

TABLE 17

| | Active compound combinations Q | |
|---|---|---|
| No. | Carboxamide of the formula (I) | Fungicide |
| Q-1 | (1-2) N-[2-(1,3-dimethylbutyl)phenyl]-5-fluoro-1,3-dimethyl-1H-pyrazole-4-carboxamide | (19-2) chlorothalonil |
| Q-2 | (1-2) N-[2-(1,3-dimethylbutyl)phenyl]-5-fluoro-1,3-dimethyl-1H-pyrazole-4-carboxamide | (19-7) copper oxychloride |
| Q-3 | (1-2) N-[2-(1,3-dimethylbutyl)phenyl]-5-fluoro-1,3-dimethyl-1H-pyrazole-4-carboxamide | (19-10) spiroxamine |
| Q-4 | (1-2) N-[2-(1,3-dimethylbutyl)phenyl]-5-fluoro-1,3-dimethyl-1H-pyrazole-4-carboxamide | (19-21) N-({4-[(cyclopropylamino)carbonyl]-phenyl}sulphonyl)-2-methoxybenzamide |
| Q-5 | (1-2) N-[2-(1,3-dimethylbutyl)phenyl]-5-fluoro-1,3-dimethyl-1H-pyrazole-4-carboxamide | (19-22) 2-(4-chlorophenyl)-N-{2-[3-methoxy-4-(prop-2-yn-1-yloxy)phenyl]ethyl}-2-(prop-2-yn-1-yloxy)acetamide |
| Q-6 | (1-8) 5-fluoro-1,3-dimethyl-N-[2-(1,3,3-trimethylbutyl)phenyl]-1H-pyrazole-4-carboxamide | (19-2) chlorothalonil |
| Q-7 | (1-8) 5-fluoro-1,3-dimethyl-N-[2-(1,3,3-trimethylbutyl)phenyl]-1H-pyrazole-4-carboxamide | (19-7) copper oxychloride |
| Q-8 | (1-8) 5-fluoro-1,3-dimethyl-N-[2-(1,3,3-trimethylbutyl)phenyl]-1H-pyrazole-4-carboxaxmide | (19-10) spiroxamine |
| Q-9 | (1-8) 5-fluoro-1,3-dimethyl-N-[2-(1,3,3-trimethylbutyl)phenyl]-1H-pyrazole-4-carboxamide | (19-21) N-({4-[(cyclopropylamino)carbonyl]-phenyl}sulphonyl)-2-methoxybenzamide |
| Q-10 | (1-8) 5-fluoro-1,3-dimethyl-N-[2-(1,3,3-trimethylbutyl)phenyl]-1H-pyrazole-4-carboxamide | (19-22) 2-(4-chlorophenyl)-N-{2-[3-methoxy-4-(prop-2-yn-1-yloxy)phenyl]ethyl}-2-(prop-2-yn-1-yloxy)acetamide |
| Q-11 | (1-10) 3-(trifluoromethyl)-1-methyl-N-[2-(1,3,3-trimethylbutyl)phenyl]-1H-pyrazole-4-carboxamide | (19-2) chlorothalonil |
| Q-12 | (1-10) 3-(trifluoromethyl)-1-methyl-N-[2-(1,3,3-trimethylbutyl)phenyl]-1H-pyrazole-4-carboxamide | (19-7) copper oxychloride |
| Q-13 | (1-10) 3-(trifluoromethyl)-1-methyl-N-[2-(1,3,3-trimethylbutyl)phenyl]-1H-pyrazole-4-carboxamide | (19-10) spiroxamine |
| Q-14 | (1-10) 3-(trifluoromethyl)-1-methyl-N-[2-(1,3,3-trimethylbutyl)phenyl]-1H-pyrazole-4-carboxamide | (19-21) N-({4-[(cyclopropylamino)carbonyl]-phenyl}sulphonyl)-2-methoxybenzamide |
| Q-15 | (1-10) 3-(trifluoromethyl)-1-methyl-N-[2-(1,3,3-trimethylbutyl)phenyl]-1H-pyrazole-4-carboxamide | (19-22) 2-(4-chlorophenyl)-N-{2-[3-methoxy-4-(prop-2-yn-1-yloxy)phenyl]ethyl}-2-(prop-2-yn-1-yloxy)acetamide |
| Q-16 | (1-13) N-[2-(1,3-dimethylbutyl)phenyl]-2-iodobenzamide | (19-2) chlorothalonil |
| Q-17 | (1-13) N-[2-(1,3-dimethylbutyl)phenyl]-2-iodobenzamide | (19-7) copper oxychloride |
| Q-18 | (1-13) N-[2-(1,3-dimethylbutyl)phenyl]-2-iodobenzamide | (19-10) spiroxamine |
| Q-19 | (1-13) N-[2-(1,3-dimethylbutyl)phenyl]-2-iodobenzamide | (19-21) N-({4-[(cyclopropylamino)carbonyl]-phenyl}sulphonyl)-2-methoxybenzamide |
| Q-20 | (1-13) N-[2-(1,3-dimethylbutyl)phenyl]-2-iodobenzamide | (19-22) 2-(4-chlorophenyl)-N-{2-[3-methoxy-4-(prop-2-yn-1-yloxy)phenyl]ethyl}-2-(prop-2-yn-1-yloxy)acetamide |
| Q-21 | (1-14) 2-iodo-N-[2-(1,3,3-trimethylbutyl)-phenyl]benzamide | (19-2) chlorothalonil |
| Q-22 | (1-14) 2-iodo-N-[2-(1,3,3-trimethylbutyl)-phenyl]benzamide | (19-7) copper oxychloride |
| Q-23 | (1-14) 2-iodo-N-[2-(1,3,3-trimethylbutyl)-phenyl]benzamide | (19-10) spiroxamine |
| Q-24 | (1-14) 2-iodo-N-[2-(1,3,3-trimethylbutyl)-benyl]benzamide | (19-21) N-({4-[(cyclopropylamino)carbonyl]-phenyl}sulphonyl)-2-methoxybenzamide |
| Q-25 | (1-14) 2-iodo-N-[2-(1,3,3-trimethylbutyl)-phenyl]benzamide | (19-22) 2-(4-chlorophenyl)-N-{2-[3-methoxy-4-(prop-2-yn-1-yloxy)phenyl]ethyl}-2-(prop-2-yn-1-yloxy)acetamide |
| Q-26 | (1-15) N-[2-(1,3-dimethylbutyl)phenyl]-2-(trifluoromethyl)benzamide | (19-2) chlorothalonil |
| Q-27 | (1-15) N-[2-(1,3-dimethylbutyl)phenyl]-2-(trifluoromethyl)benzamide | (19-7) copper oxychloride |
| Q-28 | (1-15) N-[2-(1,3-dimethylbutyl)phenyl]-2-(trifluoromethyl)benzamide | (19-10) spiroxamine |
| Q-29 | (1-15) N-[2-(1,3-dimethylbutyl)phenyl]-2-(trifluoromethyl)benzamide | (19-21) N-({4-[(cyclopropylamino)carbonyl]-phenyl}sulphonyl)-2-methoxybenzamide |

TABLE 17-continued

Active compound combinations Q

| No. | Carboxamide of the formula (I) | Fungicide |
|---|---|---|
| Q-30 | (1-15) N-[2-(1,3-dimethylbutyl)phenyl]-2-(trifluoromethyl)benzamide | (19-22) 2-(4-chlorophenyl)-N-{2-[3-methoxy-4-(prop-2-yn-1-yloxy)phenyl]ethyl}-2-(prop-2-yn-1-yloxy)acetamide |
| Q-31 | (1-16) 2-(trifluoromethyl)-N-[2-(1,3,3-trimethylbutyl)phenyl]benzamide | (19-2) chlorothalonil |
| Q-32 | (1-16) 2-(trifluorometihyl)-N-[2-(1,3,3-trimethylbutyl)phenyl]benzamide | (19-7) copper oxychloride |
| Q-33 | (1-16) 2-trifluoromethyl)-N-[2-(1,3,3-trimethylbutyl)phenyl]benzamide | (19-10) spiroxamine |
| Q-34 | (1-16) 2-(trifluoromethyl)-N-[2-(1,3,3-trimethylbutyl)phenyl]benzamide | (19-21) N-({4-[(cyclopropylamino)carbonyl]phenyl}sulphonyl)-2-methoxybenzamide |
| Q-35 | (1-16) 2-(trifluoromethyl)-N-[2-(1,3,3-trimethylbutyl)phenyl]benzamide | (19-22) 2-(4-chlorophenyl)-N-{2-[3-methoxy-4-(prop-2-yn-1-yloxy)phenyl]ethyl}-2-(prop-2-yn-1-yloxy)acetamide |

In addition to a carboxamide of the formula (I) (group 1), the active compound combinations R also comprise a (thio)urea derivative (group 20) selected from
(20-1) pencycuron
(20-2) thiophanate-methyl
(20-3) thiophanate-ethyl Preference is given to active compound combinations R in which the (thio)urea derivative (group 20) is selected from the list below:
(20-1) pencycuron
(20-2) thiophanate-methyl Emphasis is given to the active compound combinations R listed in Table 18 below:

TABLE 18

Active compound combinations R

| No. | Carboxamide of the formula (I) | (Thio)urea derivative |
|---|---|---|
| R-1 | (1-2) N-[2-(1,3-dimethylbutyl)phenyl]-5-fluoro-1,3-dimethyl-1H-pyrazole-4-carboxamide | (20-1) pencycuron |
| R-2 | (1-8) 5-fluoro-1,3-dimethyl-N-[2-(1,3,3-trimethylbutyl)phenyl]-1H-pyrazole-4-carboxamide | (20-1) pencycuron |
| R-3 | (1-10) 3-(trifluoromethyl)-1-methyl-N-[2-(1,3,3-trimethylbutyl)phenyl]-1H-pyrazole-4-carboxamide | (20-1) pencycuron |
| R-4 | (1-13) N-[2-(1,3-dimethylbutyl)phenyl]-2-iodobenzamide | (20-1) pencycuron |
| R-5 | (1-14) 2-iodo-N-[2-(1,3,3-trimethylbutyl)phenyl]benzamide | (20-1) pencycuron |
| R-6 | (1-15) N-[2-(1,3-dimethylbutyl)phenyl]-2-(trifluoromethyl)benzamide | (20-1) pencycuron |
| R-7 | (1-16) 2-(trifluoromethyl)-N-[2-(1,3,3-trimethylbutyl)phenyl]benzamide | (20-1) pencycuron |

In addition to a carboxamide of the formula (I) (group 1), the active compound combinations S also comprise a triazolopyrimidine (group 22) of the formula (XIV)

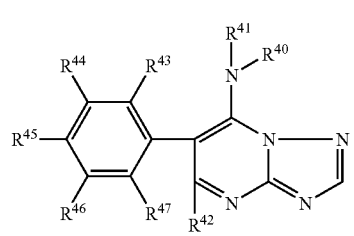

(XIV)

in which $R^{40}$, $R^{41}$, $R^{42}$, $R^{43}$, $R^{44}$, $R^{45}$, $R^{46}$ and $R^{47}$ are as defined above.

Preference is given to active compound combinations S in which the triazolopyrimidine (group 22) of the formula (XIV) is selected from the list below:

(22-1) 5-chloro-N-[(1S)-2,2,2-trifluoro-1-methylethyl]-6-(2,4,6-trifluorophenyl)[1,2,4]triazolo-[1,5-a]pyrimidine-7-amine (22-2) 5-chloro-N-[(1R)—1,2-dimethylpropyl]-6-(2,4,6-trifluorophenyl)[1,2,4]triazolo[1,5-a]-pyrimidine-7-amine (22-3) 5-chloro-6-(2-chloro-6-fluorophenyl)$_{7-4}$-methylpiperidin-1-yl)[1,2,4]triazolo[1,5-a]-pyrimidine (22-4) 5-chloro-6-(2,4,6-trifluorophenyl)$_{7-4}$-methylpiperidin-1-yl)[1,2,4]triazolo[1,5-a]pyrimidine Particular preference is given to active compound combinations S in which the triazolopyrimidine (group 22) of the formula (XIV) is selected from the list below:

(22-1) 5-chloro-N-[(1S)-2,2,2-trifluoro-1-methylethyl]-6-(2,4,6-trifluorophenyl)[1,2,4]triazolo-[1,5-a]pyrimidine-7-amine (22-2) 5-chloro-N-[(1R)-1,2-dimethylpropyl]-6-(2,4,6-trifluorophenyl)[1,2,4]triazolo[1,5-a]-pyrimidine-7-amine (22-4) 5-chloro-6-(2,4,6-trifluorophenyl)-7-(4-methylpiperidin-1-yl)[1,2,4]triazolo[1,5-a]pyrimidine Emphasis is given to the active compound combinations S listed in Table 19 below:

TABLE 19

Active compound combinations S

| No. | Carboxamide of the formula (I) | Triazolopyrimidine of the formula (XIV) |
|---|---|---|
| S-1 | (1-2) N-[2-(1,3-dimethylbutyl)phenyl]-5-fluoro-1,3-dimethyl-1H-pyrazole-4-carboxamide | (22-1) 5-chloro-N-[(1S)-2,2,2-trifluoro-1-methylethyl]-6-(2,4,6-trifluorophenyl)[1,2,4]triazolo-[1,5-a]pyrimidine-7-amine |
| S-2 | (1-2) N-[2-(1,3-dimethylbutyl)phenyl]-5-fluoro-1,3-dimethyl-1H-pyrazole-4-carboxamide | (22-2) 5-chloro-N-[(1R)-1,2-dimethylpropyl]-6-(2,4,6-trifluorophenyl)[1,2,4]triazolo[1,5-a]pyrimidine-7-amine |
| S-3 | (1-2) N-[2-(1,3-dimethylbutyl)phenyl]-5-fluoro-1,3-dimethyl-1H-pyrazole-4-carboxamide | (22-4) 5-chloro-6-(2,4,6-trifluorophenyl)-7-(4-methyl piperidin-1-yl)[1,2,4]triazolo[1,5-a]pyrimidine |
| S-4 | (1-8) 5-fluoro-1,3-dimethyl-N-[2-(1,3,3-trimethylbutyl)phenyl]-1H-pyrazole-4-carboxamide | (22-1) 5-chloro-N-[(1S)-2,2,2-trifluoro-1-methylethyl]-6-(2,4,6-trifluorophenyl)[1,2,4]triazolo-[1,5-a]pyrimidine-7-amine |
| S-5 | (1-8) 5-fluoro-1,3-dimethyl-N-[2-(1,3,3-trimethylbutyl)phenyl]-1H-pyrazole-4-carboxamide | (22-2) 5-chloro-N-[(1R)-1,2-dimethylpropyl]-6-(2,4,6-trifluorophenyl)[1,2,4]triazolo[1,5-a]pyrimidine-7-amine |
| S-6 | (1-8) 5-fluoro-1,3-dimethyl-N-[2-(1,3,3-trimethylbutyl)phenyl]-1H-pyrazole-4-carboxamide | (22-4) 5-chloro-6-(2,4,6-trifluorophenyl)-7-(4-methyl piperidin-1-yl)[1,2,4]triazolo[1,5-a]pyrimidine |
| S-7 | (1-10) 3-(trifluoromethyl)-1-methyl-N-[2-(1,3,3-trimethylbutyl)phenyl]-1H-pyrazole-4-carboxamide | (22-1) 5-chloro-N-[(1S)-2,2,2-trifluoro-1-methylethyl]-6-(2,4,6-trifluorophenyl)[1,2,4]triazolo-[1,5-a]pyrimidine-7-amine |
| S-8 | (1-10) 3-(trifluoromethyl)-1-methyl-N-[2-(1,3,3-trimethylbutyl)phenyl]-1H-pyrazole-4-carboxamide | (22-2) 5-chloro-N-[(1R)-1,2-dimethylpropyl]-6-(2,4,6-trifluorophenyl)[1,2,4]triazolo[1,5-a]pyrimidine-7-amine |
| S-9 | (1-10) 3-(trifluoromethyl)-1-methyl-N-[2-(1,3,3-trimethylbutyl)phenyl]-1H-pyrazole-4-carboxamide | (22-4) 5-chloro-6-(2,4,6-trifluorophenyl)-7-(4-methyl piperidin-1-yl)[1,2,4]triazolo[1,5-a]pyrimidine |
| S-10 | (1-13) N-[2-(1,3-dimethylbutyl)phenyl]-2-iodobenzamide | (22-1) 5-chloro-N-[(1S)-2,2,2-trifluoro-1-methylethyl]-6-(2,4,6-trifluorophenyl)[1,2,4]triazolo-[1,5-a]pyrimidine-7-amine |
| S-11 | (1-13) N-[2-(1,3-dimethylbutyl)phenyl]-2-iodobenzamide | (22-2) 5-chloro-N-[(1R)-1,2-dimethylpropyl]-6-(2,4,6-trifluorophenyl)[1,2,4]triazolo[1,5-a]pyrimidine-7-amine |
| S-12 | (1-13) N-[2-(1,3-dimethylbutyl)phenyl]-2-iodobenzamide | (22-4) 5-chloro-6-(2,4,6-trifluorophenyl)-7-(4-methyl piperidin-1-yl)[1,2,4]triazolo[1,5-a]pyrimidine |
| S-13 | (1-14) 2-iodo-N-[2-(1,3,3-trimethylbutyl)-phenyl]benzamide | (22-1) 5-chloro-N-[(1S)-2,2,2-trifluoro-1-methylethyl]-6-(2,4,6-trifluorophenyl)[1,2,4]triazolo-[1,5-a]pyrimidine-7-amine |
| S-14 | (1-14) 2-iodo-N-[2-(1,3,3-trimethylbutyl)-phenyl]benzamide | (22-2) 5-chloro-N-[(1R)-1,2-dimethylpropyl]-6-(2,4,6-trifluorophenyl)[1,2,4]triazolo[1,5-a]pyrimidine-7-amine |
| S-15 | (1-14) 2-iodo-N-[2-(1,3,3-trimethylbutyl)-phenyl]benzamide | (22-4) 5-chloro-6-(2,4,6-trifluorophenyl)-7-(4-methyl piperidin-1-yl)[1,2,4]triazolo[1,5-a]pyrimidine |
| S-16 | (1-15) N-[2-(1,3-dimethylbutyl)phenyl]-2-(trifluoromethyl)benzamide | (22-1) 5-chloro-N-[(1S)-2,2,2-trifluoro-1-methylethyl]-6-(2,4,6-trifluorophenyl)[1,2,4]triazolo-[1,5-a]pyrimidine-7-amine |
| S-17 | (1-15) N-[2-(1,3-dimethylbutyl)phenyl]-2-(trifluoromethyl)benzamide | (22-2) 5-chloro-N-[(1R)-1,2-dimethylpropyl]-6-(2,4,6-trifluorophenyl)[1,2,4]triazolo[1,5-a]pyrimidine-7-amine |
| S-18 | (1-15) N-[2-(1,3-dimethylbutyl)phenyl]-2-(trifluoromethyl)benzamide | (22-4) 5-chloro-6-(2,4,6-trifluorophenyl)-7-(4-methyl piperidin-1-yl)[1,2,4]triazolo[1,5-a]pyrimidine |
| S-19 | (1-16) 2-(trifluoromethyl)-N-[2-(1,3,3-trimethylbutyl)phenyl]benzamide | (22-1) 5-chloro-N-[(1S)-2,2,2-trifluoro-1-methylethyl]-6-(2,4,6-trifluorophenyl)[1,2,4]triazolo-[1,5-a]pyrimidine-7-amine |
| S-20 | (1-16) 2-(trifluoromethyl)-N-[2-(1,3,3-trimethylbutyl)phenyl]benzamide | (22-2) 5-chloro-N-[(1R)-1,2-dimethylpropyl]-6-(2,4,6-trifluorophenyl)[1,2,4]triazolo[1,5-a]pyrimidine-7-amine |
| S-21 | (1-16) 2-(trifluoromethyl)-N-[2-(1,3,3-trimethylbutyl)phenyl]benzamide | (22-4) 5-chloro-6-(2,4,6-trifluorophenyl)-7-(4-methyl piperidin-1-yl)[1,2,4]triazolo[1,5-a]pyrimidine |

In addition to a carboxamide of the formula (I) (group 1), the active compound combinations T also comprise an iodochromone (group 23) of the formula (XV)

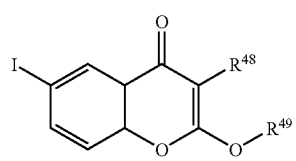

(XV)

in which $R^{48}$ and $R^{49}$ are as defined above.

Preference is given to active compound combinations T in which the iodochromone (group 23) of the formula (XV) is selected from the list below:

(23-1) 2-butoxy-6-iodo-3-propylbenzopyran-4-one (23-2) 2-ethoxy-6-iodo-3-propylbenzopyran-4-one (23-3) 6-iodo-2-propoxy-3-propylbenzopyran-4-one (23-4) 2-but-2-ynyloxy-6-iodo-3-propylbenzopyran-4-one (23-5) 6-iodo-2-(1-methylbutoxy)-3-propylbenzopyran-4-one (23-6) 2-but-3-enyloxy-6-iodobenzopyran-4-one
(23-7) 3-butyl-6-iodo-2-isopropoxybenzopyran-4-one Particular preference is given to active compound combinations T in which the iodochromone group 23) of the formula (XV) is selected from the list below:
(23-1) 2-butoxy-6-iodo-3-propylbenzopyran-4-one
(23-2) 2-ethoxy-6-iodo-3-propylbenzopyran-4-one Emphasis is given to the active compound combinations T listed in Table 20 below:

TABLE 20

Active compound combinations T

| No. | Carboxamide of the formula (I) | Iodochromone of the formula (XV) |
|---|---|---|
| T-1 | (1-2) N-[2-(1,3-dimethylbutyl)phenyl]-5-fluoro-1,3-dimethyl-1H-pyrazole-4-carboxamide | (23-1) 2-butoxy-6-iodo-3-propyl-benzopyran-4-one |
| T-2 | (1-2) N-[2-(1,3-dimethylbutyl)phenyl]-5-fluoro-1,3-dimethyl-1H-pyrazole-4-carboxamide | (23-2) 2-ethoxy-6-iodo-3-propyl-benzopyran-4-one |
| T-3 | (1-8) 5-fluoro-1,3-dimethyl-N-[2-(1,3,3-trimethylbutyl)-phenyl]-1H-pyrazole-4-carboxamide | (23-1) 2-butoxy-6-iodo-3-propyl-benzopyran-4-one |
| T-4 | (1-8) 5-fluoro-1,3-dimethyl-N-[2-(1,3,3-trimethylbutyl)-phenyl]-1H-pyrazole-4-carboxamide | (23-2) 2-ethoxy-6-iodo-3-propyl-benzopyran-4-one |
| T-5 | (1-10) 3-(trifluoromethyl)-1-methyl-N-[2-(1,3,3-trimethyl-butyl)phenyl]-1H-pyrazole-4-carboxamide | (23-1) 2-butoxy-6-iodo-3-propyl-benzopyran-4-one |
| T-6 | (1-10) 3-(trifluoromethyl)-1-methyl-N-[2-(1,3,3-trimethyl-butyl)phenyl]-1H-pyrazole-4-carboxamide | (23-2) 2-ethoxy-6-iodo-3-propyl-benzopyran-4-one |
| T-7 | (1-13) N-[2-(1,3-dimethylbutyl)phenyl]-2-iodobenzamide | (23-1) 2-butoxy-6-iodo-3-propyl-benzopyran-4-one |
| T-8 | (1-13) N-[2-(1,3-dimethylbutyl)phenyl]-2-iodobenzamide | (23-2) 2-ethoxy-6-iodo-3-propyl-benzopyran-4-one |
| T-9 | (1-14) 2-iodo-N-[2-(1,3,3-trimethylbutyl)phenyl]benzamide | (23-1) 2-butoxy-6-iodo-3-propyl-benzopyran-4-one |
| T-10 | (1-14) 2-iodo-N-[2-(1,3,3-trimethylbutyl)phenyl]benzamide | (23-2) 2-ethoxy-6-iodo-3-propyl-benzopyran-4-one |
| T-11 | (1-15) N-[2-(1,3-dimethylbutyl)phenyl]-2-(trifluoromethyl)benzamide | (23-1) 2-butoxy-6-iodo-3-propyl-benzopyran-4-one |
| T-12 | (1-15) N-[2-(1,3-dimethylbutyl)phenyl]-2-(trifluoromethyl)benzamide | (23-2) 2-ethoxy-6-iodo-3-propyl-benzopyran-4-one |
| T-13 | (1-16) 2-(trifluoromethyl)-N-[2-(1,3,3-trimethylbutyl)phenyl]benzamide | (23-1) 2-butoxy-6-iodo-3-propyl-benzopyran-4-one |
| T-14 | (1-16) 2-(trifluoromethyl)-N-[2-(1,3,3-trimethylbutyl)phenyl]benzamide | (23-2) 2-ethoxy-6-iodo-3-propyl-benzopyran-4-one |

In addition to a carboxamide of the formula (I) (group 1), the active compound combinations U also comprise a biphenylcarboxamide (group 24) of the formula (XVI)

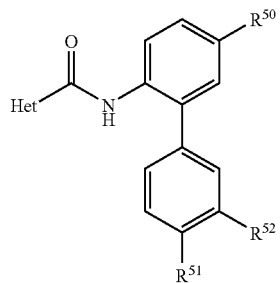

(XVI)

in which $R^{50}$, $R^{51}$, $R^{52}$ and Het are as defined above.

Preference is given to active compound combinations U in which the biphenylcarboxamide (group 24) of the formula (XVI) is selected from the list below:

(24-1) N-(3',4'-dichloro-5-fluoro-1,1'-biphenyl-2-yl)$_3$-difluoromethyl)-1-methyl-1H-pyrazole-4-carboxamide (24-2) 3-(difluoromethyl-N-{3'-fluoro-4'-[(E) (methoxyimino)methyl]-1,1'-biphenyl-2-yl}-1-methyl-1H-pyrazole-4-carboxamide (24-3) 3-t fluoromethyl)-N-{3'-fluoro-4'-[(E)-(methoxyimino)methyl]-1,1'-biphenyl-2-yl}-1-methyl-1H-pyrazole-4-carboxamide (24-4) N-(3',4'-dichloro-1,1'-biphenyl-2-yl)-5-fluoro-1,3-dimethyl-1H-pyrazole-4-carboxamide (24-5) N-4'-chloro-3'-fluoro-1,1'-biphenyl-2-yl)-2-methyl-4-trifluoromethyl)-1,3-thiazole-5-carboxamide (24-6) N-(4'-chloro-1,1'-biphenyl-2-yl)-4-(difluoromethyl)-2-methyl-1,3-thiazole-5-carboxamide (24-7) N-(4'-bromo-1,1'-biphenyl-2-yl)-4-(difluoromethyl)-2-methyl-1,3-thiazole-5-carboxamide (24-8) 4-difluoromethyl)-2-methyl-N-[4'-(trifluoromethyl)-1,1'-biphenyl-2-yl]-1,3-thiazole-5-carboxamide.

Particular preference is given to active compound combinations U in which the biphenylcarboxamide group 24) of the formula (XVI) is selected from the list below:

(24-1) N-(3',4'-dichloro-5-fluoro-1,1'-biphenyl-2-yl)-3-(difluoromethyl)-1-methyl-1H-pyrazole-4-carboxamide (24-3) 3-trifluoromethyl)-N-{3'-fluoro-4'-[(E)-(methoxyimino)methyl]-1,1'-biphenyl-2-yl}-1-methyl-1H-pyrazole-4-carboxamide (24-7) N-4'-bromo-1,1'-biphenyl-2-yl)-4-(difluoromethyl)-2-methyl-1,3-thiazole-5-carboxamide Emphasis is given to the active compound combinations U listed in Table 21 below:

TABLE 21

Active compound combinations U

| No. | Carboxamide of the formula (I) | Biphenylcarboxamide of the formula (XVI) |
|---|---|---|
| U-1 | (1-2) N-[2-(1,3-dimethylbutyl)phenyl]-5-fluoro-1,3-dimethyl-1H-pyrazole-4-carboxamide | (24-1) N-(3',4'-dichloro-5-fluoro-1,1'-biphenyl-2-yl)-3-(difluoromethyl)-1-methyl-1H-pyrazole-4-carboxamide |
| U-2 | (1-2) N-[2-(1,3-dimethylbutyl)phenyl]-5-fluoro-1,3-dimethyl-1H-pyrazole-4-carboxamide | (24-3) 3-(trifluoromethyl)-N-{3'-fluoro-4'-[(E)-(methoxyimino)methyl]-1,1'-biphenyl-2-yl}-1-methyl-1H-pyrazole-4-carboxamide |
| U-3 | (1-2) N-[2-(1,3-dimethylbutyl)phenyl]-5-fluoro-1,3-dimethyl-1H-pyrazole-4-carboxamide | (24-7) N-(4'-bromo-1,1'-biphenyl-2-yl)-4-(difluoromethyl)-2-methyl-1,3-thiazole-5-carboxamide |
| U-4 | (1-8) 5-fluoro-1,3-dimethyl-N-[2-(1,3,3-trimethylbutyl)phenyl]-1H-pyrazole-4-carboxamide | (24-1) N-(3',4'-dichloro-5-fluoro-1,1'-biphenyl-2-yl)-3-(difluoromethyl)-1-methyl-1H-pyrazole-4-carboxamide |
| U-5 | (1-8) 5-fluoro-1,3-dimethyl-N-[2-(1,3,3-trimethylbutyl)phenyl]-1H-pyrazole-4-carboxamide | (24-3) 3-(trifluoromethyl)-N-{3'-fluoro-4'-[(E)-(methoxyimino)methyl]-1,1'-biphenyl-2-yl}-1-methyl-1H-pyrazole-4-carboxamide |
| U-6 | (1-8) 5-fluoro-1,3-dimethyl-N-[2-(1,3,3-trimethylbutyl)phenyl]-1H-pyrazole-4-carboxamide | (24-7) N-(4'-bromo-1,1'-biphenyl-2-yl)-4-(difluoromethyl)-2-methyl-1,3-thiazole-5-carboxamide |
| U-7 | (1-10) 3-(trifluoromethyl)-1-methyl-N-[2-(1,3,3-trimethylbutyl)phenyl]-1H-pyrazole-4-carboxamide | (24-1) N-(3',4'-dichloro-5-fluoro-1,1'-biphenyl-2-yl)-3-(difluoromethyl)-1-methyl-1H-pyrazole-4-carboxamide |
| U-8 | (1-10) 3-(trifluoromethyl)-1-methyl-N-[2-(1,3,3-trimethylbutyl)phenyl]-1H-pyrazole-4-carboxamide | (24-3) 3-(trifluoromethyl)-N-{3'-fluoro-4'-[(E)-(methoxyimino)methyl]-1,1'-biphenyl-2-yl}-1-methyl-1H-pyrazole-4-carboxamide |
| U-9 | (1-10) 3-(trifluoromethyl)-1-methyl-N-[2-(1,3,3-trimethylbutyl)phenyl]-1H-pyrazole-4-carboxamide | (24-7) N-(4'-bromo-1,1'-biphenyl-2-yl)-4-(difluoromethyl)-2-methyl-1,3-thiazole-5-carboxamide |
| U-10 | (1-13) N-[2-(1,3-dimethylbutyl)phenyl]-2-iodobenzamide | (24-1) N-(3',4'-dichloro-5-fluoro-1,1'-biphenyl-2-yl)-3-(difluoromethyl)-1-methyl-1H-pyrazole-4-carboxamide |
| U-11 | (1-13) N-[2-(1,3-dimethylbutyl)phenyl]-2-iodobenzamide | (24-3) 3-(trifluoromethyl)-N-{3'-fluoro-4'-[(E)-(methoxyimino)methyl]-1,1'-biphenyl-2-yl}-1-methyl-1H-pyrazole-4-carboxamide |
| U-12 | (1-13) N-[2-(1,3-dimethylbutyl)phenyl]-2-iodobenzamide | (24-7) N-(4'-bromo-1,1'-biphenyl-2-yl)-4-(difluoromethyl)-2-methyl-1,3-thiazole-5-carboxamide |
| U-13 | (1-14) 2-iodo-N-[2-(1,3,3-trimethylbutyl)phenyl]benzamide | (24-1) N-(3',4'-dichloro-5-fluoro-1,1'-biphenyl-2-yl)-3-(difluoromethyl)-1-methyl-1H-pyrazole-4-carboxamide |
| U-14 | (1-14) 2-iodo-N-[2-(1,3,3-trimethylbutyl)phenyl]benzamide | (24-3) 3-(trifluoromethyl)-N-{3'-fluoro-4'-[(E)-(methoxyimino)methyl]-1,1'-biphenyl-2-yl}-1-methyl-1H-pyrazole-4-carboxamide |
| U-15 | (1-14) 2-iodo-N-[2-(1,3,3-trimethylbutyl)phenyl]benzamide | (24-7) N-(4'-bromo-1,1'-biphenyl-2-yl)-4-(difluoromethyl)-2-methyl-1,3-thiazole-5-carboxamide |
| U-16 | (1-15) N-[2-(1,3-dimethylbutyl)phenyl]-2-(trifluoromethyl)benzamide | (24-1) N-(3',4'-dichloro-5-fluoro-1,1'-biphenyl-2-yl)-3-(difluoromethyl)-1-methyl-1H-pyrazole-4-carboxamide |
| U-17 | (1-15) N-[2-(1,3-dimethylbutyl)phenyl]-2-(trifluoromethyl)benzamide | (24-3) 3-(trifluoromethyl)-N-{3'-fluoro-4'-[(E)-(methoxyimino)methyl]-1,1'-biphenyl-2-yl}-1-methyl-1H-pyrazole-4-carboxamide |
| U-18 | (1-15) N-[2-(1,3-dimethylbutyl)phenyl]-2-(trifluoromethyl)benzamide | (24-7) N-(4'-bromo-1,1'-biphenyl-2-yl)-4-(difluoromethyl)-2-methyl-1,3-thiazole-5-carboxamide |
| U-19 | (1-16) 2-(trifluoromethyl)-N-[2-(1,3,3-trimethylbutyl)phenyl]benzamide | (24-1) N-(3',4'-dichloro-5-fluoro-1,1'-biphenyl-2-yl)-3-(difluoromethyl)-1-methyl-1H-pyrazole-4-carboxamide |
| U-20 | (1-16) 2-(trifluoromethyl)-N-[2-(1,3,3-trimethylbutyl)phenyl]benzamide | (24-3) 3-(trifluoromethyl)-N-{3'-fluoro-4'-[(E)-(methoxyimino)methyl]-1,1'-biphenyl-2-yl}-1-methyl-1H-pyrazole-4-carboxamide |
| U-21 | (1-16) 2-(trifluoromethyl)-N-[2-(1,3,3-trimethylbutyl)phenyl]benzamide | (24-7) N-(4'-bromo-1,1'-biphenyl-2-yl)-4-(difluoromethyl)-2-methyl-1,3-thiazole-5-carboxamide |

In addition to an active compound of the formula (D), the active compound combinations according to the invention comprise at least one active compound from the compounds of groups (2) to (24). In addition, they may also comprise further fungicidally active additives.

If the active compounds in the active compound combinations according to the invention are present in certain weight ratios, the synergistic effect is particularly pronounced. However, the weight ratios of the active compounds in the active compound combinations can be varied within a relatively wide range. In general, the active compound combinations according to the invention comprise active compounds of the formula (I) and a mixing partner from one of the groups (2) to (24) in the mixing ratios listed in an exemplary manner in Table 22 below.

The mixing ratios are based on ratios by weight. The ratio is to be understood as active compound of the formula (I): mixing partner.

TABLE 22

Mixing ratios

| Mixing partner | | Preferred mixing ratio | Particularly preferred mixing ratio |
|---|---|---|---|
| Group (2): | strobilurins | 50:1 to 1:50 | 10:1 to 1:20 |
| Group (3): | triazoles except for (3-15) | 50:1 to 1:50 | 20:1 to 1:20 |
| (3-15): | prothioconazole | 50:1 to 1:50 | 10:1 to 1:20 |
| Group (4): | sulphenamides | 1:1 to 1:150 | 1:1 to 1:100 |
| Group (5): | valinamides | 50:1 to 1:50 | 10:1 to 1:20 |
| Group (6): | carboxamides | 50:1 to 1:50 | 20:1 to 1:20 |
| Group (7): | dithiocarbamates | 1:1 to 1:150 | 1:1 to 1:100 |
| Group (8): | acylalanines | 10:1 to 1:150 | 5:1 to 1:100 |
| Group (9): | anilinopyrimidines | 5:1 to 1:50 | 1:1 to 1:20 |
| Group (10): | benzimidazoles | 10:1 to 1:50 | 5:1 to 1:20 |
| Group (11): | carbamates except for (11-1) | 1:1 to 1:150 | 1:1 to 1:100 |
| (11-1): | diethofencarb | 50:1 to 1:50 | 10:1 to 1:20 |
| Group (12): | (12-1)/(12-2)/(12-3) | 1:1 to 1:150 | 1:5 to 1:100 |
| Group (12): | (12-4)/(12-5)/(12-6) | 5:1 to 1:50 | 1:1 to 1:20 |
| Group (13): | guanidines | 100:1 to 1:150 | 20:1 to 1:100 |
| Group (14): | imidazoles | 50:1 to 1:50 | 10:1 to 1:20 |
| Group (15): | morpholines | 50:1 to 1:50 | 10:1 to 1:20 |
| Group (16): | pyrroles | 50:1 to 1:50 | 10:1 to 1:20 |
| Group (17): | phosphonates | 10:1 to 1:150 | 1:1 to 1:100 |
| Group (18): | phenylethanamides | 50:1 to 1:50 | 10:1 to 1:20 |
| (19-1): | acibenzolar-S-methyl | 50:1 to 1:50 | 20:1 to 1:20 |
| (19-2): | chlorothalonil | 1:1 to 1:150 | 1:1 to 1:100 |
| (19-3): | cymoxanil | 10:1 to 1:50 | 5:1 to 1:20 |
| (19-4): | edifenphos | 10:1 to 1:50 | 5:1 to 1:20 |
| (19-5): | famoxadone | 50:1 to 1:50 | 10:1 to 1:20 |
| (19-6): | fluazinam | 50:1 to 1:50 | 10:1 to 1:20 |
| (19-7): | copper oxychloride | 1:1 to 1:150 | 1:5 to 1:100 |
| (19-8): | copper hydroxide | 1:1 to 1:150 | 1:5 to 1:100 |
| (19-9): | oxadixyl | 10:1 to 1:150 | 5:1 to 1:100 |
| (19-10): | spiroxamine | 50:1 to 1:50 | 10:1 to 1:20 |
| (19-11) | dithianon | 50:1 to 1:50 | 10:1 to 1:20 |
| (19-12) | metrafenone | 50:1 to 1:50 | 10:1 to 1:20 |
| (19-13) | fenamidone | 50:1 to 1:50 | 10:1 to 1:20 |
| (19-14): | 2,3-dibutyl-6-chlorothieno-[2,3-d]pyrimidin-4(3H)one | 50:1 to 1:50 | 10:1 to 1:20 |
| (19-15): | probenazole | 10:1 to 1:150 | 5:1 to 1:100 |
| (19-16): | isoprothiolane | 10:1 to 1:150 | 5:1 to 1:100 |
| (19-17): | kasugamycin | 50:1 to 1:50 | 10:1 to 1:20 |
| (19-18): | phthalide | 10:1 to 1:150 | 5:1 to 1:100 |
| (19-19): | ferimzone | 50:1 to 1:50 | 10:1 to 1:20 |
| (19-20): | tricyclazole | 50:1 to 1:50 | 10:1 to 1:20 |
| (19-21): | N-({4-[(cyclopropylamino)-carbonyl]phenyl}sulphonyl)-2-methoxybenzamide | 10:1 to 1:150 | 5:1 to 1:100 |
| (19-22) | 2-(4-chlorophenyl)-N-{2-[3-methoxy-4-(prop-2-yn-1-yloxy)phenyl]ethyl}-2-(prop-2-yn-1-yloxy)-acetamide | 50:1 to 1:50 | 10:1 to 1:20 |
| Group (20): | (thio)urea derivatives | 50:1 to 1:50 | 10:1 to 1:20 |
| Group (21): | amides | 50:1 to 1:50 | 10:1 to 1:20 |
| Group (22): | triazolopyrimidines | 50:1 to 1:50 | 10:1 to 1:20 |
| Group (23): | iodochromones | 50:1 to 1:50 | 10:1 to 1:20 |
| Group (24): | biphenylcarboxamides | 50:1 to 1:50 | 10:1 to 1:20 |

In each case, the mixing ratio is to be chosen such that a synergistic mixture is obtained. The mixing ratios between the compound of the formula (I) and a compound of one of the groups (2) to (24) may also vary between the individual compounds of a group.

The active compound combinations according to the invention have very good fungicidal properties and are suitable for controlling phytopathogenic fungi, such as Plasmodiophoroniycetes, Oomycetes, Chytridiomycetes, Zygomycetes, Ascomycetes, Basidiomycetes, Deuteromycetes, etc.

The active compound combinations according to the invention are particularly suitable for controlling *Erysiphe graminis*, *Pyrenophora teres* and *Leptosphaeria nodorum*.

Some pathogens causing fungal diseases which come under the generic names listed above may be mentioned by way of example, but not by way of limitation:

*Pythium* species, such as, for example, *Pythium ultimum*; *Phytophthora* species, such as, for example, *Phytophthora infestans*; *Pseudoperonospora* species, such as, for example, *Pseudoperonospora humuli* or *Pseudoperonospora cubensis*; *Plasmopara* species, such as, for example, *Plasmopara viticola*; *Bremia* species, such as, for example, *Bremia lactucae*; *Peronospora* species, such as, for example, *Peronospora pisi* or *P. brassicae*; *Erysiphe* species, such as, for example, *Erysiphe graminis*; *Sphaerotheca* species, such as, for example, *Sphaerotheca fuliginea*; *Podosphaera* species, such as, for example, *Podosphaera leucotricha*; *Venturia* species, such as, for example, *Venturia inaequalis*; *Pyrenophora* species, such as, for example, *Pyrenophora teres* or *P. graminea* (conidia form: *Drechslera*, syn: *Helminthosporium*); *Cochliobolus* species, such as, for example, *Cochliobolus sativus* (conidia form: *Drechslera*, syn: *Helminthosporium*);

*Uromyces* species, such as, for example, *Uromyces appendiculatus; Puccinia* species, such as, for example, *Puccinia recondita; Sclerotinia* species, such as, for example, *Sclerotinia sclerotiorum; Tilletia* species, such as, for example, *Tilletia caries; Ustilago* species, such as, for example, *Ustilago nuda* or *Ustilago avenae; Pellicularia* species, such as, for example, *Pellicularia sasakii; Pyricularia* species, such as, for example, *Pyricularia oryzae; Fusarium* species, such as, for example, *Fusarium culmorun; Botrytis* species, such as, for example, *Botrytis cinerea; Septoria* species, such as, for example, *Septoria nodorum; Leptosphaeria* species, such as, for example, *Leptosphaeria nodorum; Cercospora* species, such as, for example, *Cercospora canescens; Alternaria* species, such as, for example, *Alternaria brassicae; Pseudocercosporella* species, such as, for example, *Pseudocercosporella herpotrichoides, Rhizoctonia* species, such as, for example, *Rhizoctonia solani*.

The fact that the active compound combinations are well tolerated by plants at the concentrations required for controlling plant diseases permits a treatment of entire plants (above-ground parts of plants and roots), of propagation stock and seed, and of the soil. The active compound combinations according to the invention can be used for foliar application or else as seed dressings.

The fact that the active compounds which can be used are well tolerated by plants at the concentrations required for controlling plant diseases permits a treatment of the seed. Accordingly, the active compounds according to the invention can be used as seed dressings.

A large part of the damage to crop plants which is caused by phytopathogenic fungi occurs as early as when the seed is attacked during storage and after the seed is introduced into the soil, during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of phytopathogenic fungi which damage plants post-emergence is carried out primarily by treating the soil and the above-ground parts of plants with crop protection agents. Owing to the concerns regarding a possible impact of crop protection agents on the environment and the health of man and animals, there are efforts to reduce the amount of active compounds applied.

The control of phytopathogenic fungi by treating the seeds of plants has been known for a long time and is subject-matter of continuous improvements. However, the treatment of seed frequently entails a series of problems which cannot always be solved in a satisfactory manner. Thus, it is desirable to develop methods for protecting the seed and the germinating plant which dispense with the additional application of crop protection agents after sowing or after the emergence of the plants or where additional applications are at least reduced. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore in particular also relates to a method for the protection of seed and germinating plants from attack by phytopathogenic fungi, by treating the seed with a composition according to the invention.

The invention likewise relates to the use of the compositions according to the invention for the treatment of seed for protecting the seed and the germinating plant from phytopathogenic fungi.

Furthermore, the invention relates to seed which has been treated with a composition according to the invention so as to afford protection from phytopathogenic fungi.

One of the advantages of the present invention is that the particular systemic properties of the compositions according to the invention mean that treatment of the seed with these compositions not only protects the seed itself, but also the resulting plants after emergence, from phytopathogenic fungi. In this manner, the immediate treatment of the crop at the time of sowing or shortly thereafter can be dispensed with.

Furthermore, it must be considered as advantageous that the mixtures according to the invention can also be employed in particular in transgenic seed.

The compositions according to the invention are suitable for protecting seed of any plant variety which is employed in agriculture, in the greenhouse, in forests or in horticulture. In particular, this takes the form of seed of cereals (such as wheat, barley, rye, millet and oats), maize, cotton, soya beans, rice, potatoes, sunflowers, beans, coffee, beet (for example sugar beet and fodder beet), peanuts, vegetables (such as tomatoes, cucumbers, onions and lettuce), lawn and ornamental plants. The treatment of seed of cereals (such as wheat, barley, rye and oats), maize and rice is of particular importance.

In the context of the present invention, the composition according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, for example, it is possible to use seed which has been harvested, cleaned and dried to a moisture content of below 15% by weight. Alternatively, it is also possible to use seed which, after drying, has, for example, been treated with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the composition to the seed in the form of a suitable formulation. Suitable formulations and methods for the treatment of seed are known to the skilled worker and are described, for example, in the following documents: U.S. Pat. Nos. 4,272,417 A, 4,245,432 A, 4,808,430 A, 5,876,739 A, US 2003/0176428 A1, WO 2002/080675 A1, WO 2002/028186 A2.

The active compound combinations according to the invention are also suitable for increasing the yield of crops. In addition, they show reduced toxicity and are well tolerated by plants.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof, are treated. The term "parts" or "parts of plants" or "plant parts" has been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects, by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryEF and also combinations thereof) (hereinbelow referred to as "Bt plants"). Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IM4® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars which have these genetic traits or genetic traits still to be developed, and which will be developed and/or marketed in the future.

Depending on their particular physical and/or chemical properties, the active compound combinations according to the invention can be converted into the customary formulations, such as solutions, emulsions, suspensions, powders, dusts, foams, pastes, soluble powders, granules, aerosols, suspoemulsion concentrates, natural and synthetic materials impregnated with active compound and microencapsulations in polymeric substances and in coating compositions for seeds, and ULV cool and warm fogging formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers.

If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water.

Liquefied gaseous extenders or carriers are to be understood as meaning liquids which are gaseous at standard temperature and under atmospheric pressure, for example aerosol propellants such as butane, propane, nitrogen and carbon dioxide.

Suitable solid carriers are: for example ammonium salts and ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, pumice, marble, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The active compound content of the use forms prepared from the commercial formulations may be varied within wide ranges. The concentration of active compound of the use forms for controlling animal pests, such as insects and acarids, may be from 0.0000001 to 95% by weight of active compound and is preferably from 0.0001 to 1% by weight. Application is in a manner adapted to the use forms.

The formulations for controlling unwanted phytopathogenic fungi generally comprise between 0.1 and 95 percent by weight of active compound, preferably between 0.5 and 90%.

The active compound combinations according to the invention can be used as such, in the form of their formulations or as the use forms prepared therefrom, such as ready-to-use solutions, emulsifiable concentrates, emulsions, suspensions, wettable powders, soluble powders, dusts and granules. They are used in a customary manner, for example by watering (drenching), drip irrigation, spraying, atomizing, broadcasting, dusting, foaming, spreading-on, and as a powder for dry seed treatment, a solution for seed treatment, a water-soluble powder for seed treatment, a water-soluble powder for slurry treatment, or by encrusting.

The active compound combinations according to the invention can, in commercial formulations and in the use forms prepared from these formulations, be present as a mixture with other active compounds, such as insecticides, attractants, sterilants, bactericides, acaricides, nematicides, fungicides, growth regulators or herbicides.

When using the active compound combinations according to the invention, the application rates can be varied within a relatively wide range, depending on the kind of application. In the treatment of parts of plants, the application rates of active compound combination are generally between 0.1 and 10 000 g/ha, preferably between 10 and 1000 g/ha. In the treatment of seeds, the application rates of active compound combination are generally between 0.001 and 50 g per kilogram of seed, preferably between 0.01 and 10 g per kilogram of seed. In the treatment of the soil, the application rates of active compound combination are generally between 0.1 and 10 000 g/ha, preferably between 1 and 5000 g/ha.

The active compound combinations can be used as such, in the form of concentrates or in the form of generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if desired desiccants and UV stabilizers, and, if desired, colorants and pigments and other processing auxiliaries.

The good fungicidal action of the active compound combinations according to the invention is demonstrated by the examples below. While the individual active compounds show weaknesses in their fungicidal action, the combinations show an action which exceeds a simple sum of actions.

A synergistic effect in the fungicides is always present when the fungicidal action of the active compound combinations exceeds the total of the action of the active compounds when applied individually.

The expected fungicidal action for a given combination of two active compounds can be calculated as follows, according to S. R. Colby ("Calculating Synergistic and Antagonistic Responses of Herbicide Combinations", Weeds 1967, 15, 20-22):

If

X is the efficacy when employing active compound A at an application rate of m g/ha, Y is the efficacy when employing active compound B at an application rate of n g/ha and E is the efficacy when employing active compounds A and B at application rates of m and n g/ha, then $$E = X + Y - \frac{X \times Y}{100}$$

Here, the efficacy is determined in % 0% means an efficacy which corresponds to that of the control, whereas an efficacy of 100% means that no infection is observed.

If the actual fungicidal action exceeds the calculated value, the action of the combination is superadditive, i.e. a synergistic effect is present. In this case, the actually observed efficacy must exceed the value calculated using the above formula for the expected efficacy (E).

The invention is illustrated by the examples below. However, the invention is not limited to the examples.

USE EXAMPLES

In the use examples shown below, in each case mixtures of the carboxamides of the general formula (I) (group 1) below with the mixing partners given in each case (structural formulae see above) were tested.

Carboxamides of the formula (I) used:

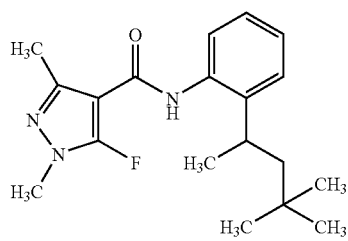
(1-8)

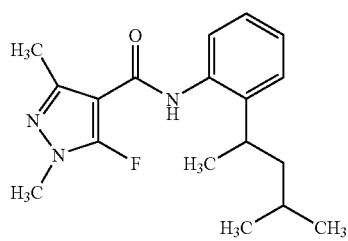
(1-2)

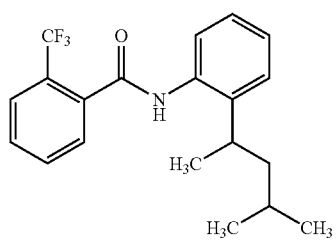
(1-15)

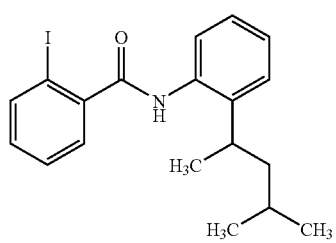
(1-13)

Example A

| *Erysiphe* test (barley)/curative | |
|---|---|
| Solvent: | 50 parts by weight of N,N-dimethylacetamide |
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for curative activity, young plants are dusted with spores of *Erysiphe graminis* f.sp. *hordei*. 48 hours after the inoculation, the plants are sprayed with the preparation of active compound at the stated application rate.

The plants are placed in a greenhouse at a temperature of about 20° C. and a relative atmospheric humidity of about 80% to promote the development of mildew pustules.

Evaluation is carried out 6 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE A

| *Erysiphe* test (barley)/curative | | | |
|---|---|---|---|
| | Application rate of | Efficacy in % | |
| Active compounds | active compound in g/ha | found* | calc.** |
| (1-8) | 25 | 0 | |
| (1-2) | 25 | 0 | |
| (3-15) prothioconazole | 25 | 22 | |
| (1-8) + (3-15) prothioconazole (1:1) | 25 + 25 | 67 | 22 |
| (1-2) + (3-15) prothioconazole (1:1) | 25 + 25 | 67 | 22 |

*found = activity found
**calc. = activity calculated using Colby's formula

Example B

| *Pyrenophora teres* test (barley)/curative | |
|---|---|
| Solvent: | 50 parts by weight of N,N-dimethylacetamide |
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for curative activity, young plants are sprayed with a conidia suspension of *Pyrenophora teres*. The plants remain in an incubation cabinet at 20° C. and 100% relative atmospheric humidity for 48 hours. The plants are then sprayed with the preparation of active compound at the stated application rate.

The plants are placed in a greenhouse at a temperature of about 20° C. and a relative atmospheric humidity of about 80%.

Evaluation is carried out 12 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE B

| *Pyrenophora teres* test (barley)/curative | | | |
|---|---|---|---|
| | Application rate of active | Efficacy in % | |
| Active compounds | compound in g/ha | found* | calc.** |
| (1-8) | 25 | 14 | |
| (1-2) | 62.5 | 71 | |
| | 25 | 29 | |
| (1-15) | 25 | 14 | |
| (2-2) fluoxastrobin | 25 | 0 | |
| (3-17) tebuconazole | 25 | 29 | |
| (2-11) picoxystrobin | 125 | 86 | |

TABLE B-continued

Pyrenophora teres test (barley)/curative

| Active compounds | Application rate of active compound in g/ha | Efficacy in % found* | calc.** |
|---|---|---|---|
| (3-12) epoxyconazole | 125 | 57 | |
| (6-7) carpropamid | 125 | 14 | |
| (6-11) 3,4-dichloro-N-(2-cyanophenyl)-isothiazole-5-carboxamide | 125 | 43 | |
| (1-8) + (2-2) fluoxastrobin (1:1) | 25 + 25 | 57 | 14 |
| (1-8) + (3-17) tebuconazole (1:1) | 25 + 25 | 57 | 39 |
| (1-2) + (2-2) fluoxastrobin (1:1) | 25 + 25 | 43 | 29 |
| (1-2) + (3-17) tebuconazole (1:1) | 25 + 25 | 57 | 50 |
| (1-2) + (2-11) picoxystrobin (1:2) | 62.5 + 125 | 100 | 96 |
| (1-2) + (3-12) epoxyconazole (1:2) | 62.5 + 125 | 93 | 88 |
| (1-2) + (6-7) carpropamid (1:2) | 62.5 + 125 | 86 | 75 |
| (1-2) + (6-11) 3,4-dichloro-N-(2-cyanophenyl)isothiazole-5-carboxamide (1:2) | 62.5 + 125 | 86 | 83 |
| (1-15) + (2-2) fluoxastrobin (1:1) | 25 + 25 | 57 | 14 |
| (1-15) + (3-17) tebuconazole (1:1) | 25 + 25 | 43 | 39 |

*found = activity found
**calc. = activity calculated using Colby's formula

Example C

Erysiphe test (barley)/protective

| Solvent: | 50 parts by weight of N,N-dimethylacetamide |
|---|---|
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are dusted with spores of *Erysiphe graminis* f.sp. *hordei*.

The plants are placed in a greenhouse at a temperature of about 20° C. and a relative atmospheric humidity of about 80% to promote the development of mildew pustules.

Evaluation is carried out 6 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE C

Erysiphe test (barley)/protective

| Active compounds | Application rate of active compound in g/ha | Efficacy in % found* | calc.** |
|---|---|---|---|
| (1-8) | 12.5 | 11 | |
| (1-2) | 12.5 | 0 | |
| (1-15) | 12.5 | 0 | |
| (1-13) | 12.5 | 0 | |

TABLE C-continued

Erysiphe test (barley)/protective

| Active compounds | Application rate of active compound in g/ha | Efficacy in % found* | calc.** |
|---|---|---|---|
| (2-4) trifloxystrobin | 12.5 | 78 | |
| (3-15) prothioconazole | 12.5 | 67 | |
| (1-8) + (2-4) trifloxystrobin (1:1) | 12.5 + 12.5 | 94 | 80 |
| (1-2) + (2-4) trifloxystrobin (1:1) | 12.5 + 12.5 | 94 | 78 |
| (1-15) + (2-4) trifloxystrobin (1:1) | 12.5 + 12.5 | 94 | 78 |
| (1-15) + (3-15) prothioconazole (1:1) | 12.5 + 12.5 | 78 | 67 |
| (1-13) + (2-4) trifloxystrobin (1:1) | 12.5 + 12.5 | 94 | 78 |

*found = activity found
**calc. = activity calculated using Colby's formula

Example D

Leptosphaeria nodorum test (wheat)/curative

| Solvent: | 50 parts by weight of N,N-dimethylacetamide |
|---|---|
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for curative activity, young plants are sprayed with a conidia suspension of *Leptosphaeria nodorum*. The plants remain in an incubation cabinet at 20° C. and 100% relative atmospheric humidity for 48 hours and are then sprayed with the preparation of active compound at the stated application rate.

The plants are placed in a greenhouse at a temperature of about 15° C. and a relative atmospheric humidity of about 80%.

Evaluation is carried out 8 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE D

Leptosphaeria nodorum test (wheat)/curative

| Active compounds | Application rate of active compound in g/ha | Efficacy in % found* | calc.** |
|---|---|---|---|
| (1-13) | 25 | 0 | |
| (2-2) fluoxastrobin | 25 | 29 | |
| (3-17) tebuconazole | 25 | 29 | |
| (1-13) + (2-2) fluoxastrobin (1:1) | 25 + 25 | 43 | 29 |
| (1-13) + (3-17) tebuconazole (1:1) | 25 + 25 | 43 | 29 |

*found = activity found
**calc. = activity calculated using Colby's formula

Example E

| *Leptosphaeria nodorum* test (wheat)/protective | |
|---|---|
| Solvent: | 50 parts by weight of N,N-dimethylacetamide |
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a spore suspension of *Leptosphaeria nodorum*. The plants remain in an incubation cabinet at 20° C. and 100% relative atmospheric humidity for 48 hours.

The plants are placed in a greenhouse at a temperature of about 15° C. and a relative atmospheric humidity of about 80%.

Evaluation is carried out 11 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE E

*Leptosphaeria nodorum* test (wheat)/protective

| Active compounds | Application rate of active compound in g/ha | Efficacy in % found* | calc.** |
|---|---|---|---|
| (1-13) | 25 | 13 | |
| (3-15) prothioconazole | 25 | 13 | |
| (1-13) + (3-15) prothioconazole (1:1) | 25 + 25 | 38 | 24 |

*found = activity found
**calc. = activity calculated using Colby's formula

Example F

| *Puccinia recondita* test (wheat)/curative | |
|---|---|
| Solvent: | 50 parts by weight of N,N-dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for curative activity, young plants are sprayed with a conidia suspension of *Puccinia recondita*. The plants remain in an incubation cabinet at 20° C. and 100% relative atmospheric humidity for 48 hours. The plants are then sprayed with the preparation of active compound at the stated application rate.

The plants are placed in a greenhouse at a temperature of about 20° C. and a relative atmospheric humidity of about 80% to promote the development of rust pustules.

Evaluation is carried out 8 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE F

*Puccinia recondita* test (wheat)/curative

| Active compounds | Application rate of active compound in g/ha | Efficacy in % found* | calc.** |
|---|---|---|---|
| (1-2) | 62.5 | 94 | |
| (2-9) kresoxim-methyl | 62.5 | 0 | |
| (19-10) spiroxamine | 62.5 | 0 | |
| (14-2) prochloraz | 62.5 | 0 | |
| (16-2) fludioxonil | 62.5 | 0 | |
| (6-14) penthiopyrad | 62.5 | 44 | |
| (1-2) + (2-9) kresoxim-methyl (1:1) | 62.5 + 62.5 | 100 | 94 |
| (1-2) + (19-10) spiroxamine (1:1) | 62.5 + 62.5 | 100 | 94 |
| (1-2) + (14-2) prochloraz (1:1) | 62.5 + 62.5 | 100 | 94 |
| (1-2) + (16-2) fludioxonil (1:1) | 62.5 + 62.5 | 100 | 94 |
| (1-2) + (6-14) penthiopyrad (1:1) | 62.5 + 62.5 | 100 | 97 |

*found = activity found
**calc. = activity calculated using Colby's formula

Example G

| *Sphaerotheca fuliginea* test (cucumber)/protective | |
|---|---|
| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at about 23° C. and a relative atmospheric humidity of about 70%.

Evaluation is carried out 7 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE G

*Sphaerotheca fuliginea* test (cucumber)/protective

| Active compounds | Application rate of active compound in g/ha | Efficacy in % found* | Efficacy in % calc.** |
|---|---|---|---|
| (1-2) | 4 | 20 | |
| | 2 | 30 | |
| | 1 | 18 | |
| | 0.5 | 0 | |
| (1-13) | 1 | 10 | |
| (2-1) azoxystrobin | 4 | 50 | |
| (2-2) fluoxastrobin | 2 | 37 | |
| (2-4) trifloxystrobin | 1 | 20 | |
| (3-3) propiconazole | 1 | 37 | |
| (3-15) prothioconazole | 1 | 43 | |
| (3-17) tebuconazole | 2 | 10 | |
| (3-21) bitertanol | 2 | 20 | |
| (4-2) tolylfluanid | 10 | 0 | |
| (6-2) boscalid | 1 | 10 | |
| (6-6) fenhexamid | 10 | 0 | |
| (7-1) mancozeb | 10 | 0 | |
| (7-4) propineb | 5 | 0 | |
| (9-3) pyrimethanil | 10 | 0 | |
| (12-4) iprodione | 10 | 0 | |
| (19-2) chlorothalonil | 10 | 0 | |
| (19-10) spiroxamine | 10 | 0 | |
| (22-1) 5-chloro-N-[(1S)-2,2,2-trifluoro-1-methylethyl]-6-(2,4,6-trifluorophenyl)-[1,2,4]triazolo[1,5-a]pyrimidine-7-amine | 1 | 22 | |
| (22-2) 5-chloro-N-[(1R)-1,2-dimethylpropyl]-6-(2,4,6-trifluorophenyl)[1,2,4]triazolo[1,5-a]-pyrimidine-7-amine | 1 | 22 | |
| (1-2) + (2-1) azoxystrobin (1:1) | 4 + 4 | 80 | 60 |
| (1-2) + (2-2) fluoxastrobin (1:1) | 2 + 2 | 88 | 56 |
| (1-2) + (2-4) trifloxystrobin (1:1) | 1 + 1 | 72 | 34 |
| (1-13) + (2-4) trifloxystrobin (1:1) | 1 + 1 | 60 | 28 |
| (1-2) + (3-3) propiconazole (1:1) | 1 + 1 | 77 | 48 |
| (1-13) + (3-3) propiconazole (1:1) | 1 + 1 | 63 | 43 |
| (1-2) + (3-15) prothioconazole (1:1) | 1 + 1 | 90 | 53 |
| (1-2) + (3-17) tebuconazole (1:1) | 2 + 2 | 80 | 37 |
| (1-2) + (3-21) bitertanol (1:1) | 2 + 2 | 75 | 44 |
| (1-2) + (4-2) tolylfluanid (1:10) | 1 + 10 | 87 | 18 |
| (1-2) + (6-2) boscalid (1:1) | 1 + 1 | 65 | 26 |
| (1-2) + (6-6) fenhexamid (1:10) | 1 + 10 | 85 | 18 |
| (1-2) + (7-1) mancozeb (1:10) | 1 + 10 | 94 | 18 |
| (1-2) + (7-4) propineb (1:10) | 0.5 + 5 | 69 | 0 |
| (1-2) + (9-3) pyrimethanil (1:10) | 1 + 10 | 83 | 18 |
| (1-2) + (12-4) iprodione (1:10) | 1 + 10 | 91 | 18 |
| (1-2) + (19-2) chlorothalonil (1:10) | 1 + 10 | 98 | 18 |
| (1-2) + (19-10) spiroxamine (1:10) | 1 + 10 | 100 | 18 |
| (1-2) + (22-1) 5-chloro-N-[(1S)-2,2,2-trifluoro-1-methylethyl]-6-(2,4,6-trifluorophenyl)-[1,2,4]triazolo[1,5-a]pyrimidine-7-amine (1:1) | 1 + 1 | 94 | 36 |
| (1-2) + (22-2) 5-chloro-N-[(1R)-1,2-dimethylpropyl]-6-(2,4,6-trifluorophenyl)[1,2,4]triazolo[1,5-a]pyrimidine-7-amine (1:1) | 1 + 1 | 91 | 36 |

*found = activity found
**calc. = activity calculated using Colby's formula

Example H

*Alternaria solani* test (tomato)/protective

| | |
|---|---|
| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Alternaria solani*. The plants are then placed in an incubation cabinetet at about 20° C. and 100% relative atmospheric humidity.

Evaluation is carried out 3 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE H

Alternaria solani test (tomato)/protective

| Active compounds | Application rate of active compound in g/ha | Efficacy in % found* | calc.** |
|---|---|---|---|
| (1-2) | 2 | 23 | |
| | 1 | 3 | |
| (1-13) | 2 | 0 | |
| (2-3) | 2 | 32 | |
| | 1 | 39 | |
| (2-12) pyraclostrobin | 2 | 37 | |
| (8-5) benalaxyl-M | 2 | 0 | |
| (8-4) metalaxyl-M | 2 | 0 | |
| (1-2) + (2-3) (1:1) | 1 + 1 | 66 | 41 |
| (1-13) + (2-3) (1:1) | 2 + 2 | 76 | 32 |
| (1-2) + (2-12) pyraclostrobin (1:1) | 2 + 2 | 64 | 52 |
| (1-13) + (2-12) pyraclostrobin (1:1) | 2 + 2 | 79 | 37 |
| (1-2) + (8-5) benalaxyl-M (1:1) | 2 + 2 | 75 | 23 |
| (1-2) + (8-4) metalaxyl-M (1:1) | 2 + 2 | 81 | 23 |

*found = activity found
**calc. = activity calculated using Colby's formula

Example I

Phytophthora infestans test (tomato)/protective

| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Phytophthora infestans. The plants are then placed in an incubation cabinetet at about 20° C. and 100% relative atmospheric humidity.

Evaluation is carried out 3 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE I

Phytophthora infestans test (tomato)/protective

| Active compounds | Application rate of active compound in g/ha | Efficacy in % found* | calc.** |
|---|---|---|---|
| (1-2) | 25 | 0 | |
| | 10 | 5 | |
| | 2 | 0 | |
| | 1 | 18 | |
| | 0.5 | 7 | |
| (5-1) iprovalicarb | 10 | 64 | |
| (7-1) mancozeb | 2 | 73 | |
| | 1 | 52 | |
| | 0.5 | 33 | |
| (17-1) fosetyl-Al | 500 | 45 | |
| (19-13) fenamidone | 2 | 47 | |
| (5-3) benthiavalicarb | 2 | 50 | |
| (24-1) N-(3',4'-dichloro-5-fluoro-1,1'-biphenyl-2-yl)-3-(difluoromethyl)-1-methyl-1H-pyrazole-4-carboxamide | 2 | 0 | |
| | 1 | 0 | |
| | 0.5 | 0 | |
| (1-2) + (5-1) iprovalicarb (1:1) | 10 + 10 | 90 | 66 |
| (1-2) + (7-1) mancozeb (1:10) | 2 + 20 | 84 | 73 |
| | 1 + 10 | 80 | 61 |
| | 0.5 + 5 | 68 | 38 |
| (1-2) + (17-1) fosetyl-Al (1:20) | 25 + 500 | 65 | 45 |
| (1-2) + (19-3) fenamidone (1:1) | 2 + 2 | 70 | 47 |
| (1-2) + (5-3) benthiavalicarb (1:1) | 2 + 2 | 80 | 50 |
| (1-2) + (24-1) N-(3',4'-dichloro-5-fluoro-1,1'-biphenyl-2-yl)-3-(difluoromethyl)-1-methyl-1H-pyrazole-4-carboxamide (1:1) | 2 + 2 | 90 | 0 |
| | 1 + 1 | 65 | 18 |
| | 0.5 + 0.5 | 67 | 7 |

*found = activity found
**calc. = activity calculated using Colby's formula

Example J

| Plasmopara viticola test (grapevine)/protective | |
|---|---|
| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Plasmopara viticola and then remain in an incubation cabinetet at about 20° C. and 100% relative atmospheric humidity for 1 day. The plants are then placed in a greenhouse at about 21° C. and about 90% atmospheric humidity for 4 days. The plants are then moistened and placed in an incubation cabinetet for 1 day.

Evaluation is carried out 6 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE J

Plasmopara viticola test (grapevine)/protective

| Active compounds | Application rate of active compound in g/ha | Efficacy in % found* | calc.** |
|---|---|---|---|
| (1-2) | 50 | 0 | |
| | 25 | 0 | |
| (17-1) fosetyl-Al | 1000 | 58 | |
| | 500 | 33 | |
| (1-2) + (17-1) fosetyl-Al (1:20) | 50 + 1000 | 83 | 58 |
| | 25 + 500 | 58 | 33 |

*found = activity found
**calc. = activity calculated using Colby's formula

Example K

| Botrytis cinerea test (bean)/protective | |
|---|---|
| Solvents: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, 2 small pieces of agar colonized by Botrytis cinerea are placed onto each leaf. The inoculated plants are placed in a darkened chamber at about 20° C. and 100% relative atmospheric humidity.

The size of the infected areas on the leaves is evaluated 2 days after the inoculation. 0% means an efficacy which corresponds to that of the control, whereas an efficacy of 100% means that no infection is observed.

The table below clearly shows that the activity found for the active compound combination according to the invention is higher than the calculated activity, i.e. that a synergistic effect is present.

TABLE K

Botrytis cinerea test (bean)/protective

| Active compounds | Application rate of active compound in g/ha | Efficacy in % found* | calc.** |
|---|---|---|---|
| (1-2) | 20 | 66 | |
| | 10 | 64 | |
| | 5 | 33 | |
| (12-4) iprodione | 20 | 47 | |
| | 10 | 54 | |
| | 5 | 13 | |
| (1-2) + (12-4) iprodione (1:1) | 20 + 20 | 94 | 82 |
| | 10 + 10 | 91 | 83 |
| | 5 + 5 | 72 | 42 |

*found = activity found
**calc. = activity calculated using Colby's formula

Example L

Pyricularia oryzae Test (In Vitro)/Microtitre Plates

The microtest is carried out in microtitre plates using potato dextrose broth (PDB) as liquid test medium. The active compounds are used as technical grade a.i., dissolved in acetone. For inoculation, a spore suspension of Pyricularia oryzae is used. After 3 days of incubation in the dark and with shaking (10 Hz) for each filled cavity of the microtitre plates, the light transmittance is determined with the aid of a spectrophotometer.

0% means an efficacy which corresponds to the growth in the controls, whereas an efficacy of 100% means that no fungal growth is observed.

The table below clearly shows that the activity found for the active compound combination according to the invention is higher than the calculated activity, i.e. that a synergistic effect is present.

TABLE L

Pyricularia oryzae test (in vitro)/microtitre plates

| Active compounds | Application rate of active compound in ppm | Efficacy in % found* | calc.** |
|---|---|---|---|
| (1-2) | 3 | 17 | |
| (14-3) triazoxide | 3 | 3 | |
| (1-2) + (14-3) triazoxide (1:1) | 3 + 3 | 53 | 20 |

*found = activity found
**calc. = activity calculated using Colby's formula

Example M

Rhizoctonia solani Test (In Vitro)/Microtitre Plates

The microtest is carried out in microtitre plates using potato dextrose broth (PDB) as liquid test medium. The active compounds are used as technical grade a.i., dissolved in acetone. For inoculation, a mycelium suspension of *Rhizoctonia solani* is used. After 5 days of incubation in the dark and with shaking (10 Hz) for each filled cavity of the microtitre plates, the light transmittance is determined with the aid of a spectrophotometer.

0% means an efficacy which corresponds to the growth in the controls, whereas an efficacy of 100% means that no fungal growth is observed.

The table below clearly shows that the activity found for the active compound combination according to the invention is higher than the calculated activity, i.e. that a synergistic effect is present.

TABLE M

Rhizoctonia solani test (in vitro)/microtitre plates

| Active compounds | Application rate of active compound in ppm | Efficacy in % found* | calc.** |
|---|---|---|---|
| (1-2) | 1 | 40 | |
| | 0.003 | 30 | |
| (11-2) propamocarb | 1 | 7 | |
| (20-1) pencycuron | 1 | 54 | |
| (24-1) N-(3',4'-dichloro-5-fluoro-1,1'-biphenyl-2-yl)-3-(difluoromethyl)-1-methyl-1H-pyrazole-4-carboxamide | 0.003 | 50 | |
| (1-2) + (11-2) propamocarb (1:1) | 1 + 1 | 78 | 44 |
| (1-2) + (20-1) pencycuron (1:1) | 1 + 1 | 91 | 72 |
| (1-2) + (24-1) N-(3',4'-dichloro-5-fluoro-1,1'-biphenyl-2-yl)-3-(difluoromethyl)-1-methyl-1H-pyrazole-4-carboxamide (1:1) | 0.003 + 0.003 | 92 | 65 |

*found = activity found
**calc. = activity calculated using Colby's formula

Example N

Gibberella zeae Test (In Vitro)/Microtitre Plates

The microtest is carried out in microtitre plates using potato dextrose broth (PDB) as liquid test medium. The active compounds are used as technical grade a.i., dissolved in acetone. For inoculation, a spore suspension of *Gibberella zeae* is used. After 3 days of incubation in the dark and with shaking (10 Hz) for each filled cavity of the microtitre plates, the light transmittance is determined with the aid of a spectrophotometer.

0% means an efficacy which corresponds to the growth in the controls, whereas an efficacy of 100% means that no fungal growth is observed.

The table below clearly shows that the activity found for the active compound combination according to the invention is higher than the calculated activity, i.e. that a synergistic effect is present.

TABLE N

Gibberella zeae test (in vitro)/microtitre plates

| Active compounds | Application rate of active compound in ppm | Efficacy in % found* | calc.** |
|---|---|---|---|
| (1-2) | 0.3 | 39 | |
| (19-3) fenamidone | 0.3 | 15 | |
| (1-2) + (19-3) fenamidone (1:1) | 0.3 + 0.3 | 70 | 48 |

*found = activity found
**calc. = activity calculated using Colby's formula

Example O

Botitis cinerea Test (In Vitro)/Microtitre Plates

The microtest is carried out in microtitre plates using potato dextrose broth (PDB) as liquid test medium. The active compounds are used as technical grade a.i., dissolved in acetone. For inoculation, a spore suspension of *Botrytis cinerea* is used. After 7 days of incubation in the dark and with shaking (10 Hz) for each filled cavity of the microtitre plates, the light transmittance is determined with the aid of a spectrophotometer.

0% means an efficacy which corresponds to the growth in the controls, whereas an efficacy of 100% means that no fungal growth is observed.

The table below clearly shows that the activity found for the active compound combination according to the invention is higher than the calculated activity, i.e. that a synergistic effect is present.

TABLE O

Botrytis cinerea test (in vitro)/microtitre plates

| Active compounds | Application rate of active compound in ppm | Efficacy in % found* | calc.** |
|---|---|---|---|
| (1-2) | 3 | 35 | |
| (10-3) carbendazim | 3 | 86 | |
| (1-2) + (10-3) carbendazim (1:1) | 3 + 3 | 97 | 91 |

*found = activity found
**calc. = activity calculated using Colby's formula

The invention claimed is:
1. A synergistic fungicidal active compound combination comprising synergistically effective amounts of
(a) a carboxamide of formula (I-2)

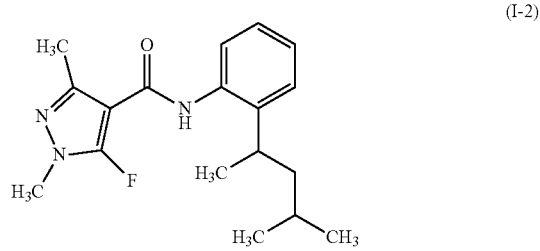 [SMILES: Cc1nn(C)c(F)c1C(=O)Nc1ccccc1C(C)CC(C)C]

(I-2)

and (b) a compound selected from the group consisting of (2-2) fluoxastrobin, wherein the ratio of compound (a) to compound (b) is 10:1 to 1:10, (2-4) trifloxystrobin, wherein the ratio of compound (a) to compound (b) is 10:1 to 1:10, (3-15) prothioconazole, wherein the ratio of compound (a) to compound (b) is 10:1 to 1:10, (3-17) tebuconazole, wherein the ratio of compound (a) to compound (b) is 10:1 to 1:10, and (8-4) metalaxyl-M., wherein the ratio of compound (a) to compound (b) is 1:1 to 1:4.

2. The synergistic fungicidal active compound combination according to claim 1, wherein the ratio of compound (a) and compound (b) is 1:1.

3. The synergistic fungicidal active compound combination according to claim 1, wherein (b) is (2-2) fluoxastrobin.

4. The synergistic fungicidal active compound combination according to claim 1, wherein (b) is (2-4) trifloxystrobin.

5. The synergistic fungicidal active compound combination according to claim 1, wherein (b) is (3-15) prothioconazole.

6. The synergistic fungicidal active compound combination according to claim 1, wherein (b) is (3-17) tebuconazole.

7. The synergistic fungicidal active compound combination according to claim 1, wherein (b) is (8-4) metalaxyl M.

8. The synergistic fungicidal active compound combination according to claim 1, wherein said (a) and (b) are the only active compounds in the combination.

9. Seed treated with a synergistic fungicidal active compound combination according to claim 1.

10. A method comprising applying an effective amount of an active compound combination according to claim 1 to seed.

11. A method according to claim 10 wherein the seed is the seed of a transgenic plant.

12. A method of controlling phytopathogenic fungi comprising applying an effective amount of a synergistic fungicidal active compound according to claim 1 to the phytopathogenic fungi and/or their habitat and/or seed for which such control is desired.

13. A method of protecting transgenic plants from phytopathogenic fungi comprising applying an effective amount of an active compound combination according to claim 1 to the transgenic plants and/or their habitat.

14. A process for preparing fungicidal compositions comprising mixing one or more active compound combinations according to claim 1 with one or more extenders and/or surfactants.

* * * * *